United States Patent
Nishtala et al.

(10) Patent No.: US 8,337,411 B2
(45) Date of Patent: Dec. 25, 2012

(54) INTRA-ABDOMINAL PRESSURE MONITORING SYSTEM

(75) Inventors: Vasu Nishtala, Snellville, GA (US); Rex Nagao, Tokyo (JP); Scott D. Ferguson, Atlanta, GA (US); Robin J. Hanson, Lawrenceville, GA (US); Anatoly Solunin, St. Petersburg (RU); Alexander Shamray, St. Petersburg (RU)

(73) Assignee: C. R. Bard, Inc., Murray Hill, NJ (US)

( * ) Notice: Subject to any disclaimer, the term of this patent is extended or adjusted under 35 U.S.C. 154(b) by 882 days.

(21) Appl. No.: 11/994,910

(22) PCT Filed: Jul. 13, 2006

(86) PCT No.: PCT/US2006/027264
§ 371 (c)(1),
(2), (4) Date: Dec. 22, 2008

(87) PCT Pub. No.: WO2007/018963
PCT Pub. Date: Feb. 15, 2007

(65) Prior Publication Data
US 2009/0221933 A1 Sep. 3, 2009

Related U.S. Application Data

(60) Provisional application No. 60/699,301, filed on Jul. 14, 2005.

(51) Int. Cl.
*A61B 5/00* (2006.01)
*A61B 5/03* (2006.01)
*A61B 1/307* (2006.01)

(52) U.S. Cl. ........ 600/561; 600/579; 600/580; 600/581; 604/544

(58) Field of Classification Search ............... 600/561, 600/579, 580, 581; 604/544
See application file for complete search history.

(56) References Cited

U.S. PATENT DOCUMENTS

| 790,353 A | 5/1905 | Estlingen |
| 1,666,332 A | 4/1928 | Hirsch |
| 3,016,915 A | 1/1962 | Moeller |
| 3,157,201 A | 11/1964 | Littmann |
| 3,411,534 A | 11/1968 | Rose |

(Continued)

FOREIGN PATENT DOCUMENTS
WO WO 96/02214 2/1996
(Continued)

OTHER PUBLICATIONS

Kron et al; Ann Surg.; 199(1): 28-30; Jan. 1984.
(Continued)

*Primary Examiner* — Sean Dougherty
(74) *Attorney, Agent, or Firm* — Rutan & Tucker, LLP

(57) ABSTRACT

Described herein are devices, systems, kits and methods for measuring intra-abdominal pressure (IAP) from a patient catheterized with a urinary catheter system. Devices may include a bypass lumen configured to connect to a pressure transducer, a sampling port connector connected to the bypass lumen, a drain tube housing configured to at least partially enclose a portion of the drain tube of a urinary catheter system, and a clamp mechanism. The sampling port connector may be configured for removable attachment to the sampling port of the urinary catheter system to form a fluid connection between the urinary catheter system and the bypass lumen of the IAP device. The clamp mechanism may be configured to controllably occlude the lumen of the urinary catheter system drain tube.

26 Claims, 58 Drawing Sheets

U.S. PATENT DOCUMENTS

| | | |
|---|---|---|
| 3,570,488 A | 3/1971 | Diskin et al. |
| 3,805,830 A | 4/1974 | Smith |
| 3,918,490 A | 11/1975 | Goda |
| 3,985,134 A | 10/1976 | Lissot et al. |
| 4,051,867 A | 10/1977 | Forberg |
| 4,061,142 A | 12/1977 | Tuttle |
| 4,217,911 A | 8/1980 | Layton |
| 4,227,533 A | 10/1980 | Godfrey |
| 4,300,571 A | 11/1981 | Waldbillig |
| 4,301,811 A | 11/1981 | Layton |
| 4,425,113 A | 1/1984 | Bilstad |
| 4,428,745 A | 1/1984 | Williams |
| 4,545,389 A | 10/1985 | Schaberg et al. |
| 4,673,389 A | 6/1987 | Archibald et al. |
| 4,683,894 A | 8/1987 | Kodama et al. |
| 4,714,463 A | 12/1987 | Archibald et al. |
| 4,821,996 A | 4/1989 | Bellotti et al. |
| 4,833,329 A | 5/1989 | Quint et al. |
| 4,867,745 A | 9/1989 | Patel |
| 4,966,161 A | 10/1990 | Wallace et al. |
| 5,000,419 A | 3/1991 | Palmer et al. |
| 5,082,025 A | 1/1992 | DeVries et al. |
| 5,097,840 A | 3/1992 | Wallace et al. |
| 5,097,868 A | 3/1992 | Betush |
| 5,385,563 A | 1/1995 | Gross |
| 5,433,216 A | 7/1995 | Sugrue et al. |
| 5,466,228 A | 11/1995 | Evans |
| 5,520,636 A | 5/1996 | Korth et al. |
| 5,823,972 A | 10/1998 | McRae |
| 5,891,134 A | 4/1999 | Goble et al. |
| 5,910,135 A | 6/1999 | Hadzic et al. |
| 5,993,395 A | 11/1999 | Shulze |
| 6,021,781 A | 2/2000 | Thompson et al. |
| 6,117,086 A | 9/2000 | Shulze |
| 6,159,160 A | 12/2000 | Hsei et al. |
| 6,183,421 B1 | 2/2001 | Bobo |
| 6,334,064 B1 | 12/2001 | Fiddian-Green |
| 6,434,418 B1 | 8/2002 | Neal et al. |
| 6,447,462 B1 | 9/2002 | Wallace et al. |
| 6,503,208 B1 | 1/2003 | Skovlund |
| 6,626,884 B1 | 9/2003 | Dillon et al. |
| 6,632,190 B2 | 10/2003 | Simonini et al. |
| 6,638,208 B1 | 10/2003 | Natarajan et al. |
| 6,673,022 B1 | 1/2004 | Bobo et al. |
| 6,673,051 B2 * | 1/2004 | Flinchbaugh ................ 604/247 |
| 6,719,709 B2 | 4/2004 | Whalen et al. |
| 6,855,126 B2 * | 2/2005 | Flinchbaugh ................ 604/106 |
| 6,896,002 B2 | 5/2005 | Hart et al. |
| 7,112,177 B2 | 9/2006 | Christensen et al. |
| 7,381,190 B2 | 6/2008 | Sugrue et al. |
| 7,892,181 B2 | 2/2011 | Christensen et al. |
| 8,052,671 B2 | 11/2011 | Christensen et al. |
| 2002/0082610 A1 | 6/2002 | Cioanta et al. |
| 2002/0115906 A1 | 8/2002 | Miller |
| 2003/0023134 A1 | 1/2003 | Tracey |
| 2003/0023135 A1 | 1/2003 | Ulmsten et al. |
| 2003/0023144 A1 | 1/2003 | Tracey et al. |
| 2003/0027326 A1 | 2/2003 | Ulmsten et al. |
| 2003/0028074 A1 | 2/2003 | Tracey et al. |
| 2003/0028075 A1 | 2/2003 | Ulmsten et al. |
| 2003/0028159 A1 | 2/2003 | Tracey et al. |
| 2004/0176703 A1 | 9/2004 | Christensen et al. |
| 2004/0230118 A1 | 11/2004 | Shehada et al. |
| 2006/0058702 A1 | 3/2006 | Christensen et al. |
| 2006/0079804 A1 | 4/2006 | Sugrue et al. |
| 2007/0038143 A1 | 2/2007 | Christensen et al. |
| 2007/0255167 A1 | 11/2007 | Christensen et al. |
| 2007/0282219 A1 | 12/2007 | Holte |
| 2008/0027373 A1 | 1/2008 | Holte |

FOREIGN PATENT DOCUMENTS

| | | |
|---|---|---|
| WO | 03001974 A2 | 1/2003 |
| WO | 03001975 A2 | 1/2003 |
| WO | 03001977 A2 | 1/2003 |
| WO | 03001978 A2 | 1/2003 |
| WO | WO 03/071944 | 9/2003 |
| WO | 2004071279 A2 | 8/2004 |
| WO | WO-2004/078235 | 9/2004 |
| WO | WO 2004/078235 | 9/2004 |
| WO | WO-2004/080519 | 9/2004 |
| WO | WO 2004/080519 | 9/2004 |
| WO | WO-2006/041496 | 4/2006 |
| WO | WO 2006/041496 | 4/2006 |
| WO | WO-2006/060248 | 6/2006 |
| WO | WO 2006/060248 | 6/2006 |

OTHER PUBLICATIONS

PCT Search Report, Application No. PCT/US06/27264, Jul. 13, 2007.

Balogh, Zsolt et al., "Continuous intra-abdominal pressure measurement technique," American Journal of Surgery, col. 188, No. 6, pp. 679-684, Dec. 2004.

EP 06787204.4 filed Jan. 8, 2008 European Search Report dated Aug. 17, 2011.

JP 2008-521621 filed Jan. 11, 2008 Office Action dated Nov. 25, 2011.

* cited by examiner

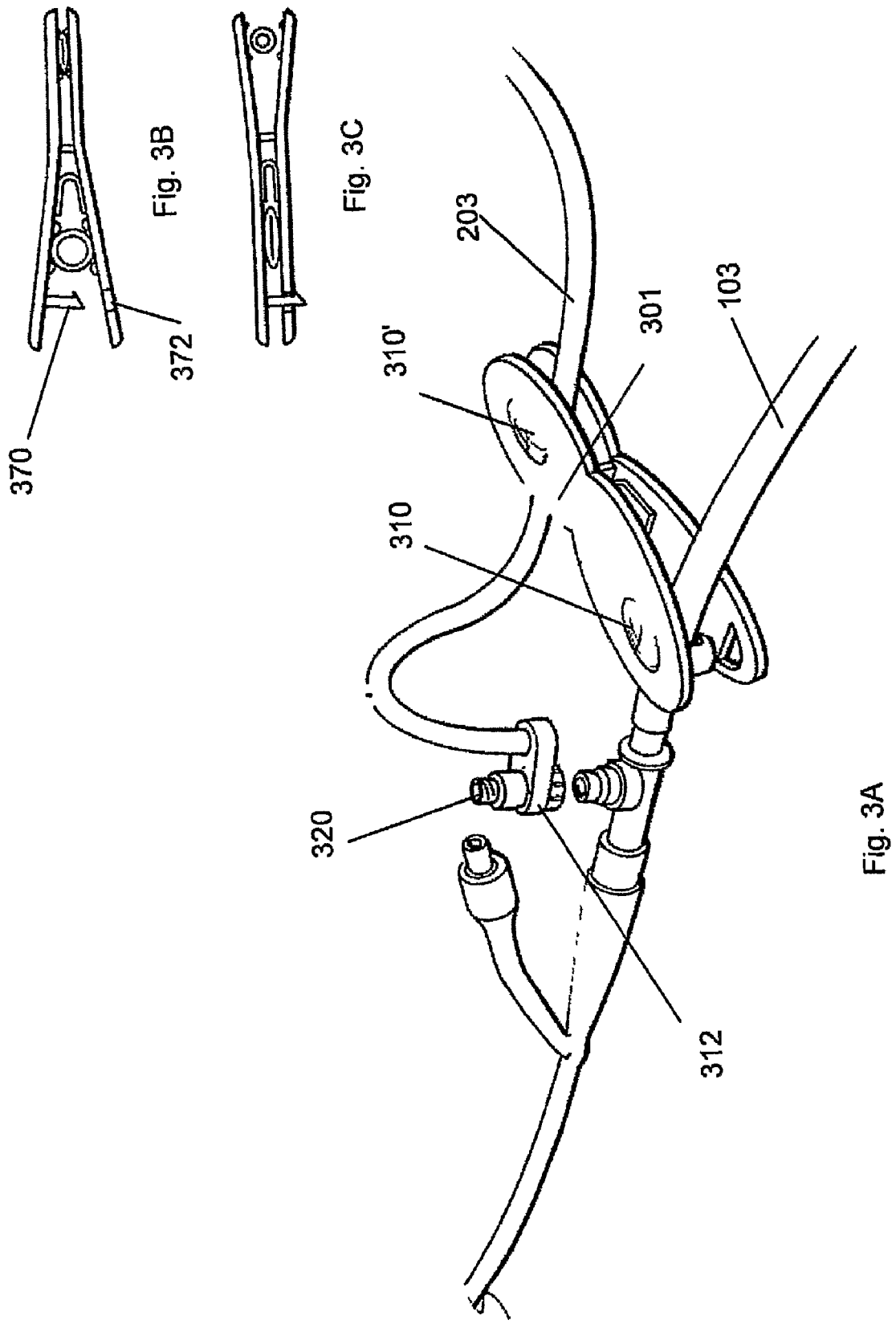

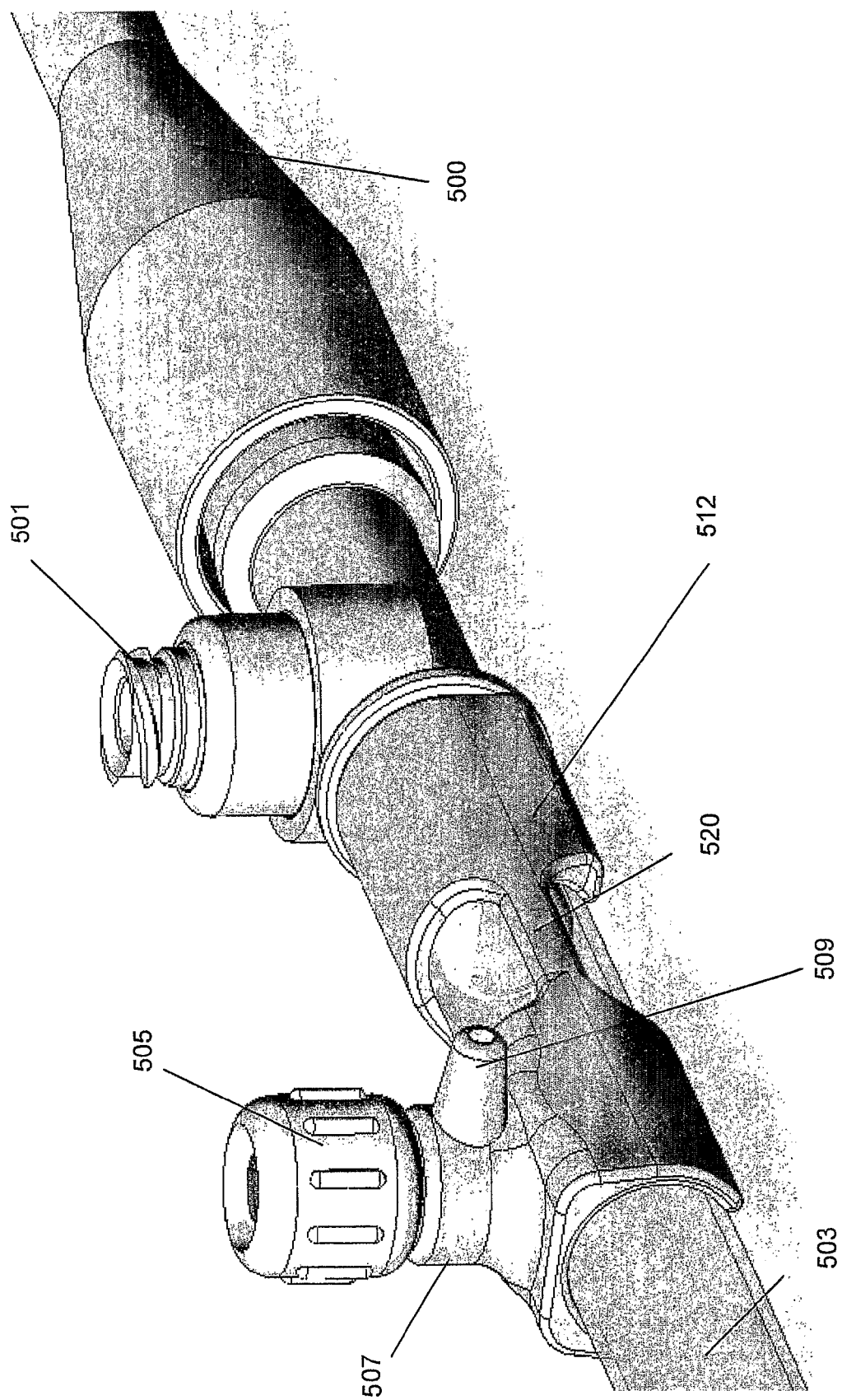

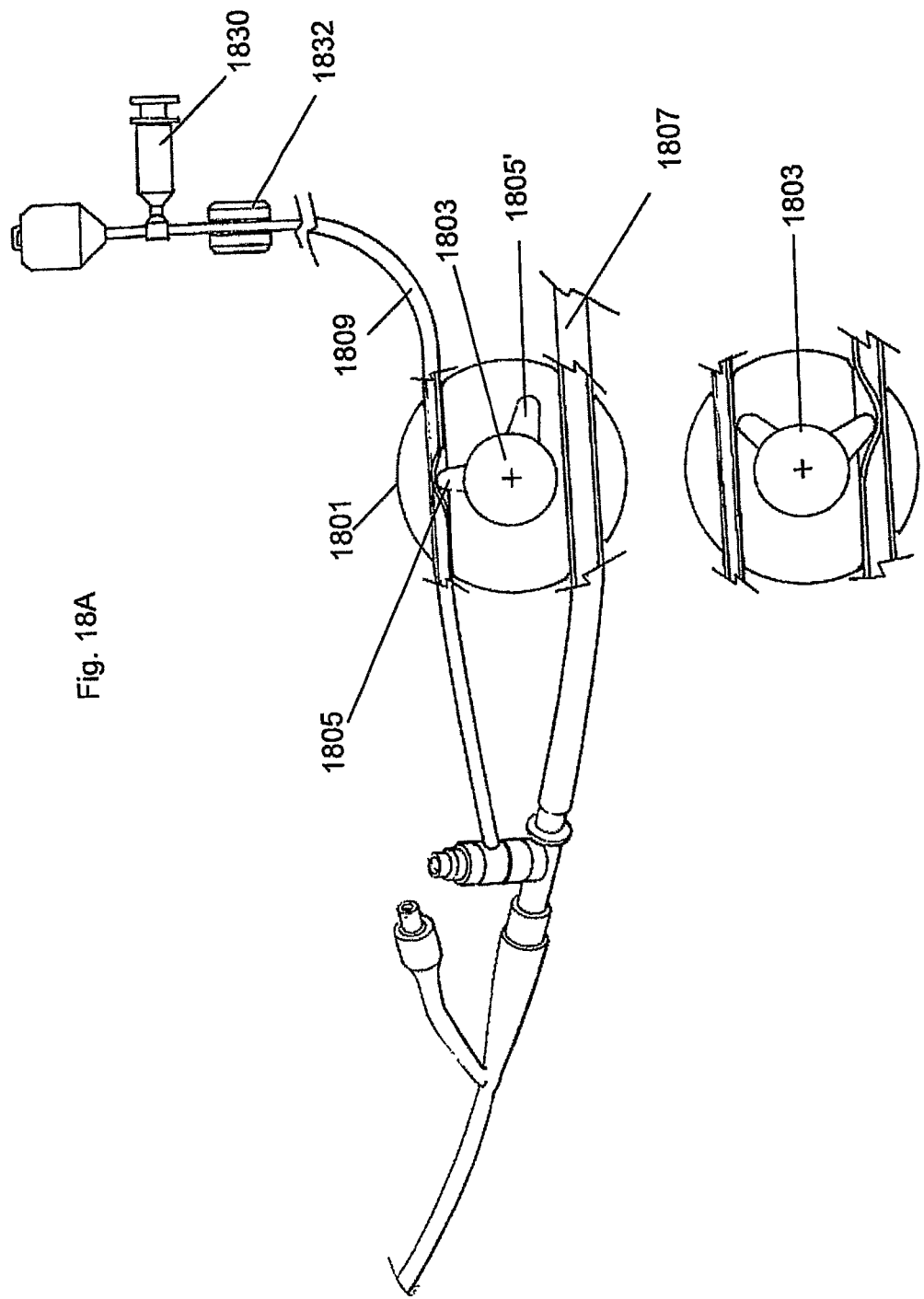

Fig. 21A
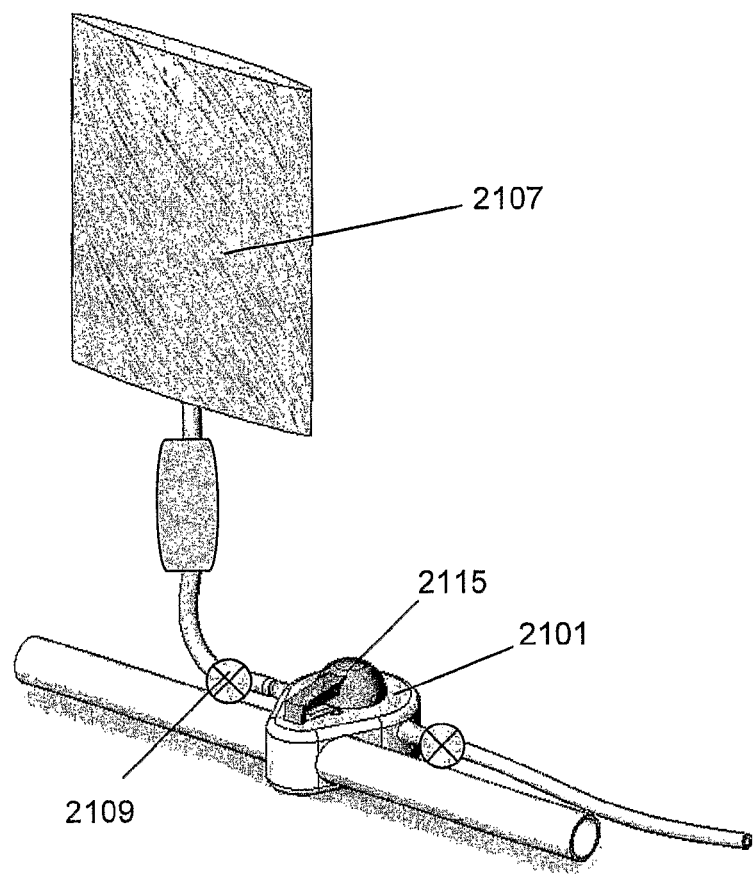
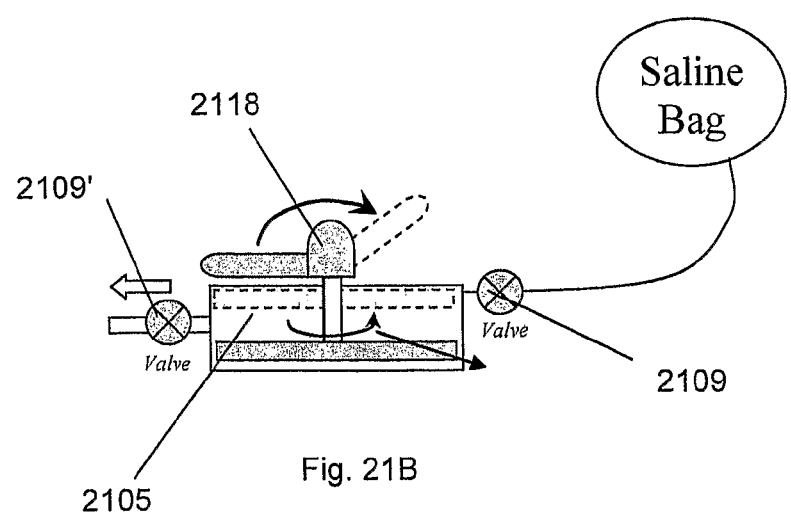
Fig. 21B

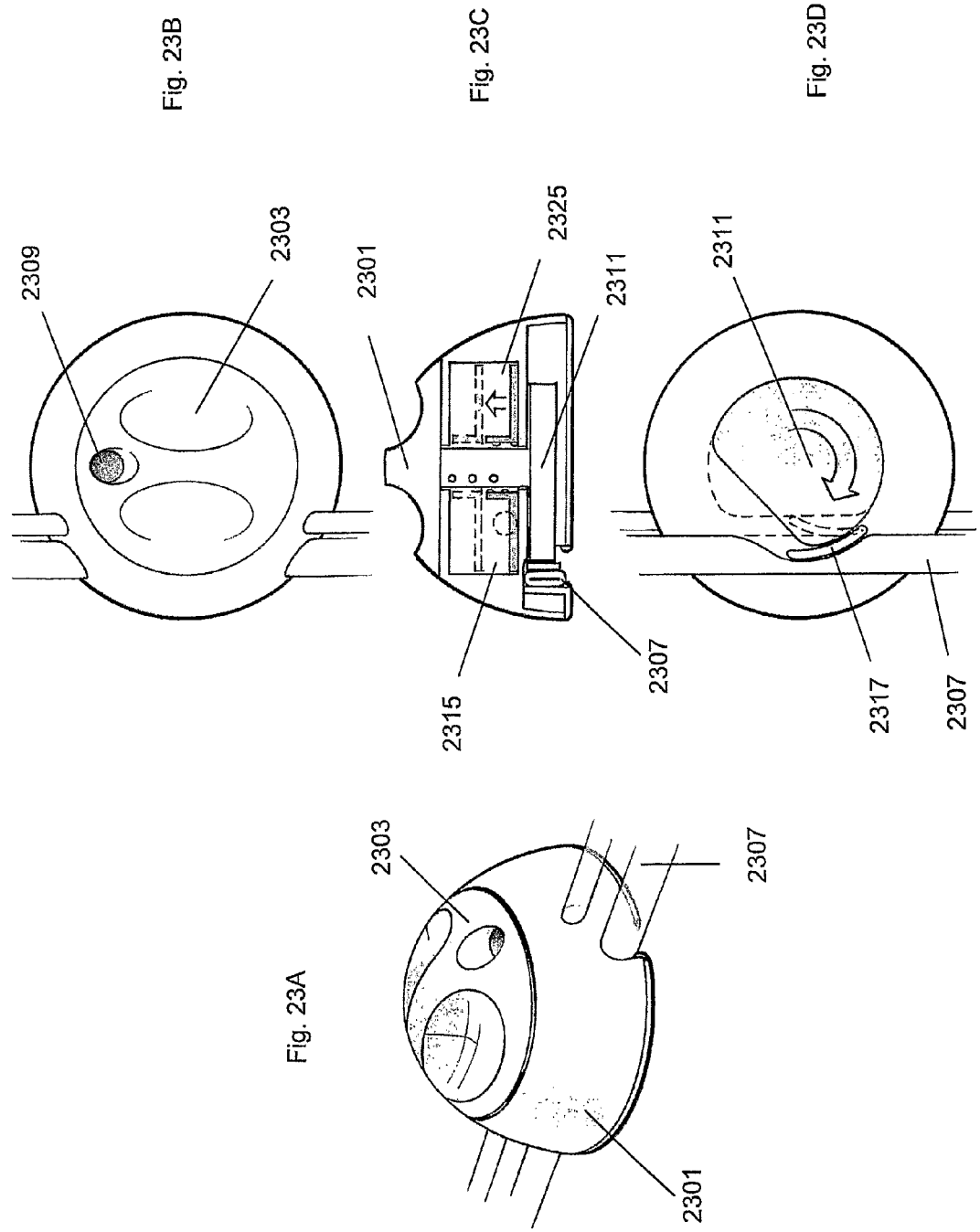

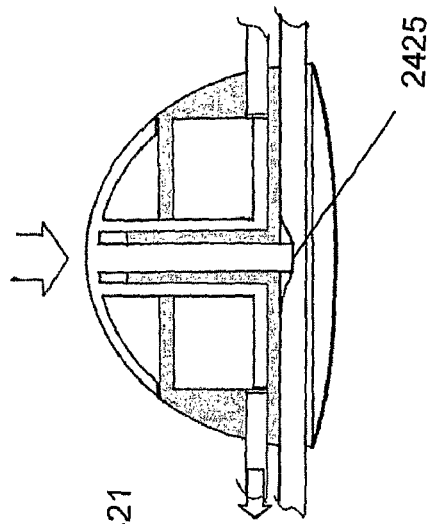
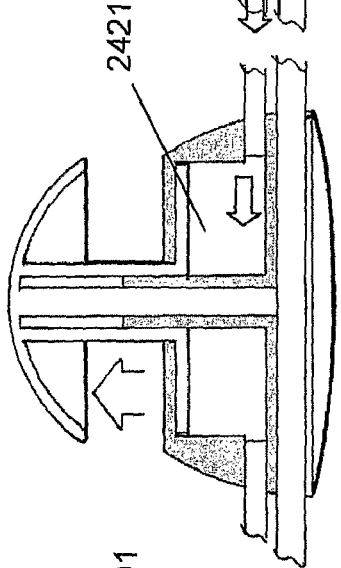
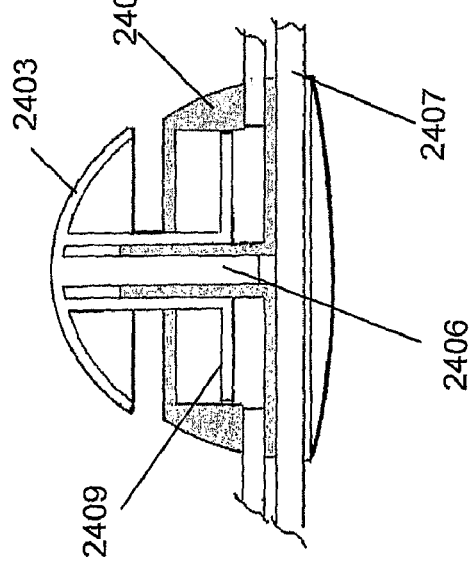
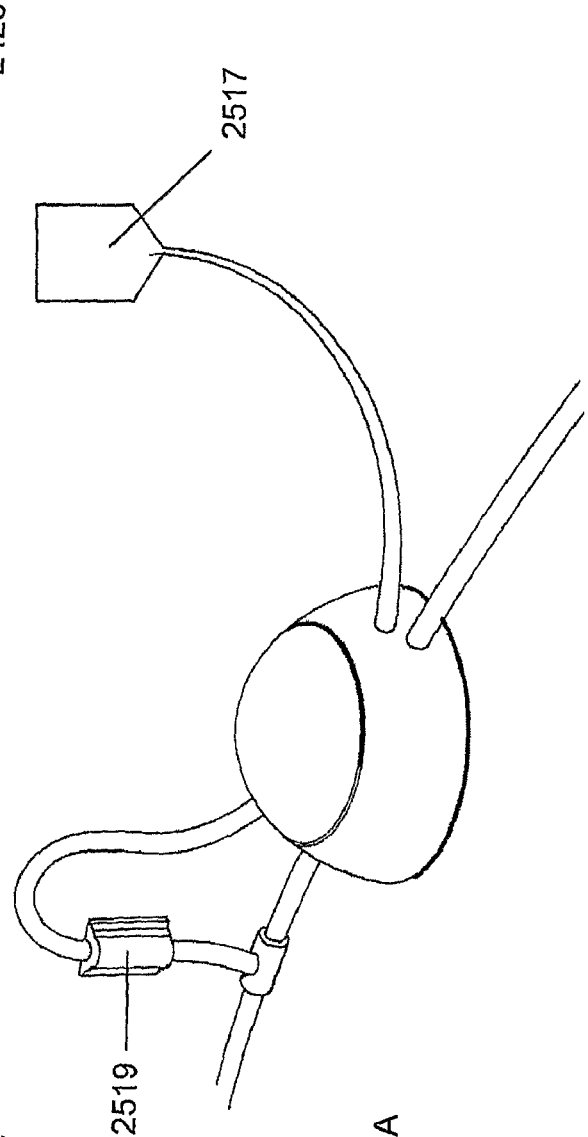

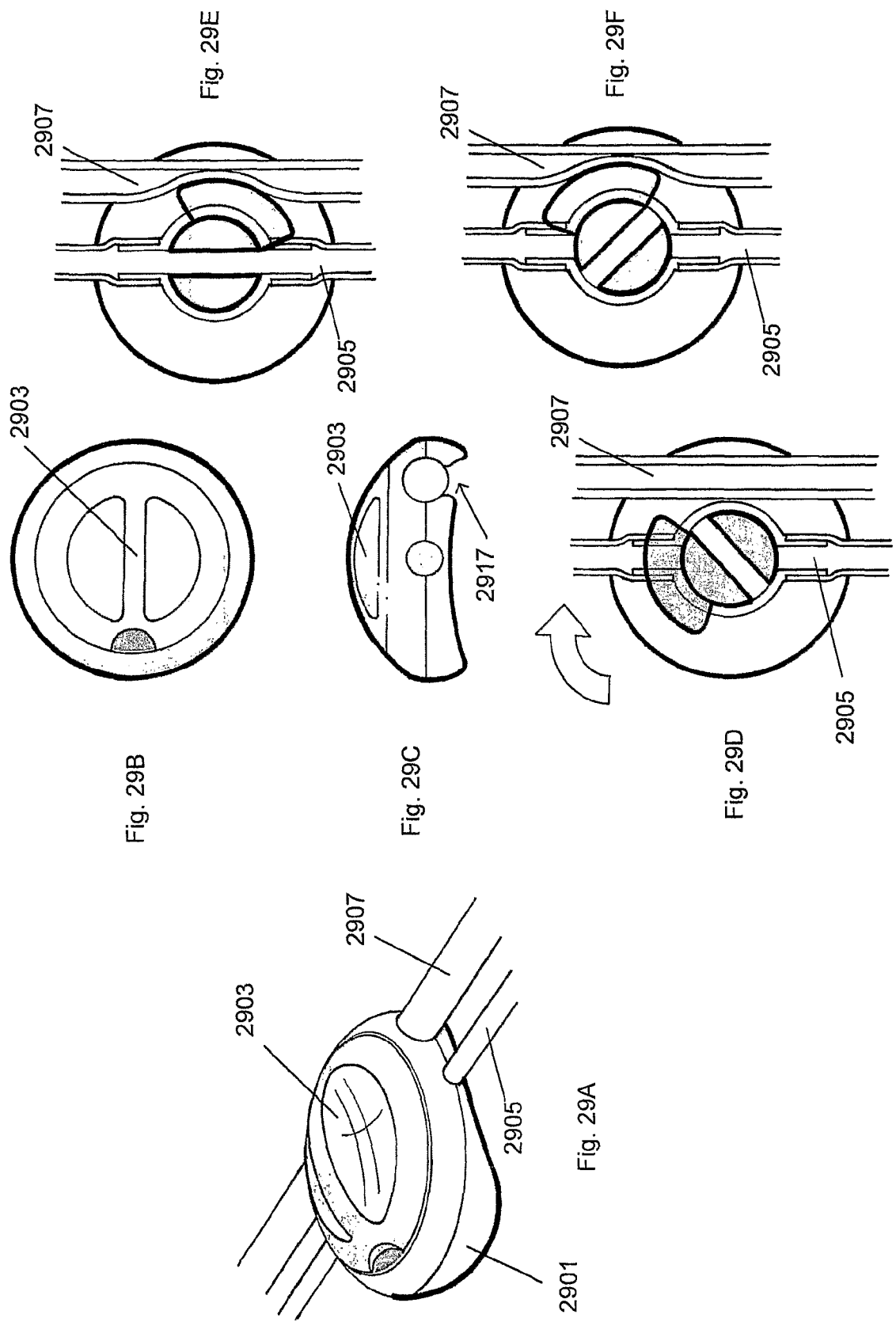

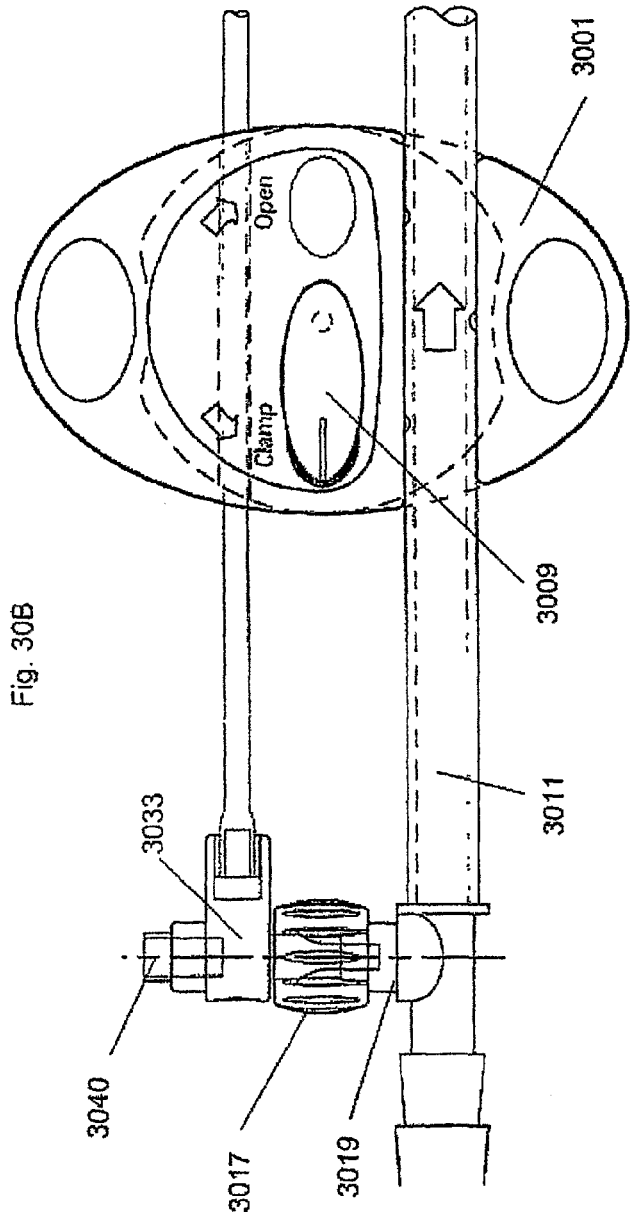
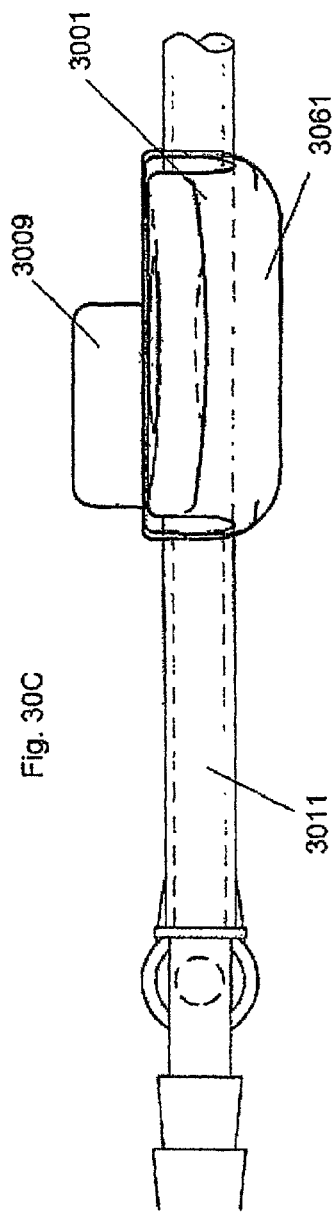
Fig. 30B
Fig. 30C

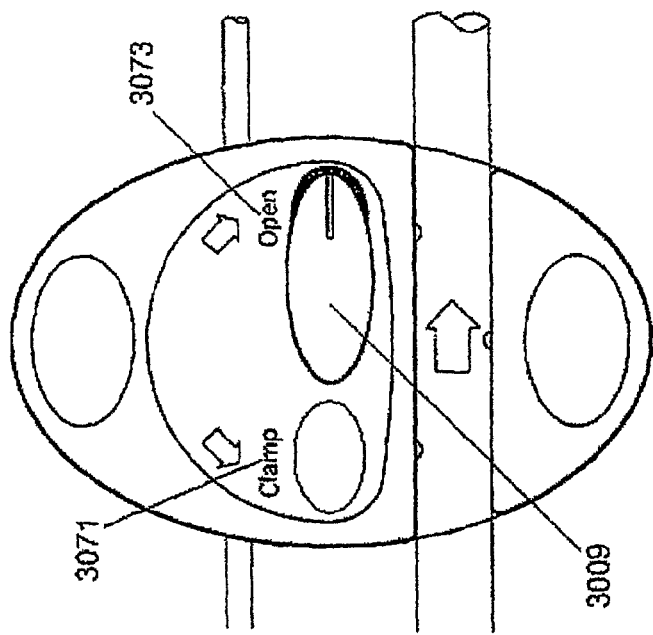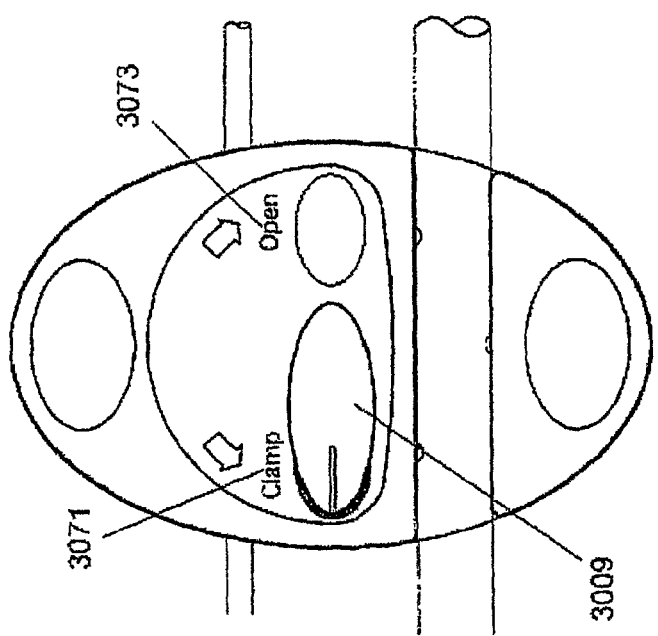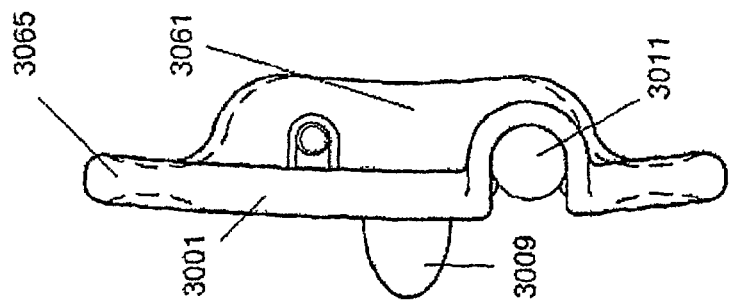

3040

3040

3012

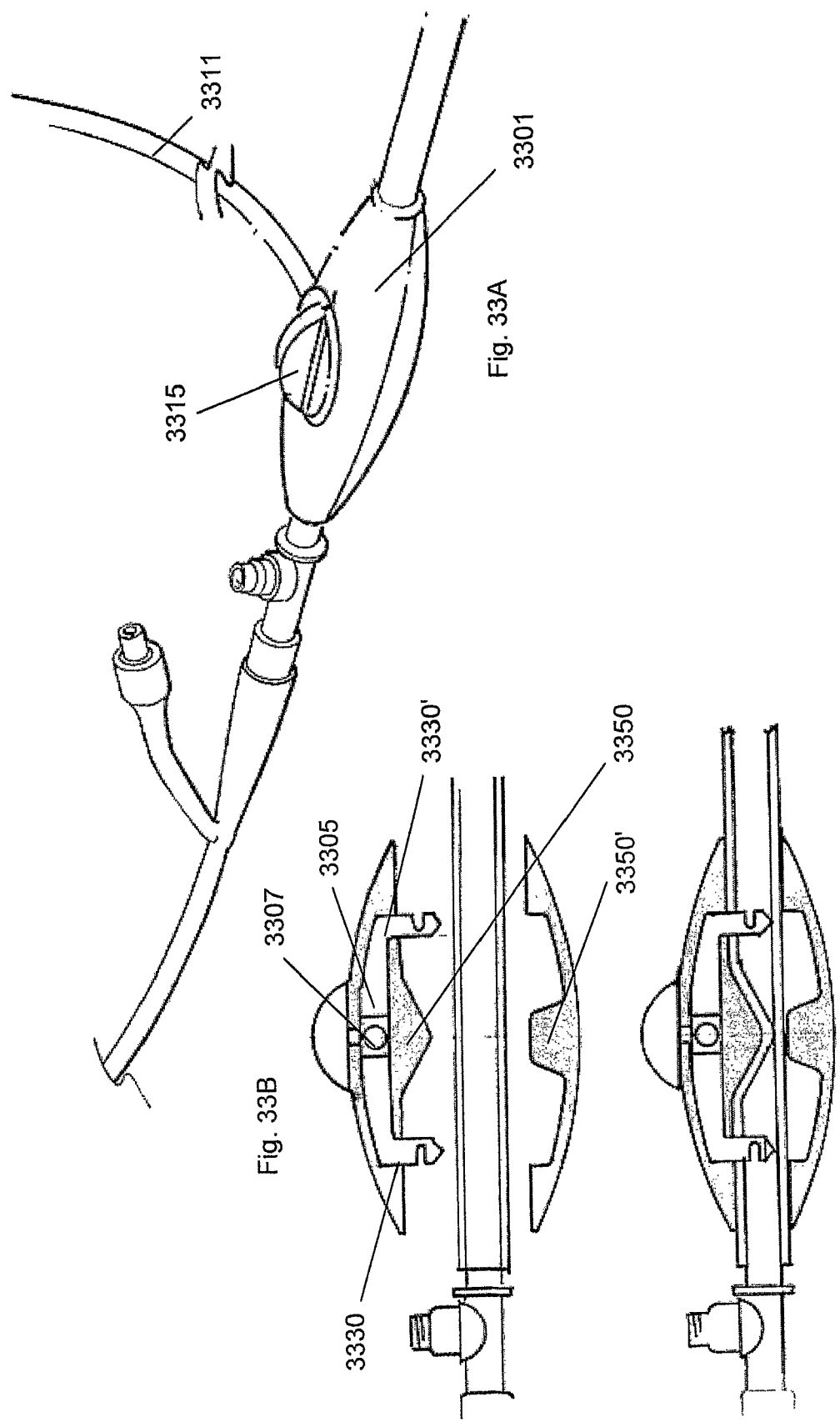

Fig. 43A
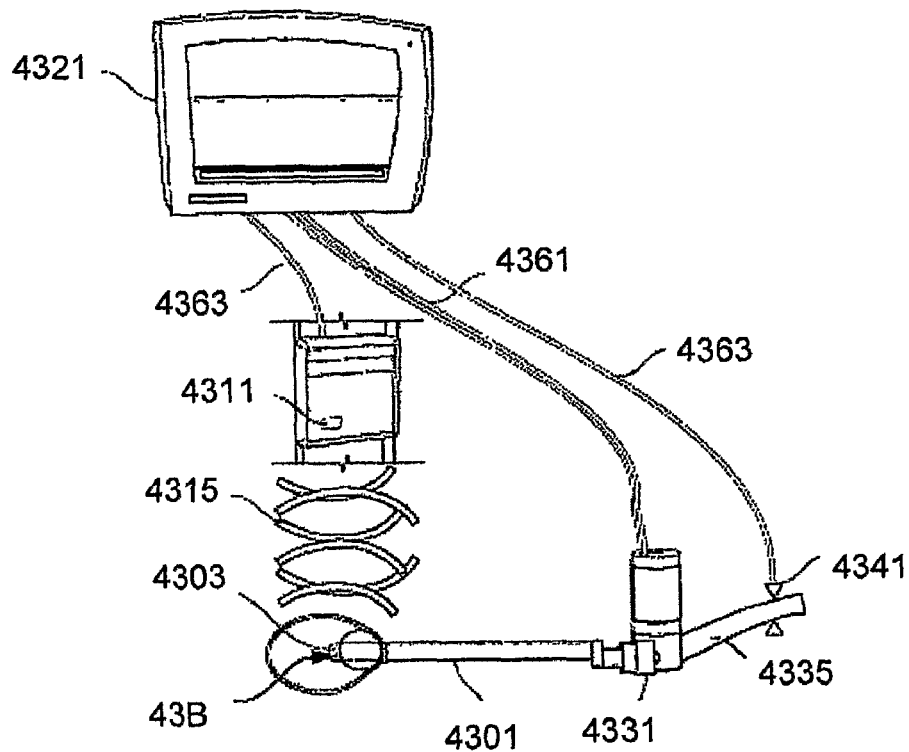
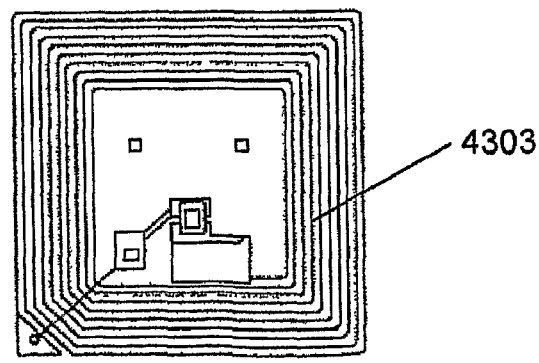
Fig. 43B

INTRA-ABDOMINAL PRESSURE MONITORING SYSTEM

PRIORITY

This application is a United States national stage application under 35 U.S.C. §371 of International Patent Application No. PCT/US2006/027264, filed Jul. 13, 2006, which claims the benefit, under 35 U.S.C. §119(e), to U.S. Provisional Application No. 60/699,301, filed Jul. 14, 2005, each of which is incorporated by reference into this application as if fully set forth herein.

BACKGROUND OF THE INVENTION

Intra-abdominal pressure (IAP) is an important parameter and prognostic indicator of a patient's underlying physiologic status. Correct IAP measurement is therefore crucial. One simple way of detecting IAP includes the measurement of bladder pressure. In particular, the measurement of bladder pressure via an indwelling urinary catheter system is a simple and effective way of indirectly measuring intra-abdominal pressure. Serial monitoring of bladder pressures is useful in detecting the onset of intra-abdominal hypertension (IAH) and the progression to the more severe condition, abdominal compartment syndrome (ACS). IAH and ACS occur when the abdominal contents expand in excess of the capacity of the abdominal cavity. Causes of IAH and ACS include intraperitoneal blood, interstitial edema from fluid resuscitation, peritonitis, ascites, and gaseous bowel distention. Both IAH and ACS have been primarily associated with trauma patients; however, patients with other pathological conditions are now being recognized as "at risk" for IAH and ACS.

Primary organ systems adversely affected by IAH and ACS include the cardiovascular, renal, pulmonary, gastrointestinal, and central nervous systems. Not only should patients be monitored for physiological changes, but intra-abdominal pressure also must be measured. Several techniques for measuring intra-abdominal pressure have been described in the literature, including a method described by Kron et al. (Kron, Hartman, and Nolan, "The measurement of intra-abdominal pressure as a criterion for abdominal re-exploration." *Ann Surg,* 199:28-30, 1984), which is incorporated by reference into this application as if fully set forth herein. These techniques include direct intraperitoneal measurement with a peritoneal dialysis catheter, intragastric measurement via a nasogastric tube, and measurement of pressure via the rectal route or through a urinary catheter system in the bladder. Although the intraperitoneal route is the most direct, the need for insertion of a special catheter into the peritoneum has inherent risks that make this method undesirable for widespread clinical use. Of the remaining options, measurement of bladder pressure via an indwelling urinary catheter system has become the method of choice because of its ease and reliability.

Serial measurements of bladder pressure should be undertaken as part of the examination of any patient at risk for IAH or ACS, and the measurement of intra-abdominal pressure should be correlated with other assessment findings associated with organ system compromise.

The bladder acts as a passive reservoir and accurately reflects intra-abdominal pressure when the intravesicular volume is approximately 100 mL or less. Bladder pressure can be measured easily by using a conventional pressure transducer system connected to the patient's urinary catheter drainage system. Currently, most bladder pressure measurements are done using devices constructed by medical professions on an ad-hoc basis, who must assemble a pressure monitor using materials available in the hospital setting. Such homemade monitors require time to assemble, and may vary in quality and ease of use. Thus, they may be used less frequently than would be beneficial. These monitors do not have a standardized level or performance or sterility. These devices may leak and may require interruption of the closed catheter system. Furthermore, commercially available systems (such as the Wolfe-Tory "AbViser" System) require opening the Foley catheter system to use. An example of such a system may be seen in U.S. Patent Application Publication No. 2006/0058702 to Christensen et al., which is incorporated by reference into this application as if fully set forth herein.

Applicants have recognized that it would be particularly advantageous to provide single or multiple (e.g., serial) measurements of IAP using commercially available urine catheters, such as Foley catheters. Applicants have also recognized that it would be advantageous to perform one or more IAP measurements from a urine catheter that is part of a catheterization system already in use by a patient, without having to open the system (e.g., by detaching the drainage tube, etc.), as opening the catheterization system may result in potentially exposing a patient or medical care provider to contamination or leakage of the system. Accordingly, devices, systems and methods for taking IAP measurements that may overcome one or more of these problems and/or others are described herein.

BRIEF SUMMARY OF THE INVENTION

Devices and systems for IAP monitoring, as well as kits and methods for using them, are described herein. These devices, systems, kits, and methods provide a way for a clinician or other medical practitioner to determine intra-abdominal pressure through pressure readings from a patient's bladder.

In particular, the devices for measuring intra-abdominal pressure (IAP) from a patient may be devices that are to be used with a urinary catheter. The devices for measuring IAP descried herein may be referred to as urinary catheter system bypass devices (or as "bypass devices"), because they allow measurement of IAP from a urinary catheter system or catheter system from a catheterized patient without having to disassemble or otherwise open the closed catheter system.

Thus, devices for measuring intra-abdominal pressure from a patient catheterized with a urinary catheter system are described. In some variations, these devices are adapted to be used with catheters that have a sampling port and a drain tube. These devices may include a bypass lumen configured to fluidly connect to a pressure transducer for measuring intra-abdominal pressure, a sampling port connector in fluid connection with the bypass lumen, a drain tube housing configured to at least partially enclose a portion of the drain tube of the urinary catheter, and a clamp mechanism in communication with the drain tube housing. The sampling port connector is configured to be removably attached to the sampling port of the urinary catheter system to form a fluid connection between the urinary catheter system and the bypass lumen of the IAP device. Further, the clamp mechanism is also configured to controllably occlude the lumen of the urinary catheter system drain tube.

The bypass lumen may therefore be in fluid connection with the region or lumen of the catheter (e.g., a Foley Catheter) through which urine normally drains. Fluid may be applied to the patient's bladder through the catheter from the bypass lumen to measure IAP. Thus, the bypass lumen may connect to (or be part of) one or more fluid pathways for applying fluid into the catheter, and/or for measuring pressure. For example, the bypass lumen may be in fluid connection with a first fluid pathway that can connect to a pressure transducer. The bypass lumen may also be in fluid connection with a second fluid pathway that is configured to connect to a fluid infuser for infusing fluid through the bypass lumen. The fluid infuser (e.g., a pump such as a syringe, etc.) may itself be connected to a fluid source for applying a bolus of fluid. In some variations, the fluid pathways connecting the pressure transducer and the fluid pathway connecting the fluid infuser are part of the same fluid pathway. For example, the bypass lumen may be in fluid connection with a fluid pathway configured to connect to both a pressure transducer and a fluid infuser for infusing fluid though the bypass lumen. In some variations the device includes a pressure transducer for measuring intra-abdominal pressure.

Any appropriate fluid source (e.g., gas, liquid, etc.) may be used with the device (or as part of the device) for supplying fluid into the catheter through the fluid bypass lumen. For example, the fluid source may be a saline source (e.g., saline bag), or the like. Furthermore, any appropriate fluid infuser may be used with the device (or as part of the device) for infusing fluid through the bypass lumen and into the catheter. For example, a fluid infuser may be a fluid pump (e.g., a mechanical or electrical pump, etc.), including a syringe. In some variations, the fluid infuser is fluidly connected to the fluid source, so that fluid from the fluid source may be pumped through the bypass lumen of the device and into the urinary catheter. The fluid source and fluid infuser may be configured so that the device can be used multiple times to measure IAP. For example, the fluid infuser (e.g., syringe) may be "reloaded" with fluid from the fluid source. In some variations, the fluid source and fluid infuser are connected with valves (e.g., one-way valves, flap valves, etc.) that allow fluid to be drawn into the fluid infuser from the fluid source without drawing fluid through the bypass lumen when the fluid infuser operates in one direction (e.g., withdrawing the plunger of a syringe). Furthermore, flow between the fluid source and the fluid infuser can be prevented when the fluid infuser is delivering fluid through the bypass lumen (e.g., pushing the plunger of a syringe).

In some variations, the fluid infuser includes a metered reservoir. For example, the fluid infuser delivers a metered amount of fluid for a single measurement. The metered amount or amounts may be pre-set (e.g., based on the volume available to the fluid infuser), or may be selected based on calibration marks on a portion of the fluid infuser. In some variations, the fluid infuser and the metered reservoir are part of a housing (e.g., the drain tube housing of the device). For example, the train tube housing described above may include a fluid reservoir that can be loaded with fluid that can be controllably applied by the fluid infuser before making a measurement of IAP.

As mentioned above, the device (particularly the bypass lumen region of the device) typically connects to the urinary catheter system through a sampling port on a urinary catheter system. A urinary catheter can have one or more sampling ports through which a sample of urine can be removed during operation of the urinary catheter system after a patient has been catheterized. Even when a urinary catheter does not occlude a sampling port, the catheter system may include a sampling port as part of an attachment or as part of the drain tube. A sampling port may allow access to the lumen of the urinary catheter system without breaking or disrupting the closed urinary catheterization system. Many urinary catheter systems appropriate for use with the devices, systems, kits, and methods described herein include a sampling port that has a valve preventing leak or contamination through the sampling port Any appropriate sampling port connector may be used. In general, the sampling port connector fluidly connects the bypass lumen with the lumen of the catheter (through which urine flows) so that fluid can be delivered into the catheter from the device for the measurement of IAP. For example, a sampling port connector may include a luer lock for securing the device to the sampling port. In some variations, the sampling port connector includes an auto valve that mates with the sampling port. An auto valve, as used herein, refers to a device that can have an insertion member for opening a valve member of a sampling port (e.g., a male luer portion), a locking connector (linking member) to connect the auto valve to the sampling port (e.g., a female threaded member for threading over male threads of an EZ-LOK™) and a fluid injection line/port that can be connected to the bypass lumen (e.g., a tube or other fluid conduit as described above). The auto valve may allow the bypass lumen to communicate with the urinary catheter system and permit fluid infusion into the bladder. When the auto valve is disengaged from the sampling port, fluid infusion through the fluid injection line is precluded. In one embodiment, the insertion member of the auto valve may itself have a valve member associated therewith, such that connection of the auto valve to the sampling port opens both valve members for fluid flow therethrough.

In some variations, the sampling port connector also includes an auxiliary sampling port. The auxiliary sampling port may be configured to allow sampling of urine within the urinary catheter system even when the device (e.g., the bypass device) is attached to the sampling port of the urinary catheter. An auxiliary sampling port may be the same kind of sampling port that is on the catheter, or it may be a different type. For example, the auxiliary sampling port may include an EZ-LOK™ mechanism. The auxiliary sampling port may allow the IAP system to modularly attach to a catheter system while maintaining the functionality of the drainage system (e.g., including sampling of urine) and attachment of additional components.

A drain tube housing (which may also be referred to as a housing) typically encloses at least a portion of the drain tube of a catheter. In some variations, the drain tube housing locks around the drain tube portion of an indwelling catheter (e.g., the catheter in a catheterized patient). The drain tube housing may include one or more channels for holding at least a portion of the drain tube. For example, the drain tube housing may include a channel into which a portion of the drain tube fits. The housing may close around the drain tube so that the drain tube is secured within the channel of the drain tube housing. In some variations, the drain tube housing has a first housing region and a second housing region, so that the first housing region is (at least partly) separable from the second body housing region. When the two housing regions are separated, the catheter drain tube can be inserted between them. The two regions may then be closed around the drain tube. In some variations, the housing includes a spring or other bias that holds the regions together and secures it around the drain tubing. In some variations, the housing may include one or more locks for locking the housing around the drain tube. A lock may be an elastomeric material, a latch, or the like.

The drain tube housing may also house or provide attachment for additional components that may be included as part of the devices for measuring IAP described herein. In some variations, the housing may also house a portion of the bypass lumen. The drain tube housing may include a fluid infuser and/or a fluid reservoir or fluid source. The sampling port connector may also be attached to the drain tube housing.

A clamp mechanism typically occludes the drain tube, preventing draining of urine through the drain tube of the catheter when the clamp mechanism is engaged. Thus, the clamp mechanism may control flow through the drain tube. The clamp mechanism may be at least partly within the drain tube housing, and acts on the region of the tubing within the drain tube housing. Any appropriate type of clamp mechanism may be used to occlude the drain tube. For example, the clamp mechanism may be a pinch valve that occludes the drain tube by pinching it so that the lumen through the drain tube is occluded. Another example of a clamp mechanism is a bending or kinking clamp mechanism that bends or kinks the drain tube so that the lumen through the drain tube is occluded. For example, the housing may have one or more movable regions that can be moved with respect to each other so that when the drain tube is secured within the housing, the tube can be bent or kinked by moving a first region of the housing with respect to a second region of the housing. In some variations, the different regions of the housing may be secured together (e.g., hinged). The clamp mechanism may also be configured to occlude the bypass lumen. In some variations, the same clamp mechanism may be used to occlude both the bypass lumen and the drain tube of the catheter.

The device may also include a selector configured to control the operation of the clamp mechanism. In some variations, the selector is attached to the drain tube housing. The operation of the device may be coordinated or at least partially controlled by a selector (or selectors) that controls the operation of the clamp mechanism. In some variations, the selector also controls or coordinates delivery of the bolus of fluid before measuring IAP (e.g., by controlling the fluid infuser and/or the fluid source). The selector may therefore be used to coordinate the measurement of IAP. The selector may be used to open or close (occlude) the catheter drain tube, and/or open and close the bypass lumen or a fluid pathway in connection with the bypass lumen (permitting delivery of fluid into the catheter and/or measurement of IAP).

Any appropriate selector may be used. Examples of selectors include knobs, buttons, dials, sliders, switches, toggles, and levers. The selector may include settings for occluding the catheter drain tube and/or for occluding the bypass lumen. One or more indicators may be included as part of the device, indicating the operation of the device. For example, the device (e.g., the selector and/or housing) may indicate whether the catheter drain tube is occluded by the clamp mechanism. An indicator may be a visual indicator. For example, an indicator may be a color indicator.

The device may also be labeled, or otherwise include instructions. For example, the device may include instructions printed on the body of the device, indicating the order of use, or how to control the device. In some variations, the device may be positioned and secured with respect to the patient or to the patient's bed. The device may include one or more holdfasts for attaching the device to the catheterized patient. Examples of holdfasts may include straps, belts, adhesives, clamps, ties, etc. The holdfast may be cushioned or padded, and may have a shape that conforms to the patient or a portion of the patient (e.g., the patient's leg).

Some variations of the devices described herein are devices for measuring intra-abdominal pressure from a patient that include a bypass lumen configured to fluidly connect to a pressure transducer for measuring intra-abdominal pressure, a sampling port connector in fluid connection with the bypass lumen (the sampling port connector configured to be removably attached to the sampling port of the urinary catheter system to form a fluid connection between the urinary catheter system and the bypass lumen), a housing configured to at least partially enclose a portion of the drain tube of the urinary catheter, a fluid reservoir within the housing (wherein the fluid reservoir is in fluid communication with the bypass lumen), a fluid infuser configured to apply fluid from the fluid reservoir into the urinary catheter, and a clamp mechanism at least partly within the housing, the clamp mechanism configured to controllably occlude the lumen of the urinary catheter system drain tube. The devices described herein are typically to be used with a patient that has already been catheterized with a urinary catheter system that has a sampling port and a drain tube.

The devices described herein may also include a selector configured to control the clamp mechanism and the fluid infuser so that the drain tube may be occluded while applying fluid into the urinary catheter. Furthermore, these devices may include any of the features already described.

Some variations of the devices described herein are devices for measuring IAP that include a bypass lumen configured to fluidly connect to a pressure transducer for measuring intra-abdominal pressure, a sampling port connector in fluid connection with the bypass lumen (wherein the sampling port connector is configured to be removably attached to the sampling port of the urinary catheter system to form a fluid connection between the urinary catheter system and the bypass lumen), a housing configured to at least partially enclose a portion of the drain tube of the urinary catheter system and a portion of a the bypass lumen, a clamp mechanism at least partly within the housing (wherein the clamp mechanism configured to controllably occlude the lumen of the urinary catheter system drain tube and the bypass lumen), and a selector configured control the operation of the clamp mechanism.

Also described herein are systems to measure intra-abdominal pressure that include a catheter having a first lumen in fluid communication with a sampling port, a urinary catheter system bypass device configured to connect to the sampling port, a fluid infusion device, and a pressure transducer, wherein the fluid infusion device and the pressure transducer are in fluid communication with the first lumen of the catheter through the bypass lumen of the urinary catheter system bypass device. The urinary bypass device typically includes a bypass lumen configured to fluidly connect to a pressure transducer for measuring intra-abdominal pressure, a drain tube housing (configured to at least partially enclose a portion of the drain tube of the urinary catheter system), and a clamp mechanism in communication with the drain tube housing, wherein the clamp mechanism is configured to controllably occlude the lumen of the urinary catheter system drain tube.

As described above, the fluid infusion device may be a pump or a syringe, and the pressure transducer may be attached to the syringe. Any appropriate clamp mechanism may be used, including a pinch valve or pinch vice. In some variations, the system also includes an output device connected to the pressure transducer to provide a pressure measurement to a user, or for storage or transmission of pressure measurements.

The urinary catheter system bypass device may also include an auto valve configured to connect to the sampling port of the catheter, and the bypass lumen may include a fluid injection line. Thus, a fluid injection line may be a fluid pathway that is in fluid connection with the bypass lumen. The system (particularly the urinary catheter system bypass device) may also include a fluid infusion pathway in fluid connection with the bypass lumen. A fluid source may also be included and configured to communicate with the fluid infusion pathway. In some variations, the bypass lumen includes an auxiliary sampling port.

Any of the clamp mechanisms described herein may be used as part of the system for measuring IAP. For example, the urinary catheter system bypass device may be configured so that the clamp mechanism is a bend clamp that is configured to occlude the catheter drain tube by bending the catheter drain tube. A bend clamp may include a flexible arm configured so that bending the bend clamp presses the flexible arm into the tube, obstructing fluid flow. In some variations, the clamp mechanism includes a bottom support member and a top attachment member that together connect the clamp mechanism to the tube.

Also described herein are kits for measuring intra-abdominal pressure that include any of the devices (or systems) for measuring IAP described herein. These kits may also include tubing having a lumen for connection to the urinary catheter system bypass device. In some variations, these kits also include instructions. Kits may be sterile or sterilizable, and may be packaged.

Also described herein are methods of measuring intra-abdominal pressure without breaking a closed catheter system. A closed catheter system typically includes a urinary catheter system having a sampling port and a drain tube. In general, these methods may include the steps of inserting the drain tube of the urinary catheter system into the drain tube housing of a urinary catheter system bypass device, attaching the urinary catheter system bypass device to the sampling port of the urinary catheter, occluding the drain tube of the urinary catheter, infusing fluid into the urinary catheter, and detecting intra-abdominal pressure. The urinary catheter system bypass device may be any of the devices described above, including devices having a sampling port connector fluidly connected to a bypass lumen, a drain tube housing (that is configured to at least partially enclose a portion of the drain tube of the urinary catheter), and a clamp mechanism in communication with the drain tube housing (where the clamp mechanism is configured to controllably occlude the lumen of the urinary catheter system drain tube).

In some variations, the method for measuring IAP also includes opening the drain tube of the urinary catheter. The step of opening the drain tube may also include occluding the bypass lumen. In some variations, the step of inserting the drain tube of the urinary catheter system into the drain tube housing includes separating a first region of the drain tube housing from a second region of the drain tube housing, and inserting the drain tube between the first and second regions of the drain tube housing. The first and second regions of the housing may then be joined so that the drain tube is secured between them within the housing. The step of occluding the drain tube of the urinary catheter system may include activating the clamp mechanism of the urinary catheter system bypass device to occlude the drain tube. For example, the step of occluding the drain tube may involve pinching the drain tube, bending (or kinking) the drain tube, etc.

These and other embodiments, features and advantages will become more apparent to those skilled in the art when taken with reference to the following more detailed description of the invention in conjunction with the accompanying drawings that are first briefly described.

BRIEF DESCRIPTION OF THE DRAWINGS

FIG. 3A shows a perspective view of one embodiment of a device for measuring IAP as described herein.

FIGS. 3B and 3C illustrate operation of the clamp mechanism of the device shown in FIG. 3A.

FIG. 5 shows one embodiment of a device for measuring IAP attached to a catheter system.

FIG. 18A shows another embodiment of a device for measuring IAP attached to a catheter system.

FIG. 18B show the device of FIG. 18A occluding the drain tube of the catheter system.

FIGS. 21A and 21B show one embodiment of a device for measuring IAP having an integrated fluid infuser, as described herein.

FIGS. 23A-23D show a perspective, top, side, and cross-sectional views, respectively, of a device for measuring IAP, as described herein.

FIGS. 24A-24C illustrate the operation of one embodiment of a device for measuring IAP.

FIG. 25A shows a perspective view of a device for measuring IAP similar to the device shown in FIG. 24A-24C.

FIG. 29A shows a perspective view of another embodiment of a device for measuring IAP partly attached to a catheter system.

FIGS. 29B and 29C show top and side views of the device for measuring IAP shown in FIG. 28A.

FIGS. 29D-29F illustrate operation of the clamp mechanism of the device shown in FIGS. 29A-C.

FIGS. 30B, 30C and 30D show top, side and another side views of the device of FIG. 30A.

FIGS. 30E and 30F illustrate different positions of the selector for the device shown in FIG. 30A.

FIG. 33A shows a perspective view of a device for measuring IAP attached to a urinary catheter system as described herein.

FIGS. 33B and 33C show cross-sectional views of the device shown in FIG. 32A.

FIG. 43A shows a schematic of an embodiment of an IAP monitoring system similar to that of FIG. 41.

FIG. 43B shows one example of a pressure transponder for the device shown in FIG. 43A.

DETAILED DESCRIPTION OF THE PREFERRED EMBODIMENTS

Figure 1A:
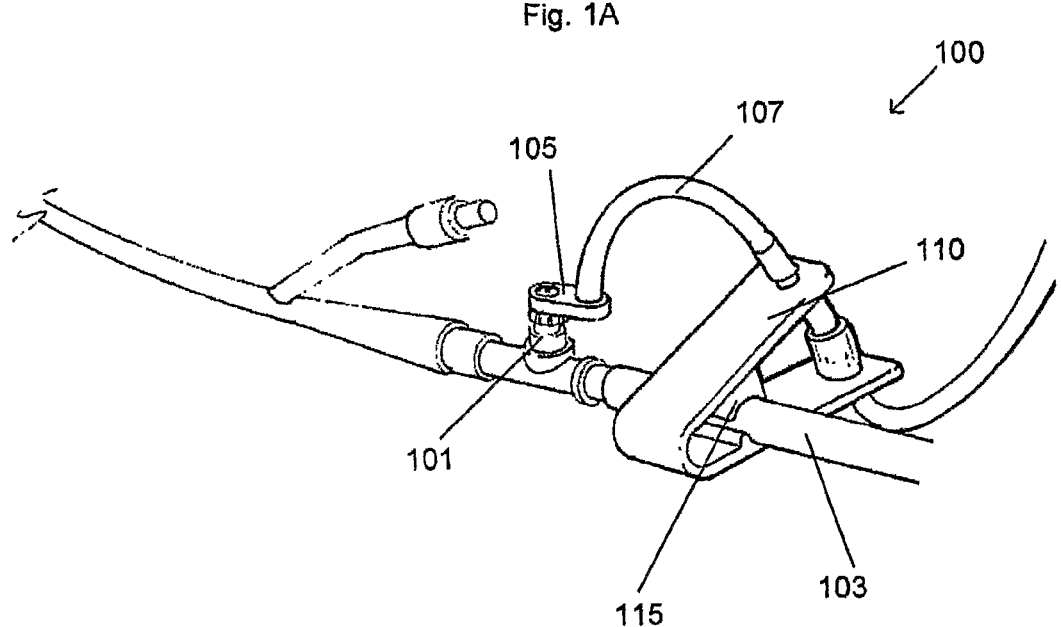
FIG. 1A shows a perspective view of one embodiment of a device for measuring IAP as described herein.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

While the variations herein are described with respect to certain connections, such as a threaded connection between an auto valve and a sampling port, other types of connections are also possible and are within the scope of the invention, such as clamping connections, interference fit connections, etc. Also, as used herein the term "IAP monitoring system" refers to any system that provides one or more intra-abdominal pressure measurements and the terms "measured" and "monitored" are used interchangeably to indicate that one or more pressure readings are provided over any period of time. Further, the terms "urinary catheter" and "Foley catheter" are used herein to refer to any catheter, conduit, or like device configured to drain urine from a bladder of a patient. A patient may be any subject who can benefit from the devices and methods described herein, including human and animal subjects. Patients are not limited to subjects undergoing medical treatment.

Intra-abdominal pressure (IAP) may be measured by measuring the pressure of fluid contained within a patient's bladder. For example, a urinary catheter system may be used to access the patient's bladder. If the bladder is prevented from emptying (e.g., by occluding the drainage port of the catheter), the pressure of fluid within the bladder may be measured, and this pressure may reflect the IAP. The amount of fluid within the bladder (and catheter) to permit accurate IAP measurement may vary by patient, but is typically within about 10-100 ml (e.g., 50 ml). Thus, fluid may be added through the catheter before measurement is taken. Fluid may be added as a bolus or gradually. Any appropriate fluid may be added, e.g., saline, air, etc. For example, using air to fill the bladder is a clinically viable option, as the pressure of air may be used to determine IAP, and the air-filled bladder may be used in imaging modalities as well, as is known in the art.

The IAP measurement devices, systems and methods described herein may allow a practitioner (e.g., doctor, nurse, technician, etc.) to measure and/or record IAP from a patient using a urinary catheter. Any of the IAP measurement devices described herein may be used as part of a system or kit for measurement of IAP.

In general, the devices for measuring IAP described herein may be thought of as either urinary catheter system bypass devices ("bypass devices") or as urinary catheter system integrated devices ("integrated devices"). This distinction refers to how the TAP measurement device connects with the urinary catheter. Integrated IAP measuring devices (e.g., urinary catheter system integrated devices) typically connect to the urinary catheter system drainage port. Integrated IAP devices may include a valve (e.g., a stopcock, pinch valve, etc.) that occludes drainage, preventing drainage from the bladder through the catheter. Thus, integrated IAP devices include a feature built into the catheter system that specifically allows IAP measurement. Since all drainage from the bladder must pass through the integrated IAP device, a urine waste container (e.g., a urine collection bag) is usually attached to a proximal end of the integrated IAP device. Thus, urinary catheter system integrated devices may be attached to the catheter before it is inserted into a patient. FIGS. 34-40 show examples of urinary catheter system integrated devices, while FIGS. 1-32B show examples of bypass-type devices.

Urinary catheter system bypass devices typically connect to ports other than the drainage port of a urinary catheter, so that the drainage port of the catheter is connected to a drain tube and collection container. For example, urinary catheter system bypass devices may connect to a sampling port of a urinary catheter. In some variations an IAP measurement device is connected to an inflation port. Bypass devices typically get added to existing in-dwelling catheter systems. Thus, bypass IAP measurement devices may be used with a catheter system that has already been inserted into a patient without disrupting the closed urinary catheterization system and may also be removed without opening the urinary catheter system. Urinary catheter system bypass devices typically include a clamp mechanism for occluding the drain tube of the urinary catheter system from the outside of the urinary catheter system drain tube.

As mentioned above, bypass IAP measurement devices may be used with indwelling urinary catheter systems. Indwelling urinary catheter systems include urinary catheter systems that have already been inserted into a patient (e.g., a catheterized patient). Indwelling urinary catheter systems typically include a drain tube through which urine drains from the bladder and through the catheter into a collection or waste container. Some bypass-type IAP measurement devices are adapted to be used with generic catheters (including commercially available catheters such as 2-way Foley catheters) that have been inserted into the patient. Because the bypass IAP measurement devices connect to preexisting ports on a catheter (e.g., a sampling port), they do not break the indwelling closed catheter system.

Any of the IAP measurement devices may be configured as on-demand or automatic IAP measurement devices. For example. An IAP measurement device may be manually controlled to measure IAP, as exemplified in many of the figures and described below (e.g., FIGS. 1A-30). In some embodiments the IAP device may automatically determine IAP. For example, an IAP measurement device and/or system may include timing and control logic configured to sample IAP automatically. In some variations, IAP measurement may be intermittent. For example, measurement may be taken one or more times, or taken multiple times with any appropriate time interval between measurements. Thus IAP measurement may be taken at various times (e.g., every 10 minutes, every 20 minutes, every 30 minutes, every hour, etc.). Any appropriate interval may be set. FIGS. 31 and 32, described more fully below, illustrate embodiments including automatic measurement. In some variations, IAP measurement may be taken continuously.

The distinction between urinary catheter bypass devices and urinary catheter integrated devices is not a strict one, and embodiments of both bypass and integrated IAP devices are shown herein. Features or aspects of bypass devices may be included as part of an integrated device, and features or aspects of integrated devices may be part of a bypass device. Furthermore, some embodiments of the IAP measurement devices described herein are neither bypass IAP devices nor integrated IAP devices (e.g., FIG. 33).

Urinary Catheter System Bypass Devices

Typical urinary catheter system bypass devices for measuring IAP from a patient catheterized with a urinary catheter system include a port connector, a bypass lumen, a drain tube housing, and a clamp mechanism. In general, bypass devices are fluidly connected to the catheter system through a port connector that connects the bypass lumen of the device to a non-drain port of the catheter. Examples of non-drain ports include a sampling port, an inflation port, and/or a secondary port (e.g., a 3-way Foley catheter). The bypass lumen is configured to form a fluid pathway through which fluid (e.g., saline) may be added to the catheter in order to make a pressure measurement. The bypass lumen is also configured to connect via a fluid pathway to a pressure transducer to measure IAP. The drain tube housing at least partially encloses a portion of a drain tube from the catheter. The clamp mechanism controllably occludes the lumen of the drain tube.

FIGS. 1A-29E (described in more detail below) illustrate embodiments of IAP measurement devices and systems that are adapted for use with a urinary catheter system having a sampling port to which the devices can attach. Urinary catheter systems including sampling ports are commercially available, and are well known to one skilled in the art. As used herein, the phrase "urinary catheter system" may include any appropriate urinary catheter (such a Foley catheter), a drain tube, and a collection chamber (such as a urine collection bag). A sampling port may be included as part of a catheter system. For example, a sampling port may be part of a catheter, or it may be part of a drain tube and/or a combined drain tube and sample bag. A urinary catheter system may be connected (e.g., the component parts may be connected) to form a "closed" urinary catheter system.

FIG. 1A illustrates one variation of a urinary catheter system bypass device. In FIG. 1A, the device for measuring IAP is adapted for use with a patient catheterized with a urinary catheter system. A portion of the catheter system, including the sampling port 101 and the drain tube 103 are shown. A device for measuring IAP 100 is shown connected to the urinary catheter system at the sampling port 101. The device includes a sampling port connector 105 that is engaged with the sampling port of the urinary catheter system. The sampling port connector may be engaged in any appropriate manner with the sampling port. In particular, the sampling port connector is releasably connected to the sampling port. For example, the sampling port connector may include a luer lock connector that engages a luer lock on the sampling port. Either (or both) the sampling port and the sampling port connector may include valves (e.g., displaceable valves) to prevent flow through them unless they are engaged. The sampling port and sampling port connector may also be secured together (e.g., locked) by a sampling port lock. For example, the sampling port connector may include a threaded (e.g., screw-in) lock for securing the connector to the sampling port. In some variations, the sampling port or the sampling port connector comprises an EZ-LOK™ valve or connector, as described herein. Any appropriate sampling port may be used. For example, the sampling port may comprise a pierceable split septum.

Figure 1B:
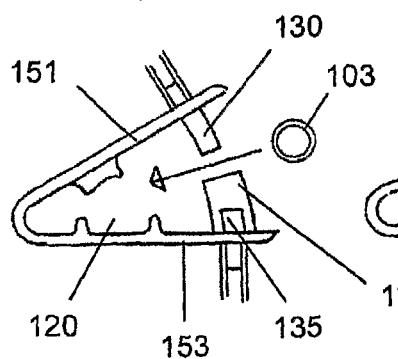
FIGS. 1B-1D illustrate operation of the clamp mechanism of the device shown in FIG. 1A.
Figure 1C:
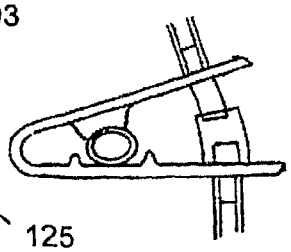
Figure 1D:
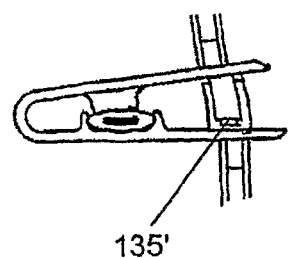

In general, the sampling port connector is fluidly connected with the bypass lumen of the device. The bypass lumen may be fluidly connected to either (or both) a pressure transducer and/or a fluid infuser, allowing measurement of IAP. The bypass lumen may therefore form a fluid pathway with both the pressure transducer and the fluid infuser. In FIG. 1A, the bypass lumen is contained within a bypass tubing 107 that is interrupted by the drain tube housing 110, preventing flow therethrough. The drain tube housing 110 partly encloses the drain tube 103 portion of the urinary catheter system. In the embodiment of FIG. 1A, a region of the drain tube housing 110 is also configured as a clamp mechanism 115, so that (by closing the upper and lower "arms" of the drain tube housing) the clamp mechanism 115 compresses the drain tube 103, occluding the drain tube lumen and preventing flow therethrough, as illustrated in FIGS. 1B-1D. In general, the drain tube housing is configured to at least partly enclose a portion of the drain tube of the urinary catheter system so that it can be occluded. The drain tube housing may also be referred to as simply a "housing."

In FIG. 1B, the drain tube housing is open, and the upper 151 and lower 153 regions (shown here as arms) of the drain tube housing are separated, and can permit a drain tube 103 to be positioned therebetween so that the drain tube can sit in a channel 120 formed within the drain tube housing. The upper 151 and lower 153 regions of the channel form a clamp mechanism 115 that may be securable in either the open (e.g., FIG. 1B) or closed (e.g., FIG. 1D) positions. For example, the clamp mechanism may be secured in position by a lock (e.g., a snap, clip, clamp, button, tie, or the like). In the embodiment shown in FIGS. 1A-1D, the clamp is secured by the interaction between the upper engagement region 130 and lower engagement region 125, as described below.

In FIGS. 1A-1D, flow through the bypass lumen is also controlled by the clamp housing. In this example, the bypass tubing 107 (through which the bypass lumen runs) is attached to the housing 110, and the bypass lumen is interrupted. The bypass lumen is connected to an upper engagement region 130 and a lower 125 engagement region that are separable, but may engage to form a passageway. The lower engagement region 125 also includes a valve 135 that is closed when the upper and lower engagement regions are not engaged (as shown in FIGS. 1B and 1C). When the upper and lower engagement regions are separated (not engaged, as shown in FIG. 1B), flow through the bypass lumen is prevented. When the upper and lower engagement regions are engaged (as shown in FIG. 1D), flow is permitted past the valve 135 and through the bypass lumen.

Thus, the clamp housing may control the operation of the clamp mechanism. When the upper and lower regions of the clamp housing are compressed together as shown in FIG. 1D, the clamp mechanism occludes flow through the drain tube, and the upper and lower engagement regions are engaged, displacing the valve and permitting flow through the bypass lumen. Thus, fluid can be applied through the bypass lumen into the catheter system (and bladder) and IAP can be measured based on the pressure of the fluid in the bypass lumen, since this fluid is in communication with fluid in the bladder and with the pressure sensor. The clamp mechanism may then be opened to permit flow through the drain tube 103 of the catheter system, and prevent flow through the bypass lumen by moving the arms of the housing apart, as shown in FIG. 1B.

Figure 2A:
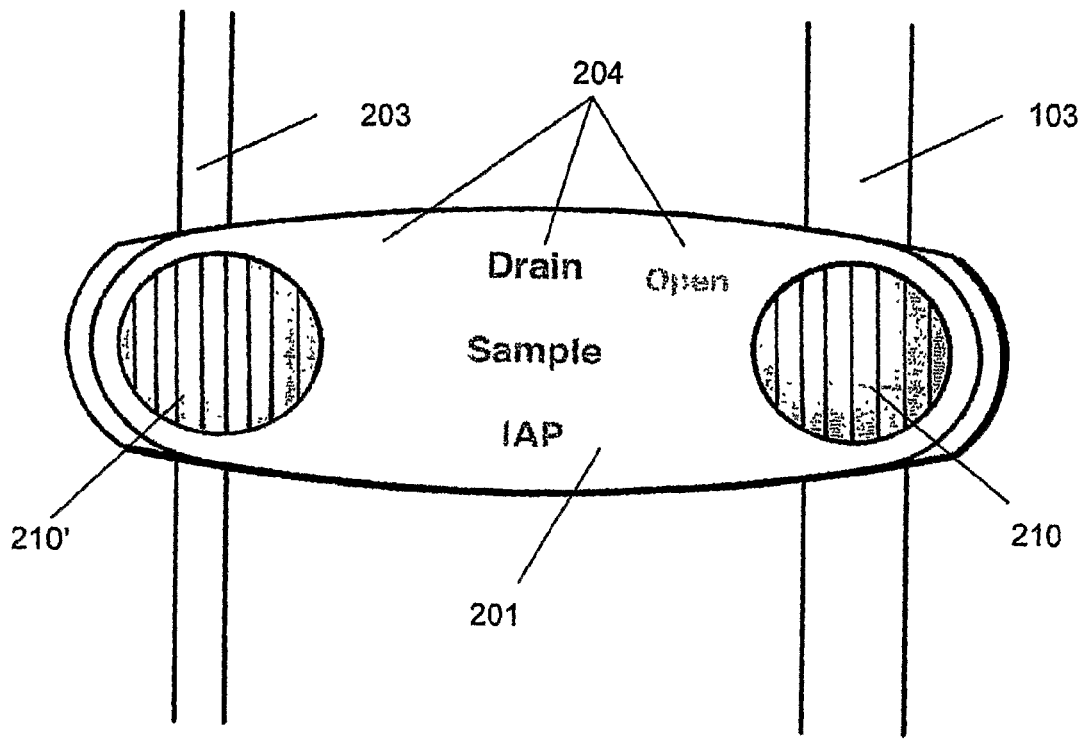
FIGS. 2A and 2B show top and perspective views, respectively, of one variation of a housing region of a device for measuring IAP.
Figure 2B:
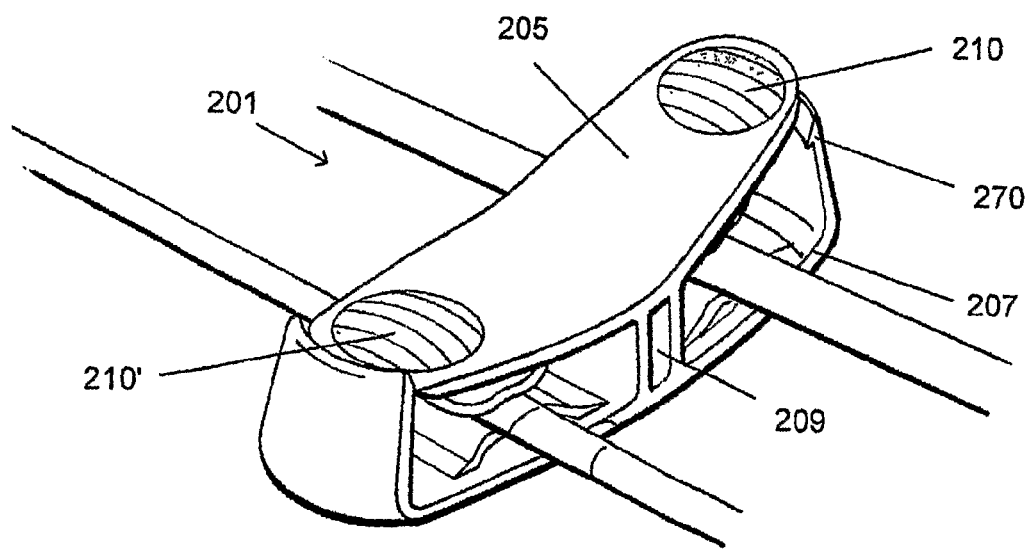

FIGS. 2A and 2B show another variation of a device for measuring IAP similar to the device shown in FIGS. 1A-1D. The drain tube housing 201 shown in FIG. 2A encloses the drain tube 103 as well as a tube (e.g., a bypass tube) through which the bypass lumen 203 runs. In FIGS. 2A and 2B, the clamp mechanism is also a pinch valve that can pinch the drain tube 103, or the bypass tube 203 to occlude flow through the tube. In general, a pinch valve occludes flow through a tube by pinching the tube closed. The drain tube housing 201 shown in FIGS. 2A and 2B also has a first (e.g., upper) region 205 and a second (e.g., lower) region 207 that can be moved relative to each other to open and permit the drain tube 103 or bypass tube 203 to be positioned within the channels through the housing. The upper and lower regions of the housing shown in FIG. 2B are hinged 209 at a centerline of the housing so that they can rock from side to side. A portion of the upper region 205 and the lower region 207 forming the drain tube channel and the bypass tube channel are configured as a clamp mechanism. Thus, as one side of the device is "opened," the other side is closed (occluding flow through a tube).

Figure 2C:
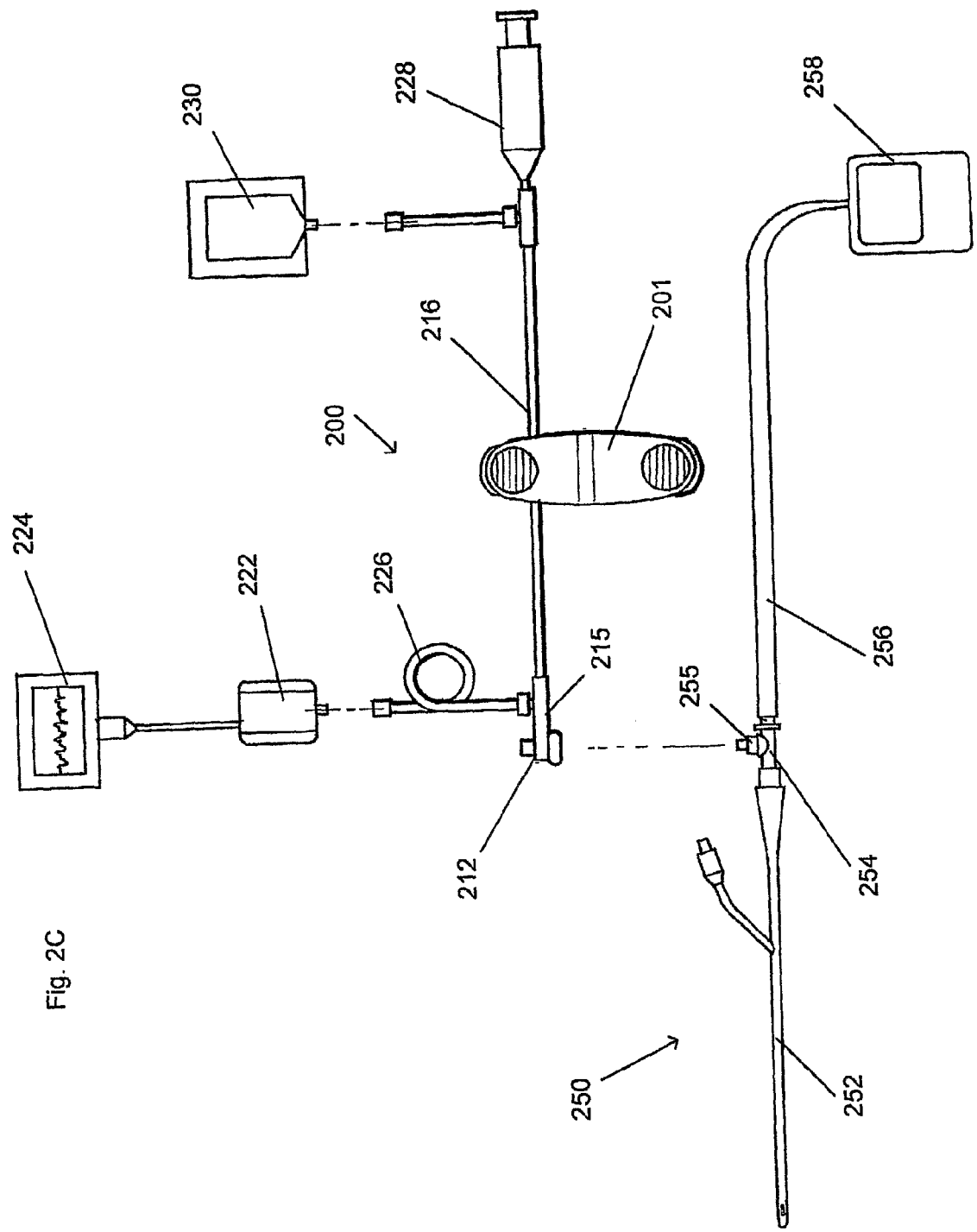
FIG. 2C shows a system for measuring IAP incorporating the device shown in FIGS. 2A and 2B.

The drain tube housing shown in FIGS. 2A and 2B may be part of a device (and part of a system) for measuring IAP from a closed urinary catheter system. FIG. 2C shows this housing as part of an IAP device and system. The housing 201 is part of the IAP measurement device 200 that also includes a sampling port connector 212 that is fluidly connected to a bypass lumen. The bypass lumen (not visible in FIG. 2C) passes through the bypass tube 215.

The device for measuring IAP 200 shown in FIG. 2C is also adapted to include additional components that may be part of the device. For example, the device for measuring IAP 200 may also include a pressure transducer 222 that is connected to a monitoring device 224 and/or a recording or transmitting device (not shown). The pressure transducer detects the pressure of fluid within the bypass lumen, which is proportional (or equivalent to) the pressure within the bladder and therefore the IAP. The pressure transducer is connected to the bypass lumen by a first fluid pathway through the lumen of a pressure transducer tube 226. The first fluid pathway connects to the distal region of the bypass lumen. A second fluid pathway 216 is linked to a fluid infuser 228 and is also connected to the bypass lumen distal to the first fluid pathway. In FIG. 2C the fluid infuser 228 may be filled with fluid from a fluid source 230, shown here as a fluid bag. One-way valves may be used to fill the fluid infuser 228 from the fluid source 230. One-way valves prevent backflow between the fluid source and the fluid infuser, and allow refilling of the fluid source so that multiple IAP measurements may be taken. An example of one-way valves configured in this way may be found in U.S. patent application publication number 2006/0058702 to Christensen et al, which is incorporated by reference into this application as if fully set forth herein.

The fluid infuser 228 shown in FIG. 2C is shown as a syringe. In general, any appropriate fluid infuser may be used. For example, a fluid infuser may be a pump (e.g., mechanical pumps, including positive displacement pumps, rotary pumps, reciprocating pumps, etc.). The fluid infuser may apply fluid into the bypass lumen (and thereafter into the catheter system and bladder) quickly (e.g., as a bolus of fluid) or gradually. For example, the fluid infuser may be a saline drip line that is gravity-fed into the bypass lumen when it is desired to apply fluid to measure IAP. As mentioned, a fluid infuser may be included as part of the device for measuring IAP. In some embodiments, the fluid infuser is incorporated as part of the housing. The fluid infuser may be pre-loaded with fluid (e.g., in FIG. 2C the syringe 228 may be pre-loaded). The fluid infuser may also be combined with a fluid source 230 so that the device for measuring IAP can be used multiple times to inject fluid and measure pressure.

FIG. 2C also illustrates a urinary catheter system 250 to which the device for measuring IAP may be connected. The urinary catheter system 250 shown in FIG. 2C includes a Foley catheter 252. The drainage port of the catheter is connected to a drainage connection member 254 having a sampling port 255, and the drainage connection member is connected to a drain tube 256 that is in turn connected to a urine collection bag 258. In operation, the device for measuring IAP 200 is first connected to the urinary catheter system 250. The sampling port connector 212 is attached to the sampling port 255 of the urinary catheter system 250, and the drain tube housing 201 is opened to enclose at least a portion of the drain tube 256. The drain tube 256 may fit into a channel within the drain tube housing 201 by separating the first (upper) region 205 of the housing from the second (lower) region 207 of the housing, allowing the drain tube 256 to be positioned therebetween. Once the sampling port connector is attached, the drain tube 256 may be closed by compressing the clamp mechanism around the drain tube.

The housing shown in FIGS. 2A-2C also includes selectors 210, 210'. In this embodiment, the selectors 210, 210' are buttons on the upper surface of the housing that are depressed in order to open/close either the drain tube or the bypass tube. This embodiment of the selector includes a textured surface (e.g., a "soft-touch" grip) that may help identify the selector, and may make it easier for a practitioner to activate or de-activate the clamp mechanism. In some variations, the selector comprises a lever, a knob, a dial, a slider, a switch, a toggle, etc. The selector shown in FIG. 2A-2C allows simultaneous control of both the drain pathway (through the drain tube) and the bypass pathway (through the bypass lumen) because the clamp mechanism is configured as a dual clamp mechanism. Pushing on the selector above the drain tubing causes the clamp mechanism (a pinch valve) to pinch the drain tube, occluding the lumen of the drain tube. The housing 201 is configured so that closing the drain tube causes the clamp mechanism around the bypass tube 216 to open, opening the bypass lumen so that fluid can be added by the fluid infuser 228 through the sampling port connector 212 and into the catheter system, such that an IAP measurement can be made.

The IAP measurement device shown in FIG. 2A also includes settings or instructions 204 on a face of the housing 201. These settings indicate how the device may be used to operate the device. For example, FIG. 2A shows that the right selector 210 opens the drain tube (e.g., "drain"), and closes the bypass tube ("sample" and "IAP" labels), and the left selector 210' closes the drain tube and opens the bypass tube. The drain tube housing may also be configured so that the drain tube and/or bypass tube must be specifically positioned within the drain tube housing. For example, the channels holding the drain tube housing may only fit either the drain tube or the bypass tube. In the embodiment shown in FIG. 2A the drain tube has a larger diameter than the bypass tube. In some variations, the device may also include one or more indicators that indicate when the drain (or bypass) tube are in the open or closed state.

As mentioned above, a system for measuring IAP may include any of the components described herein, including a device for measuring IAP and a urinary catheter system, or parts of either.

Another embodiment of the device for measuring IAP (similar to the embodiment shown in FIGS. 2A-2C) is shown in FIG. 3A-3C. This embodiment includes a housing 301 that incorporates a clamp mechanism configured as a pinch valve. As with the drain tube housing 201, the drain tube housing 301 is configured to at least partly enclose a portion of both the drain tube 103 and a bypass tube 203. However, in FIG. 3, the selectors 310, 310' are depressions on a butterfly-shaped housing.

In both variations shown in FIGS. 2A-2D and FIGS. 3A-3C, the clamp mechanism may be locked in position by a releasable latch 270, 370 on either side of the housing. The operation of the latch in FIGS. 3A-3C is illustrated by FIGS. 3B and 3C. In FIG. 3B, the drain tube is located in the clamp mechanism of the housing, between the first (upper) region of the housing and the second (lower) region of the housing. The latch 370 projects from the first region and is not engaged with the second region. After the selector above the drain tubing has been pressed, causing the clamp mechanism to pinch the drain tube so that it is occluded, the latch 370 passes though a latch receiving region 372 (shown as an opening) and engages with the second region of the housing. The engaged latch 370 secures the clamp mechanism closed over the drain tube, as shown in FIG. 3C. The latch (similar to the rest of the housing) may therefore be made of a material (e.g., a polymeric material, metal, alloy, etc.), including elastomeric materials, that may be deformed but retain or return to their original shape. The latch may be made of the same material as the housing, or it may be a different material. Furthermore, the latch may be made as an integral part of the housing.

Figures 4A, 4B, 4C:
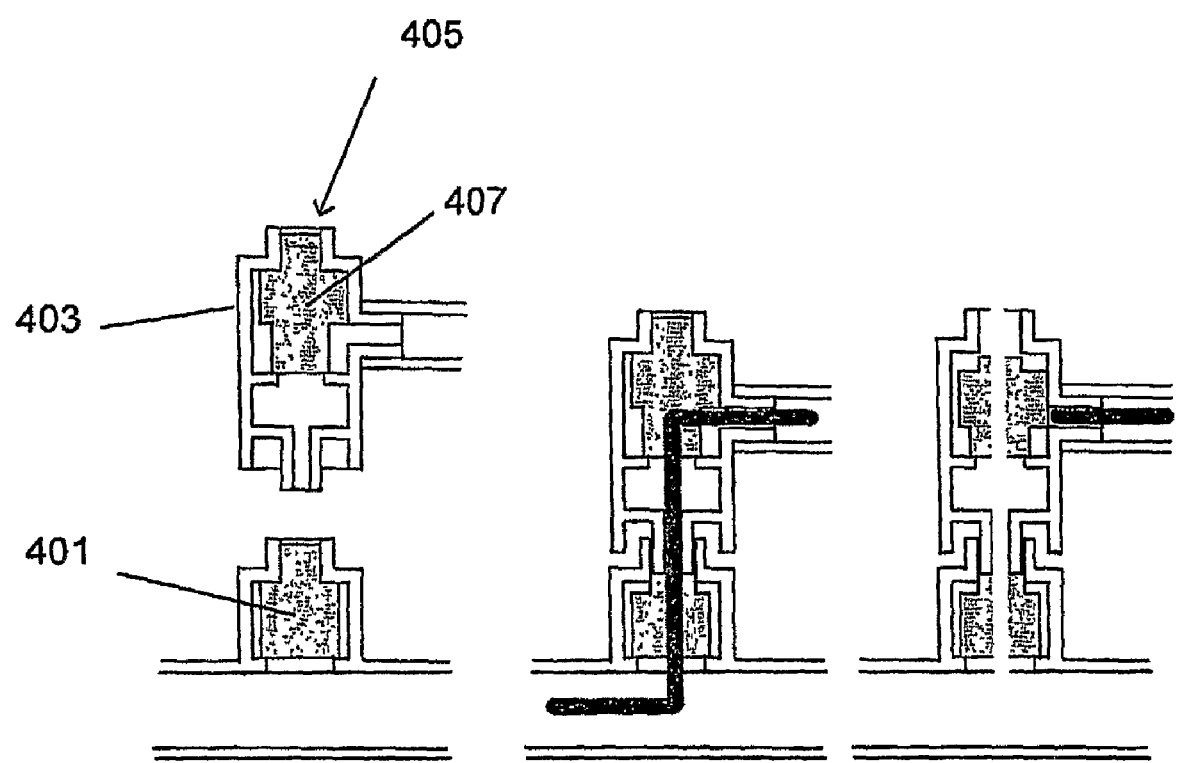
FIGS. 4A-4C illustrate flow through sampling port connector having an auxiliary sampling port, as described herein.

The device shown in FIG. 3A also includes an auxiliary sampling port 320 that is shown as part of the sampling port connector 312. The auxiliary sampling port may allow sampling of urine within the urinary catheter system when the device is attached to the sampling port of the urinary catheter. The auxiliary sampling port may be the same kind of sampling port that is on the catheter, or it may be a different type. For example, the auxiliary sampling port may include an EZ-LOK™ mechanism. In some embodiments, the auxiliary sampling port includes a valve to prevent flow between the urinary catheter system and the device for measuring IAP when the auxiliary sampling port is used. FIGS. 4A-4C illustrate one embodiment of this type of auxiliary sampling port.

FIG. 4A shows a sampling port 401 (e.g., part of urinary catheter system), before a sampling port connector 403 is connected to it. As mentioned above, the sampling port connector may be part of a device or system for measuring IAP. Once the sampling port connector 403 is engaged with the sampling port 401, fluid may flow between the fluid urinary catheter system and the bypass lumen, as shown in FIG. 4B. However, if the auxiliary sampling port 405 is engaged (e.g., by a luer/syringe connection, etc.) the internal valve 407 is displaced, blocking flow from the bypass lumen. This is illustrated in FIG. 4C. In FIG. 4C, only flow between the catheter system and in or out of the auxiliary sampling port is allowed.

FIG. 5 illustrates another embodiment of an IAP monitoring device that is attachable to a pre-implanted and operating Foley catheter system. The device depicted in FIG. 5 includes a drain tube housing (including a clamp mechanism) 512 and a sampling port connector configured as an auto valve 507 that can be positioned over a drain tube 503 of a Foley catheter system. In this embodiment, the drain tube housing 512 and sampling port connector 507 are connected together, and can be positioned proximal of a sampling port 501 of a urinary catheter system that includes an integral valve. The portion of the urinary catheter system shown in FIG. 5 includes a sampling port 501 that is configured as an EZ-LOK™ sampling port. When connected to the sampling port, the insertion member of the auto valve 507 opens the valve member of the sampling port such that fluid communication is possible between a lumen of the Foley catheter and the bypass lumen, so that the bypass lumen is in fluid connection with a lumen of the catheter through the fluid injection line 509 of the auto valve. The drain tube housing 512 in the embodiment of FIG. 5 is positioned over the drain tube 503 adjacent the sampling port 501 and pressed thereover. The housing is sized such that connection to the drain tube in this manner is quite secure, resulting in little, if any, rotation around the tube without greater than normal forces being applied.

In the illustrated embodiment, the drain tube housing 512 includes a clamp mechanism that is configured with a flexible linking member 520 having two arms spaced apart (though certainly more than two arms are also possible) that bend when the auto valve is moved toward the sampling port. In one embodiment, the arms fold into the tube, causing the tube to kink. The flexible linking member arms are attached to both a proximal section of the housing (containing the auto valve 507 and fluid injection line 509) and a distal section of the housing, enabling the proximal section to be folded over the distal section without separating the housing from the drain tube. When a pressure reading is desired, the proximal section of the housing is moved toward the sampling port and connected thereto. This action results in providing fluid communication between the fluid injection line (bypass lumen) and the Foley catheter 500, as well as occluding the drain tube.

In one embodiment, the fluid injection line and sampling port connector are attached to the drain tube housing. In FIG. 5, the clamp mechanism is a portion of the drain tube housing, as described. The fluid injection line may be attached to tubing (fluid injection tubing) that leads to a connector, having one line that leads to a pressure transducer and another line that leads to a fluid source, such as a saline bag. The fluid injection tubing may also be referred to as bypass tubing, which encloses a bypass lumen, as described above. The pressure transducer is connected to a zeroing stopcock and a patient monitor. The line that leads to the fluid source may be referred to herein as the infusion tubing and may act as a conduit for fluid from the fluid source to the fluid injection tubing. Between the fluid source and the infusion tubing is a fluid infuser (e.g., a syringe or other pre-fill chamber that can infuse fluid upon either manual or remote command, etc.) to send a predetermined amount of fluid through the tubing under pressure, or the fluid source could itself send fluid through the tubing under pressure (e.g., pressurized saline bag, etc.). When the clamp mechanism is engaged over the drain tube and connected to the sampling port, a predetermined amount of fluid is sent through the infusion tubing and fluid injection tubing and into the catheter.

Figure 6:
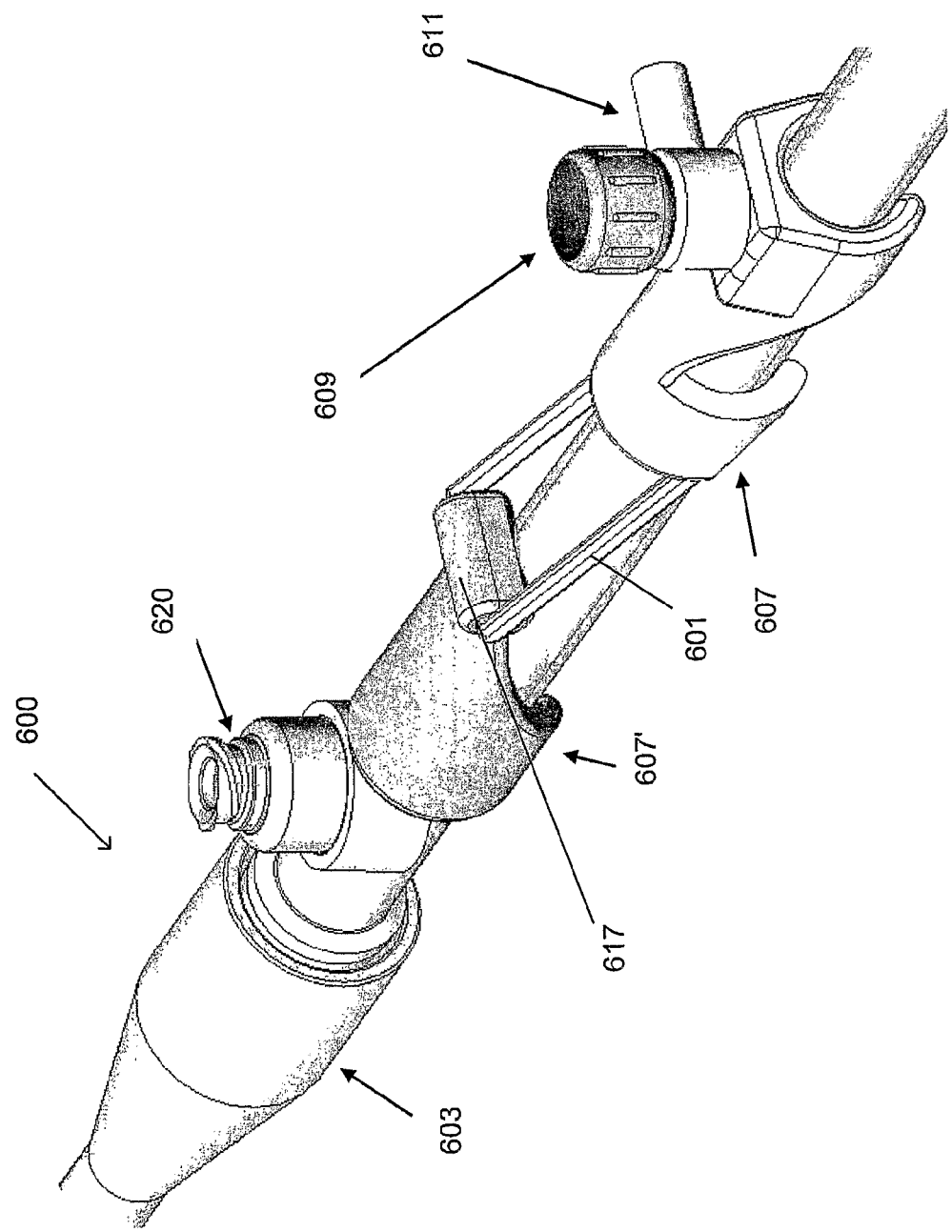
FIG. 6 shows another embodiment of a device for measuring IAP attached to a catheter system.
Figure 7A:
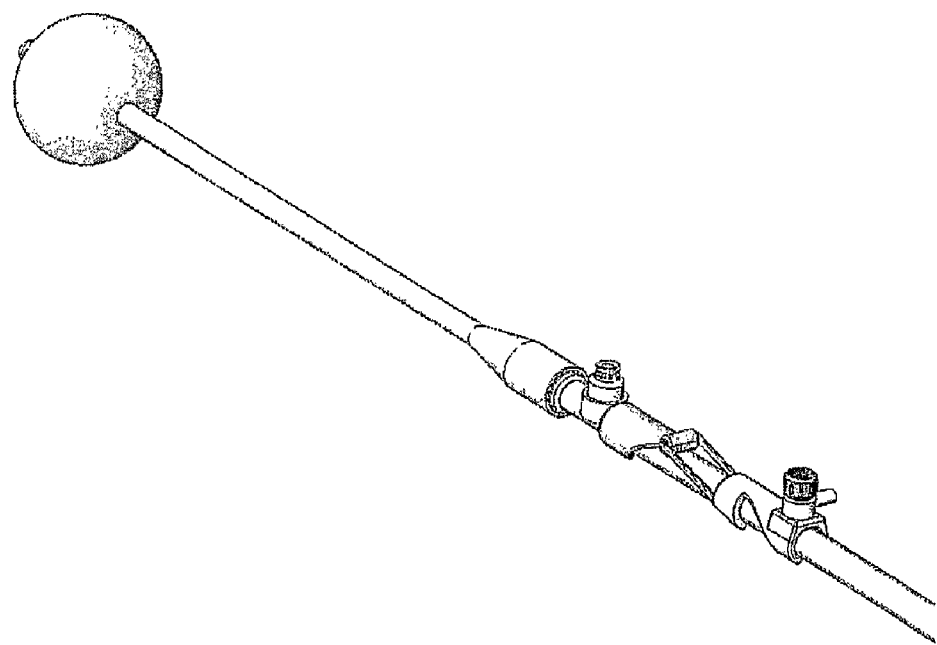
FIGS. 7A and 7B show the IAP monitoring system of FIG. 6 and a urine catheter system in the unactivated (FIG. 7A) and activated (FIG. 7B) state.
Figure 7B:
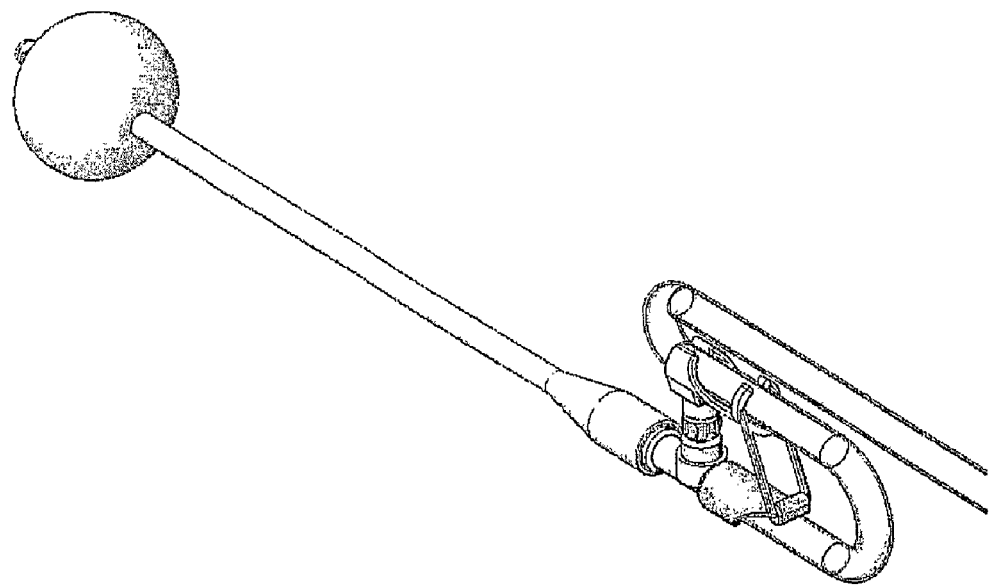

FIGS. 6-7A and 7B illustrate another embodiment of a clamp mechanism for an IAP monitoring system, including a pivoting linking member 601. FIG. 6 shows a clamp mechanism 601 attached to an inserted, working Foley catheter system 600 in a rest state (i.e., prior to activation of the system to take an IAP measurement or for IAP monitoring). The clamp mechanism is connected to a housing 607, 607' that includes a proximal section 607 attached to a sampling port connector configured as an auto valve 609. The sampling port connector includes a fluid injection line 611. The housing also includes a distal section 607' that is positioned adjacent to a connection member 615 of the catheter system. The clamp mechanism 601 is located between the proximal and distal portions of the housing in the rest state. The clamp mechanism includes a hollow piece 617 through which the pivoting linking member 601 is positioned. The hollow piece 617 on the clamp mechanism permits the pivoting linking member to rotate, thereby allowing movement of the proximal section of the housing with respect to the distal section. FIG. 7B illustrates the activated state of the system, after the clamp mechanism has been pivoted to bring the auto valve 609 into locking connection with the sampling port 620. As the clamp mechanism pivots, the drain tube folds, causing a kink in the tube (not shown), which prevents fluid flow therethrough.

Figure 8:
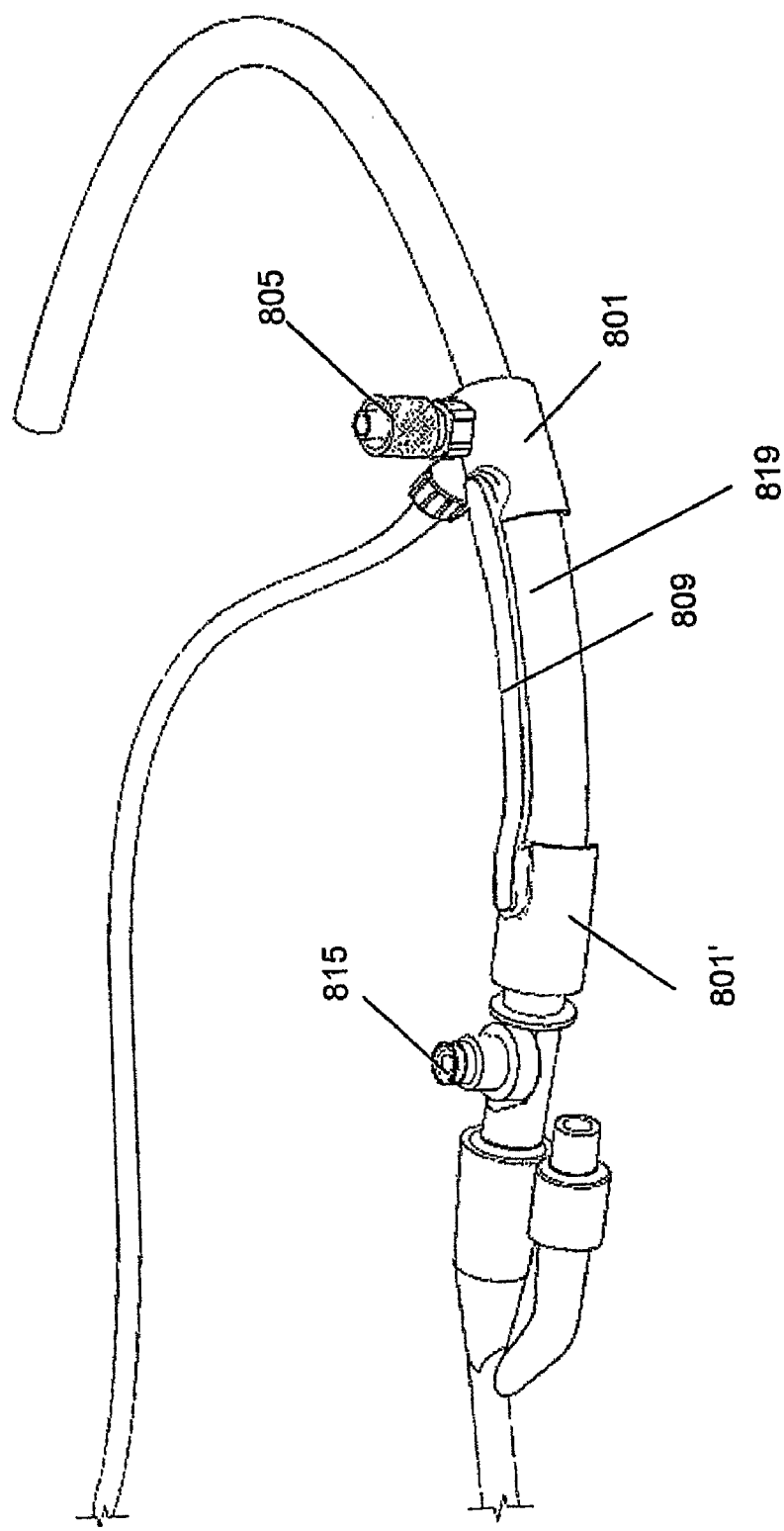
FIG. 8 shows another embodiment of a device for measuring IAP attached to a catheter system.
Figure 9:
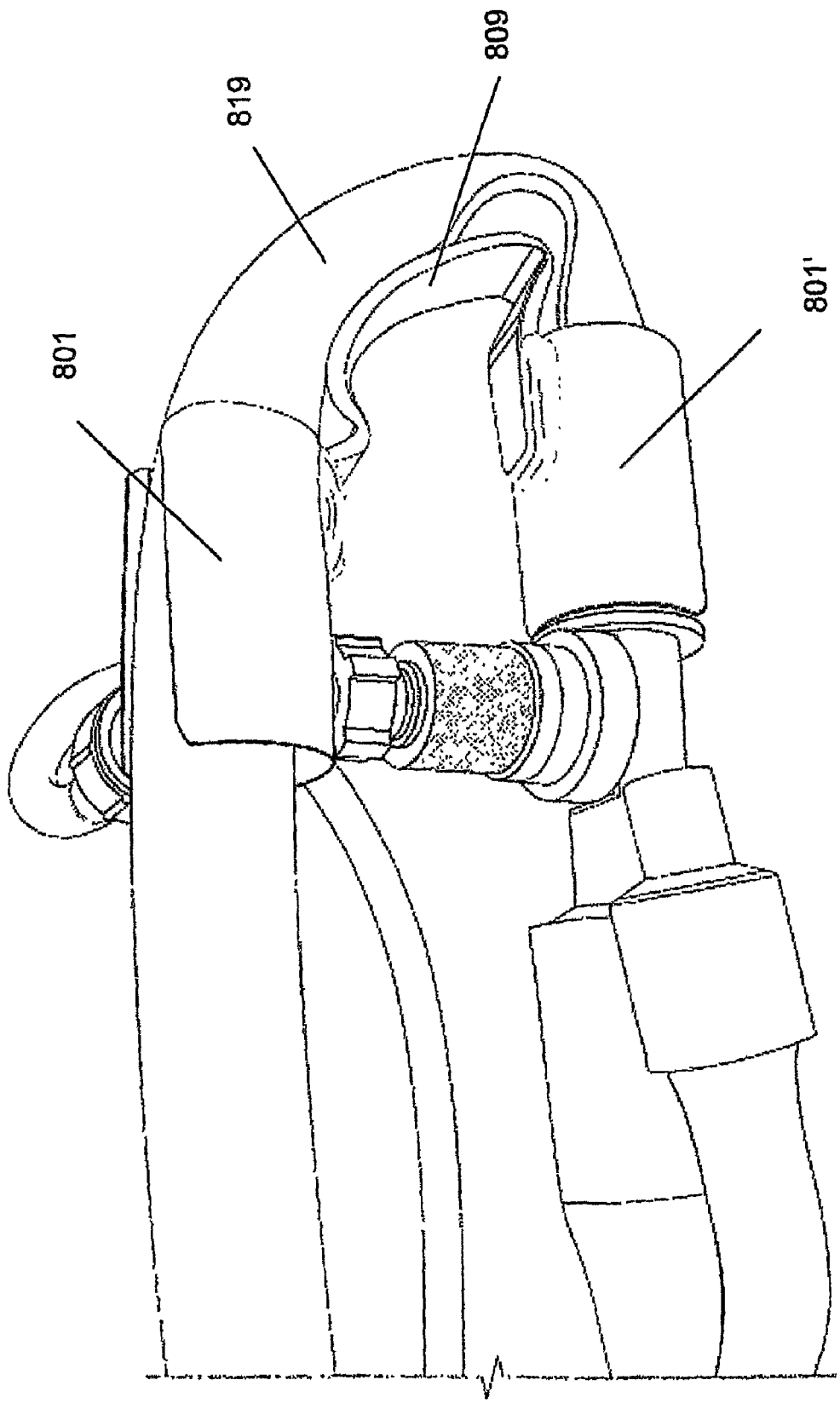
FIG. 9 shows an example of the IAP monitoring device of FIG. 8 attached to a urinary catheter system.

FIGS. 8-9 illustrate another embodiment of a drain tube bending or kinking clamp mechanism, similar to the embodiment shown in FIGS. 6-7B. The housing in this embodiment includes a proximal section 801, containing a sampling port connector including an auto valve 805 and a fluid injection line 807, and a distal section 801' adjacent to a connection member of the catheter system having a sampling port 815. The proximal and distal sections of the housing are connected by a clamp mechanism 809 comprising a single arm flexible linking member. As shown in FIG. 9, when the proximal section of the housing is moved so that the auto valve 805 is connected to the sampling port 815, the proximal section 801 is positioned spatially over the first member and the flexible linking member 809 presses into the drain tube 819, preventing the flow of fluid therethrough.

Figure 10:
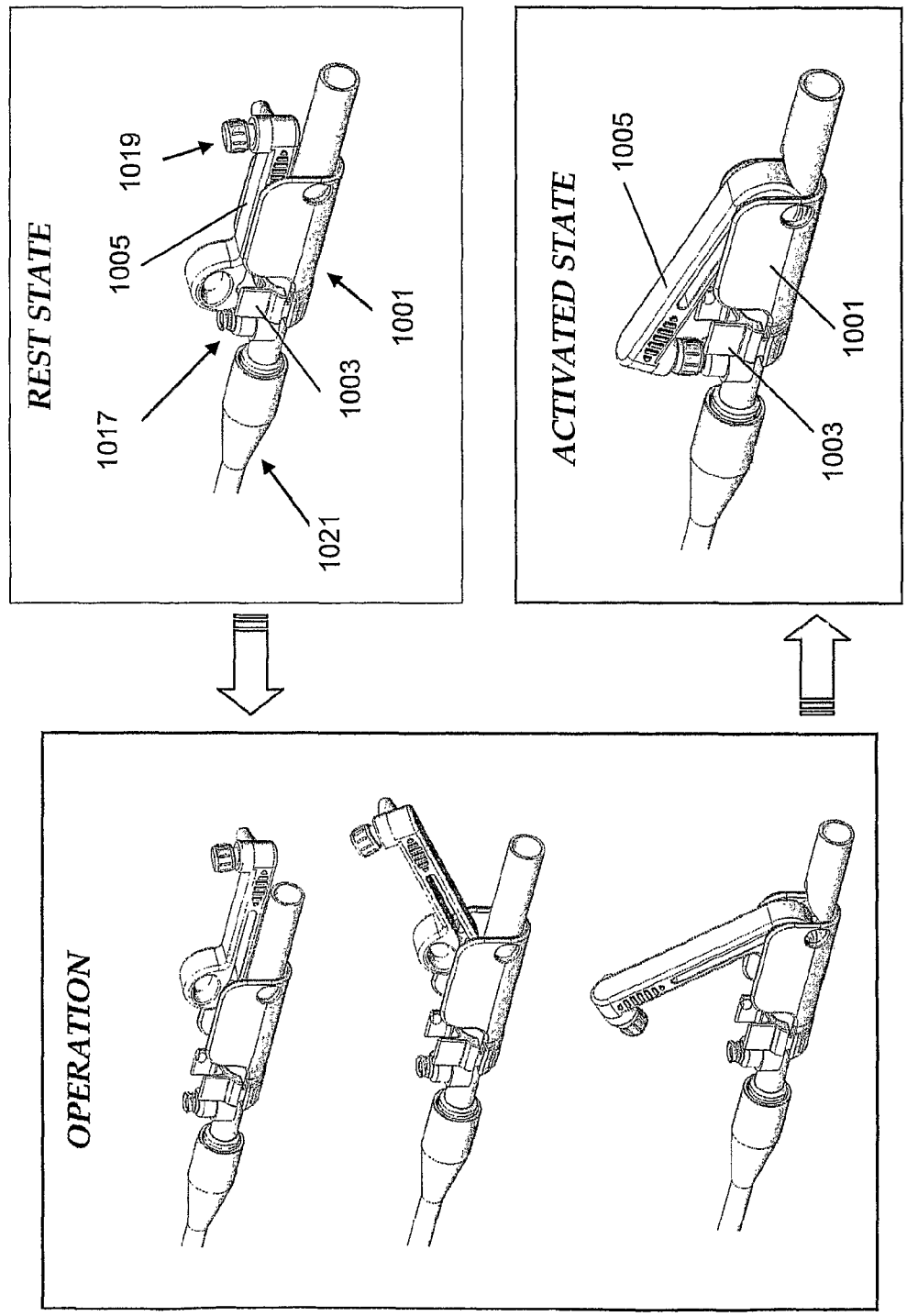
FIG. 10 illustrates a rest state, activated state and operation of a device for measuring IAP according to one embodiment described herein.

FIG. 10 illustrates another embodiment of a housing and clamp mechanism for an IAP monitoring system that is attachable to an inserted, working Foley catheter system. In the picture, the rest state for the system is shown in the upper right hand corner, illustrating the elements of the housing and clamp mechanism. In this embodiment, the housing is formed from a two-piece structure, having a bottom support member 1001 and a top attachment member 1003. The clamp mechanism includes an activation arm 1005 attached to the bottom support member 1001 in sliding, pivoting fashion. The bottom support member 1001 includes a base with two side walls, such that when positioned underneath a drain tube portion of a Foley catheter system, the side walls extend above the drain tube. The side walls have a rail or like member on opposing inner surfaces thereof for engagement with a slot on the activation arm. The activation arm, in addition to having a slotted region to interact with the rail of the bottom support member, includes a sampling port connector similar to the aforementioned embodiments, which when connected to the sampling port enables fluid communication between the fluid injection line (e.g., the bypass lumen) and the Foley catheter (i.e., the activation arm contains an internal lumen connecting the fluid injection line with the auto valve). The activation arm may also include a raised surface on the sides thereof to facilitate the handling and movement thereof by the clinician or user.

The top attachment member 1003 clips to the bottom support member 1001 by inserting legs into slots contained in a proximal portion thereof, as shown in FIG. 10. The top attachment member 1003 also has sidewalls extending above the drain tube, which act to hold the activation arm in a rest position prior to activation of the system. The activation arm 1005 includes a lengthwise slot for engagement with the rail or like member on the inner surface of the bottom support member 1001 to permit sliding and pivoting of the activation arm with respect to the bottom support and top attachment members, which remain stationary after being attached to the drain tube portion of the Foley catheter system. This action is seen in the depiction on the left side of the page entitled, "Operation."

From the rest state (i.e., after the clamp mechanism has been attached to the drain portion of a Foley catheter system), a clinician or user disengages the activation arm 1005 from the top attachment member through a pulling action or by spreading apart the side walls thereof and sliding the activation arm away from the top attachment member and sampling port. As mentioned, the activation arm slides along the side walls of the bottom support member by the interaction between slots in the activation arm and rails or like members on opposing inner surfaces of the side walls. Once the activation arm has been slid along substantially the length of the bottom support member side walls, such that a distal portion of the activation arm is adjacent a proximal end of the bottom support member, the activation arm is pivoted and folded back toward the sampling port as shown. The pivoting action brings the auto valve (shown in FIG. 10 as part of the sampling port connector) into contact with the sampling port and the clinician/user simply threads the auto valve over the sampling port to establish a connection therebetween (and to provide a fluid flow path from the bypass lumen to the Foley catheter). The pivoting action also acts to prevent flow through the drain tube as the distal portion of the activation arm, having an enlarged distal section, presses into the drain tube as shown.

Figure 11A:
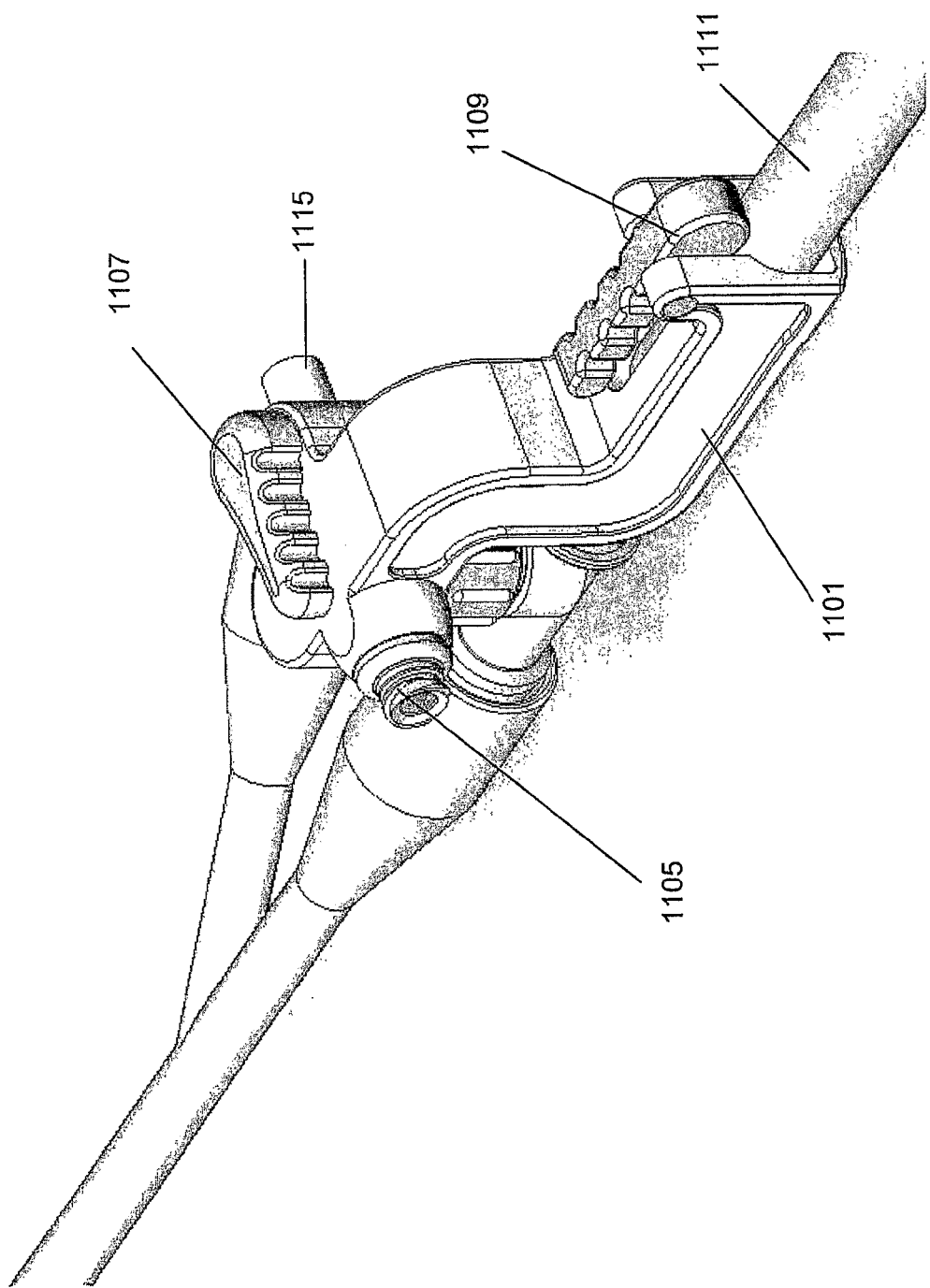
FIG. 11A shows another embodiment of a device for measuring IAP attached to a catheter system.

In the embodiments illustrated in FIGS. 5-10, the sampling port connector must be connected to the sampling port each time an IAP measurement is taken (and disconnected thereafter to permit drainage of urine). FIGS. 11A-12D illustrate another embodiment of a clamp mechanism in which the sampling port connector may be connected to the urinary catheter system for long-term use, or even permanently connected to the sampling port of a urinary catheter system. In FIG. 11A, the drain tube housing 1101 is attached to the connection member of the urinary catheter system such that the sampling port connector (including an auto valve) is connected to the sampling port of the connection member. The sampling port connector is mounted to the housing, and also includes an auxiliary sampling port 1105 on the side. The housing also includes a stopcock valve member 1107 and a clamp mechanism 1109. The stopcock valve member 1107 controls the direction of fluid flow and is shown in the position in which the fluid flow is open to the auxiliary sampling port (i.e., the rest state of the system) so that sampling of urine can take place. In this state, the clamp mechanism is pivoted toward the inserted catheter, which may further indicate that urinary drainage is taking place through the drain tube 1111 over which the housing is positioned. In an activated state, the clamp mechanism 1109 is pivoted away from the catheter, which presses the end of the clamp mechanism 1109 into the drain tube, thereby preventing flow therethrough. Thereafter, the stopcock valve 1107 is turned toward the fluid injection line 1115 to open fluid communication between a bypass lumen (not shown) and the inserted catheter system.

Figure 11B:
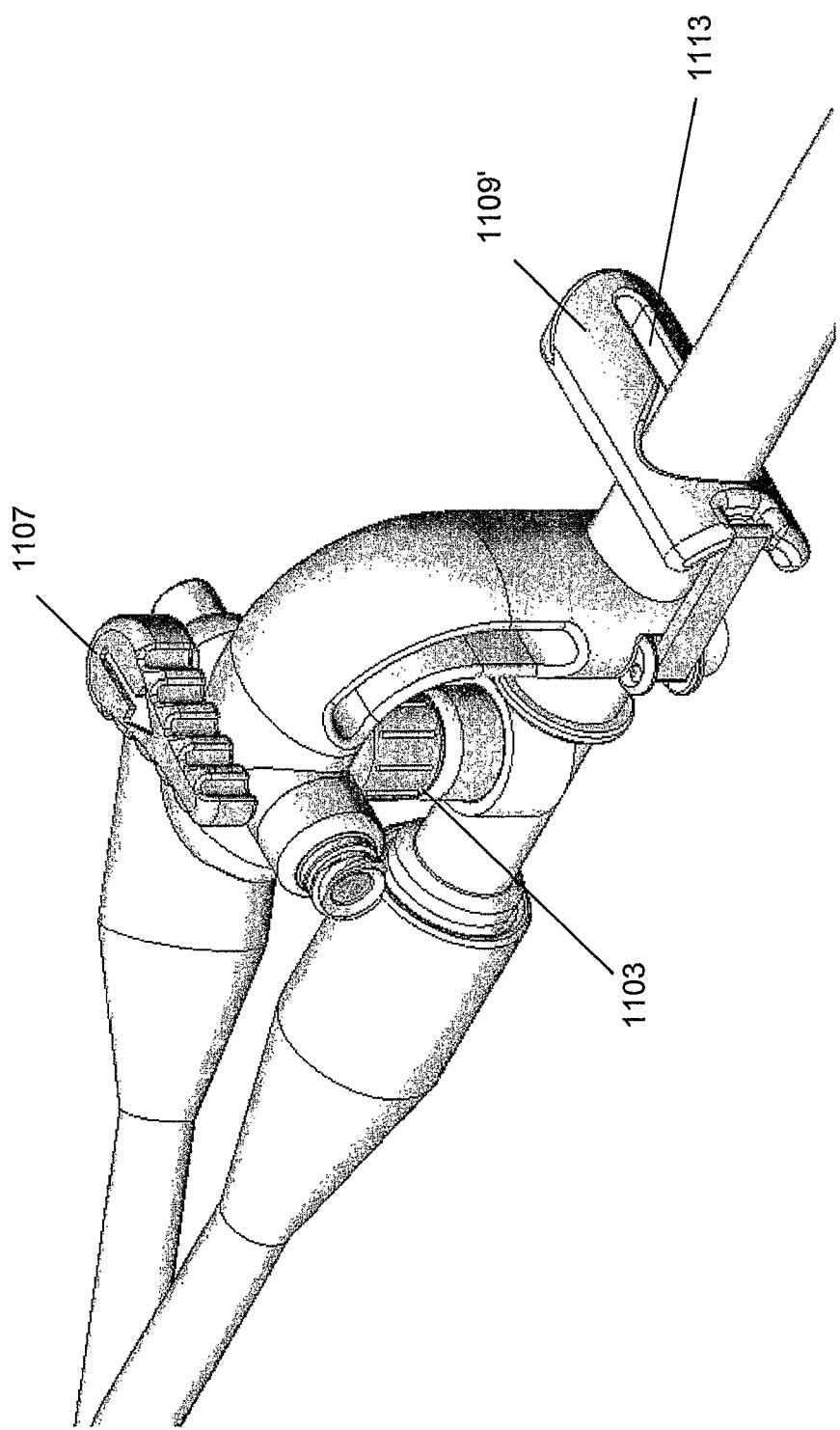
FIG. 11B shows a device similar to that of FIG. 11A, having a different type of clamping mechanism.
Figure 11C:
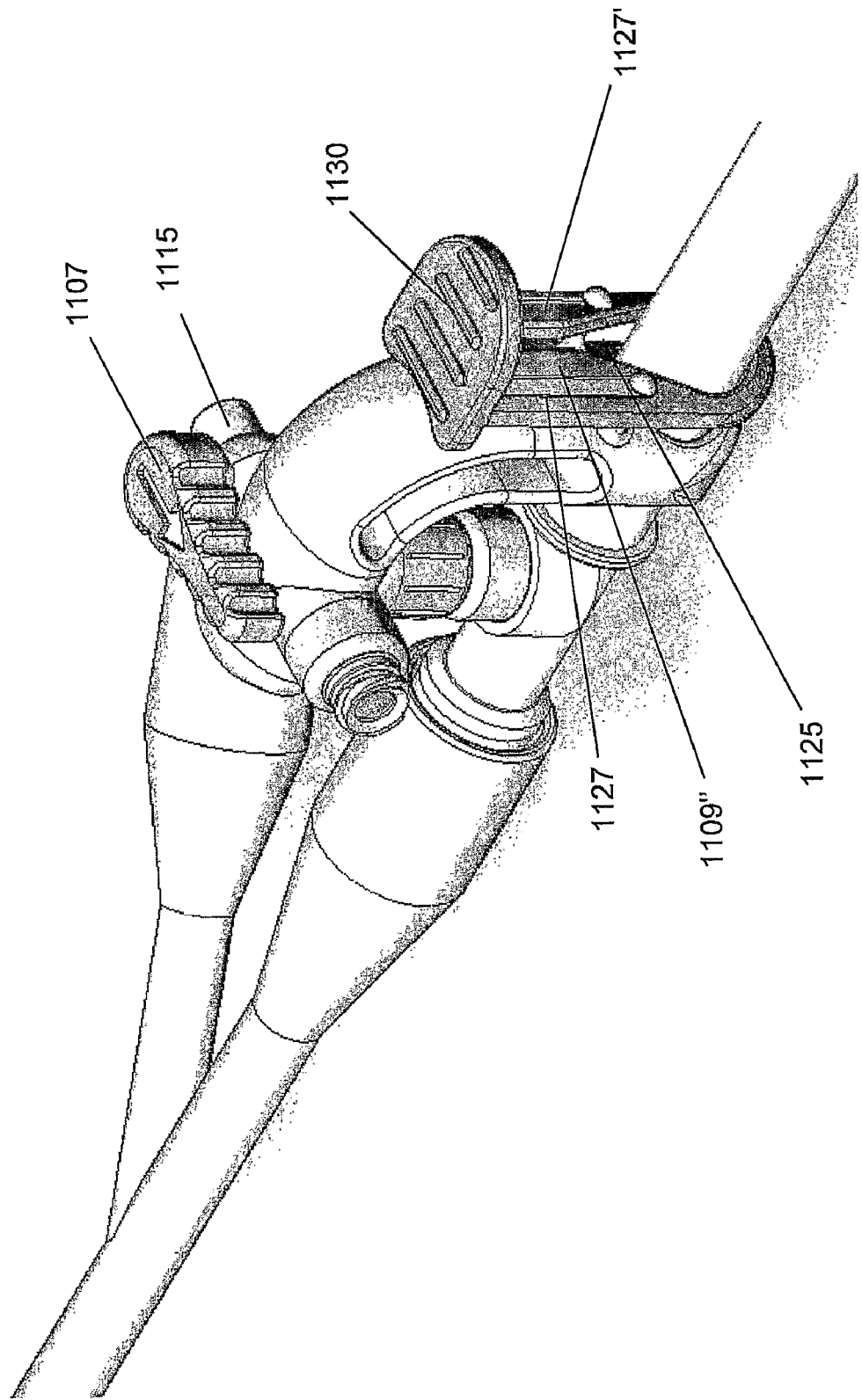
FIG. 11C shows a device similar to that of FIGS. 11A and 11B, having a different type of clamping mechanism.

FIG. 11B illustrates a device for measuring IAP similar to that shown in FIG. 11A, including a stopcock valve member 1107, a sampling port connector 1103 with an auto valve, and a clamp mechanism 1109'. However, in this embodiment, the clamp mechanism 1109' is configured such that to occlude the drain tube, the clamp mechanism 1109' is moved in a direction generally perpendicular to the longitudinal axis of the drain tube such that the drain tube is positioned in and pinched by the slot 1113. FIG. 11C is similar to FIGS. 11A and 11B, having a clamp mechanism 1109" with an opening 1125 to receive the drain tube that is teardrop-shaped with a slot at the top of the teardrop. On either side of the opening 1125 are slots 1127, 1127' to receive a pin such that the clamp mechanism can be moved in linear fashion. Above the opening 1125 is a ledge or platform 1130 to facilitate movement of the clamp mechanism by a user. In a rest state (i.e., urine is draining through the drain tube), the drain tube is positioned in the bottom portion of the teardrop-shaped opening 1125 which fully accommodates the drain tube without altering its dimensions. When it is desired to place the device in an activated state, a user pushes on the platform 1130 with a finger or thumb, causing the clamp mechanism 1109" to slide along the pins. This action positions the drain tube in the narrow portion of the opening 1125 and then into the slot at the top thereof, which pinches the drain tube to prevent fluid flow therethrough. The user then turns the stopcock valve 1107 member such that the arrow faces toward the fluid infusion line 1115 (bypass lumen), permitting fluid infusion into the catheter. Although not shown in detail, the drain tube housing of FIGS. 11A-C is designed to latch onto/around the drain tube without breaking the closed system, as discussed herein. One example of how this may be done is shown in FIGS. 12A and 12B.

Figure 12B:
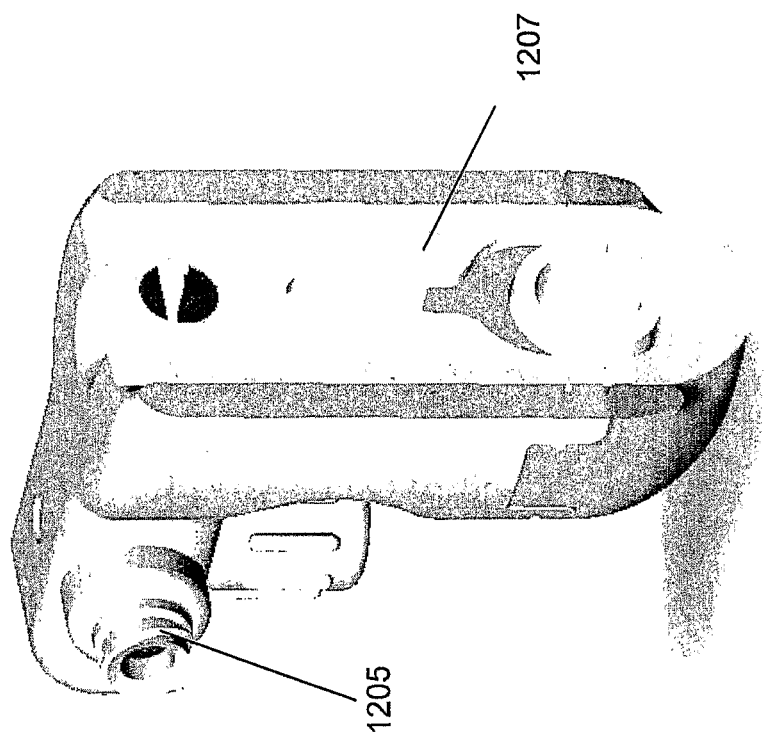
FIGS. 12A and 12B show another embodiment of a device for measuring IAP, including an auto valve attached to a sampling port, showing side perspective views thereof.
Figure 12A:
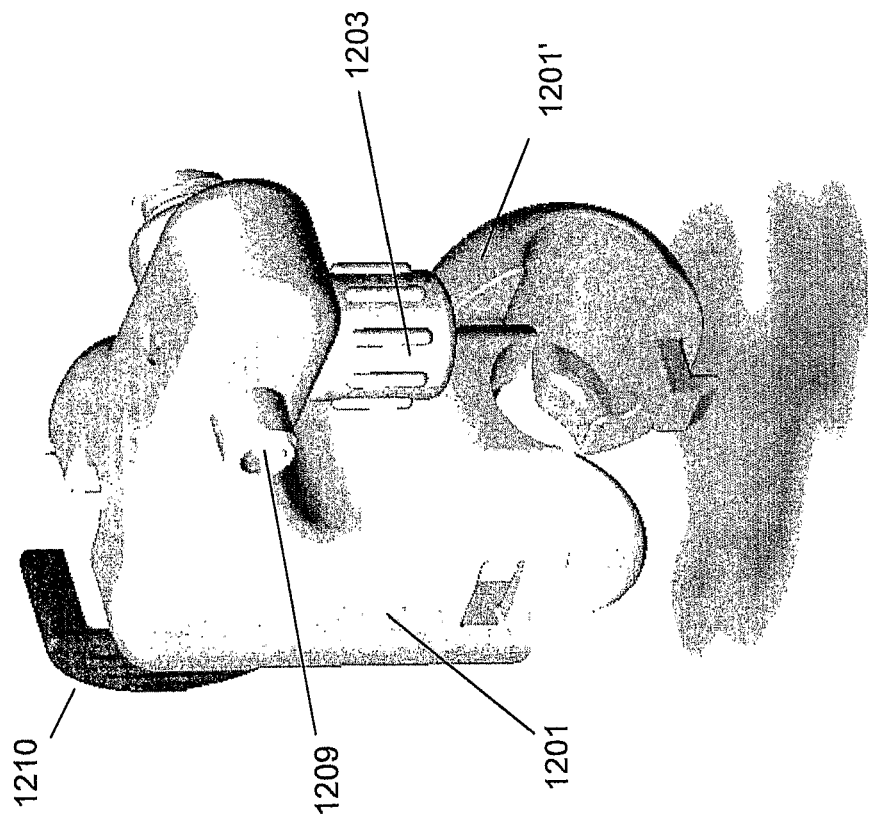

FIGS. 12A-12G illustrate another embodiment of a device for IAP monitoring. As in the devices shown in FIGS. 11A-11C, the devices in this embodiment may be used for long-term or even permanent attachment to the sampling port of a urinary catheter system. Of course, it is to be understood that in any of the bypass IAP measurement devices described herein, the devices may also be removed from the urinary catheter system without opening the closed urinary catheter system. The embodiment shown in FIGS. 12A-12G combines the functionality of the stopcock valve member and the clamp mechanism into a single activation member, such that by manipulating the selector (also referred to as an "activation member"), the device may both occlude the drain tube and open a fluid flow path from the bypass lumen (e.g., through a fluid infusion line) to the catheter system. FIGS. 12A and 12B show perspective views of each side of the device, which includes a housing 1201, 1201', an auxiliary sampling port 1205, a sampling port connector 1203, and a fluid injection line 1209 (forming a bypass lumen) similar to the embodiments described above.

The housing 1201, 1201' shown in FIGS. 12A-12G includes a second region configured as an attachment member 1201' that can be attached to a drain tube, having a protrusion that fits into an opening in a first region of the housing 1201. The attachment member 1201' can provide a locking connection that is either detachable or a permanent. In some embodiments, the action of completing the movement of placing the protrusion into the opening results in an audible and/or tactile indication that the housing is locked around the drain tube. In FIG. 12A, the attachment member 1201' is shown prior to the protrusion being placed within the opening, while in FIG. 12B, a locking connection has been made. The activation member of the clamp mechanism is shown in FIG. 12A, but is omitted from FIG. 12B to show the clamp mechanism 1207, which has an opening with a wide base and a narrow top portion, the wide base portion accommodating the diameter of a drain tube, while the narrow top portion is configured to pinch the drain tube enough to prevent fluid flow therethrough. An aperture above the opening permits connection of the selector (activation member) to the clamp mechanism.

Figure 12C:
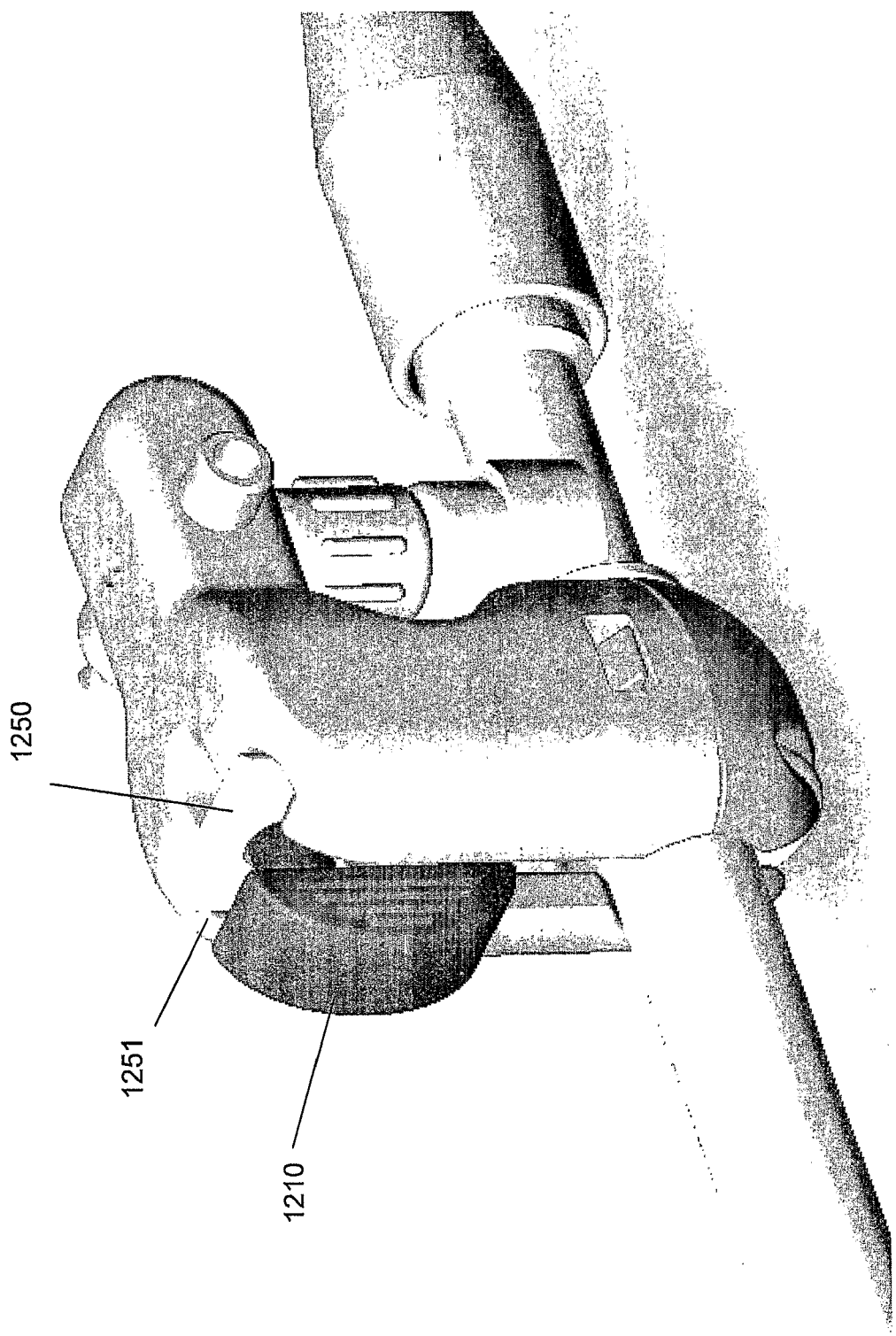
FIG. 12C shows a perspective view of the device shown in FIGS. 12A and 12B in a rest state, attached to a urine catheter system.

FIG. 12C shows a perspective view of the device attached to a urinary catheter system, with the sampling port connector connected to the sampling port of the catheter system, and the attachment member of the housing locked around the drain tube of the system. In this view, the selector 1210 is positioned such that the system is in a rest state (i.e., urine is draining from the catheter to the drain tube). The selector 1210 includes two spaced apart semi-circular surfaces, each including ridges thereon to facilitate handling, and a stem that is positioned through the aperture of the clamp mechanism to couple the components. In the rest state, the flat sides of the semi-circular surfaces are approximately perpendicular to the longitudinal axis of the drain tube and the stem (and aperture) are positioned adjacent a top surface of the housing.

Figure 12D:
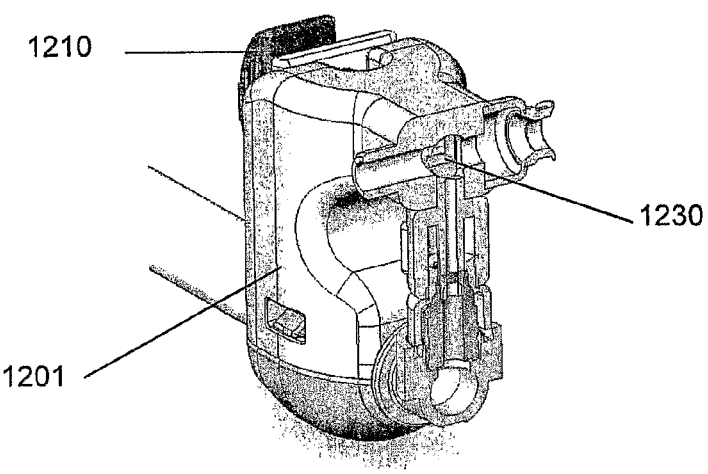
FIGS. 12D, 12E and 12F show different views of the device of FIGS. 12A and 12B in three different cross-sectional views.
Figure 12E:
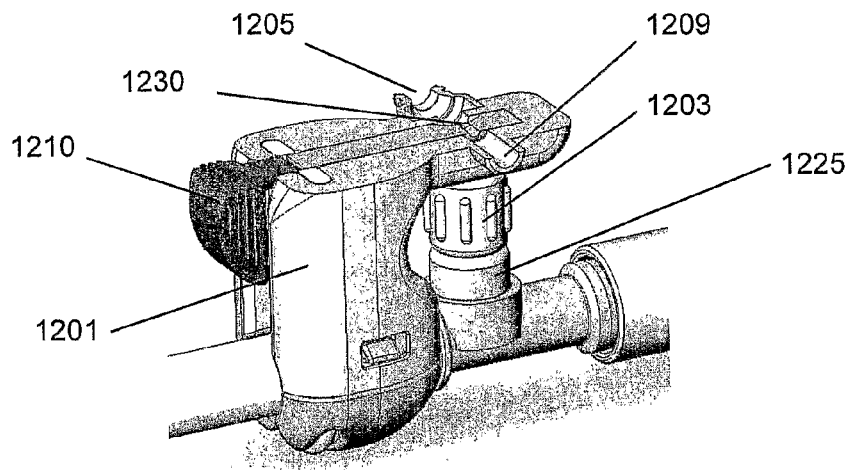
Figure 12F:
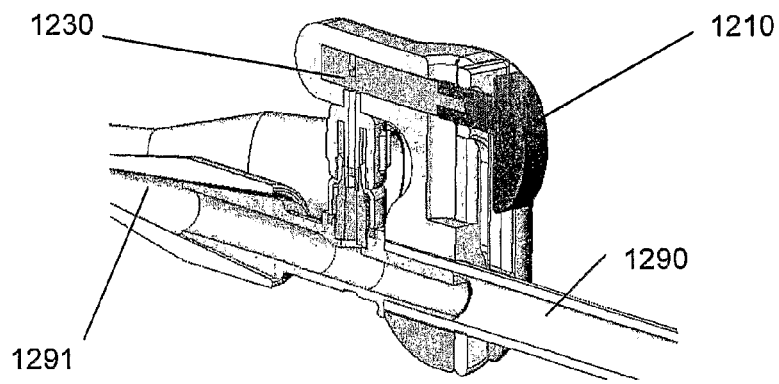

FIGS. 12D-12F illustrate three different cross-sectional views of FIG. 12C to show the interaction of the components of the device. In FIG. 12D, a cross-section is taken through the housing 1201 such that the sampling port 1225 and auto valve (which is part of the sampling port connector 1203 in this embodiment) are connected and shown bisected. In this cross-sectional view, a spindle valve member 1230 of the housing can be seen, the spindle valve member acting to prevent or permit fluid flow from the bypass lumen through the fluid infusion line to the catheter (i.e., through the sampling port 1203 of the catheter system). In the rest state as shown, the spindle valve member 1230 is in a closed position, meaning that fluid communication between the bypass lumen and the auto valve is prevented. In FIG. 12E, a cross-section is taken lengthwise through the device such that the selector 1210, fluid infusion line 1209 and auxiliary sampling port 1205 are bisected. In this view, the spindle valve member 1230 can be seen to connect directly with the activation member 1210, such that the positioning of the spindle valve member 1230 (e.g., in the open or closed position) is controlled by the selector.

Figure 12G:
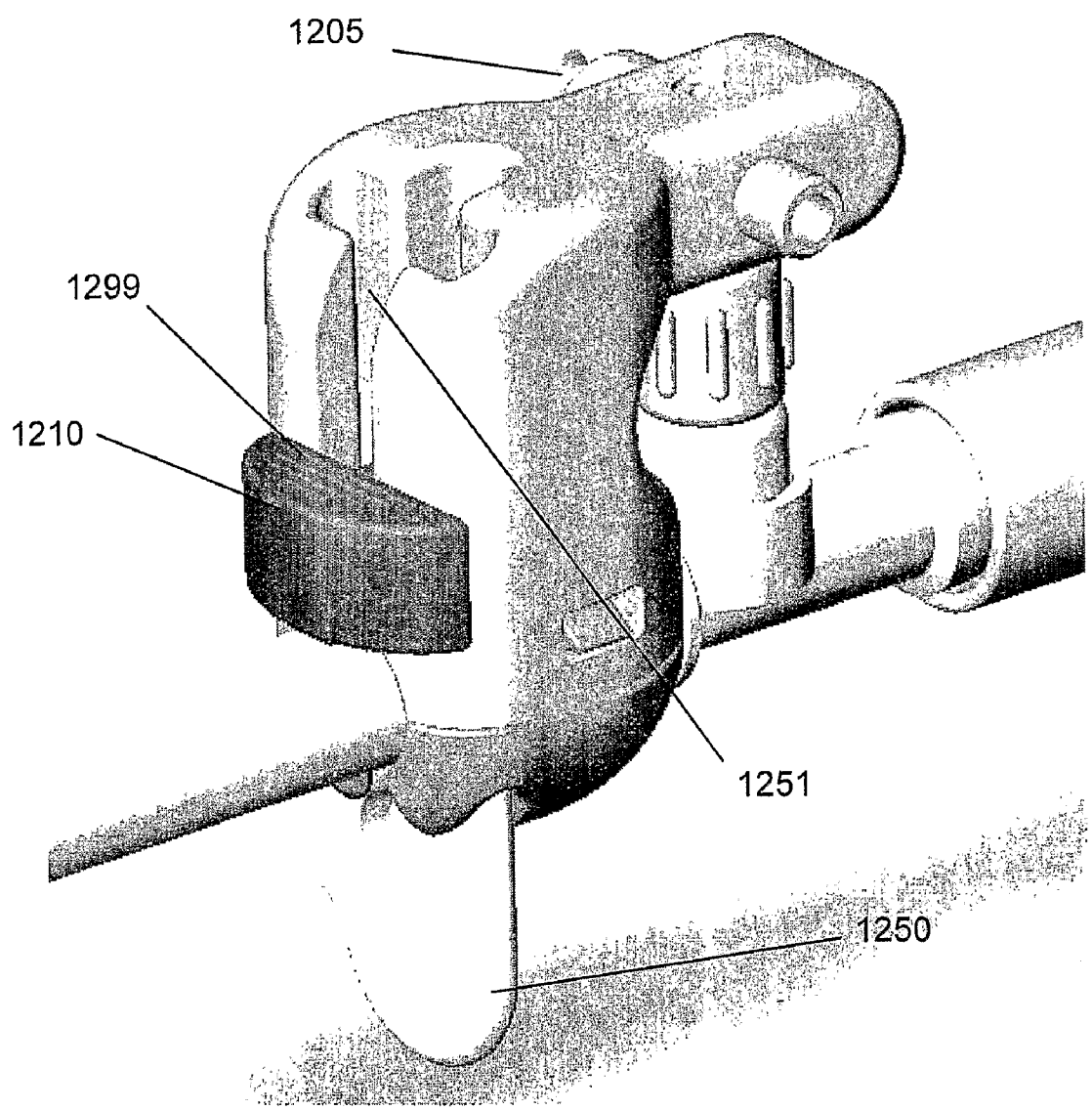
FIG. 12G shows the device of FIGS. 12A-12F occluding flow through a drain tube of a urine catheter system.

In FIG. 12F, a cross-section is taken lengthwise through the entire catheter system, bisecting the drain tube, housing 1201, and Foley catheter 1291. The housing has a slot 1251 adjacent the clamp mechanism 1250, which permits movement of the selector 1210 to occlude the drain tube, as best seen in FIGS. 12C and 12G. This view further illustrates the interaction between the selector 1210, spindle valve member 1230 and clamp mechanism 1250 of the device and it is noted here that due to the particular interaction between components, the selector is precluded from being moved in a downward direction to cause the clamp mechanism to occlude the drain tube. Specifically, a proximal portion of the spindle valve member 1230 resides within a recess of the selector 1210 and is configured such that when the system is in the rest state, the selector is prevented from moving in a downward direction by the proximal portion of the spindle valve member. When the selector is rotated 90 degrees, however, the proximal portion no longer provides an impediment to movement, allowing the selector to be pressed downward along the slot in the housing.

FIG. 12G shows the IAP monitoring system of FIG. 12C in an activated state, wherein the selector 1210 is first rotated 90 degrees to both place the spindle valve member in an open position (i.e., permitting fluid flow from the bypass lumen through the sampling port connector) and permits downward movement of the selector. As the selector is moved downward by the user, the narrow region of the clamp mechanism pinches the drain tube to prevent fluid flow therethrough. As mentioned above, the ridges 1299 on the surface of the selector may aid in the handling thereof as the selector transitions the IAP monitoring system from a rest state to an activated state. When the system is in the activated state, the auxiliary sampling port 1205 on the device is also in fluid flow communication with the Foley catheter so that urine sampling and testing can take place.

In the embodiments illustrated in FIGS. 5-12G, and described above, the device and is configured to conform to an inserted and operational Foley catheter system. That is, the housing is designed to attach to the catheter system (e.g., the drain tube thereof) while the system is operational (e.g., urine is draining from the bladder of a patient) and to occlude the drain tube as the bypass lumen is brought into fluid communication with a lumen of the inserted catheter. Because it is undesirable to break or open the closed catheter system, all components of the IAP measurement device are designed to interface with the elements of a standard Foley catheter system.

Figure 13:
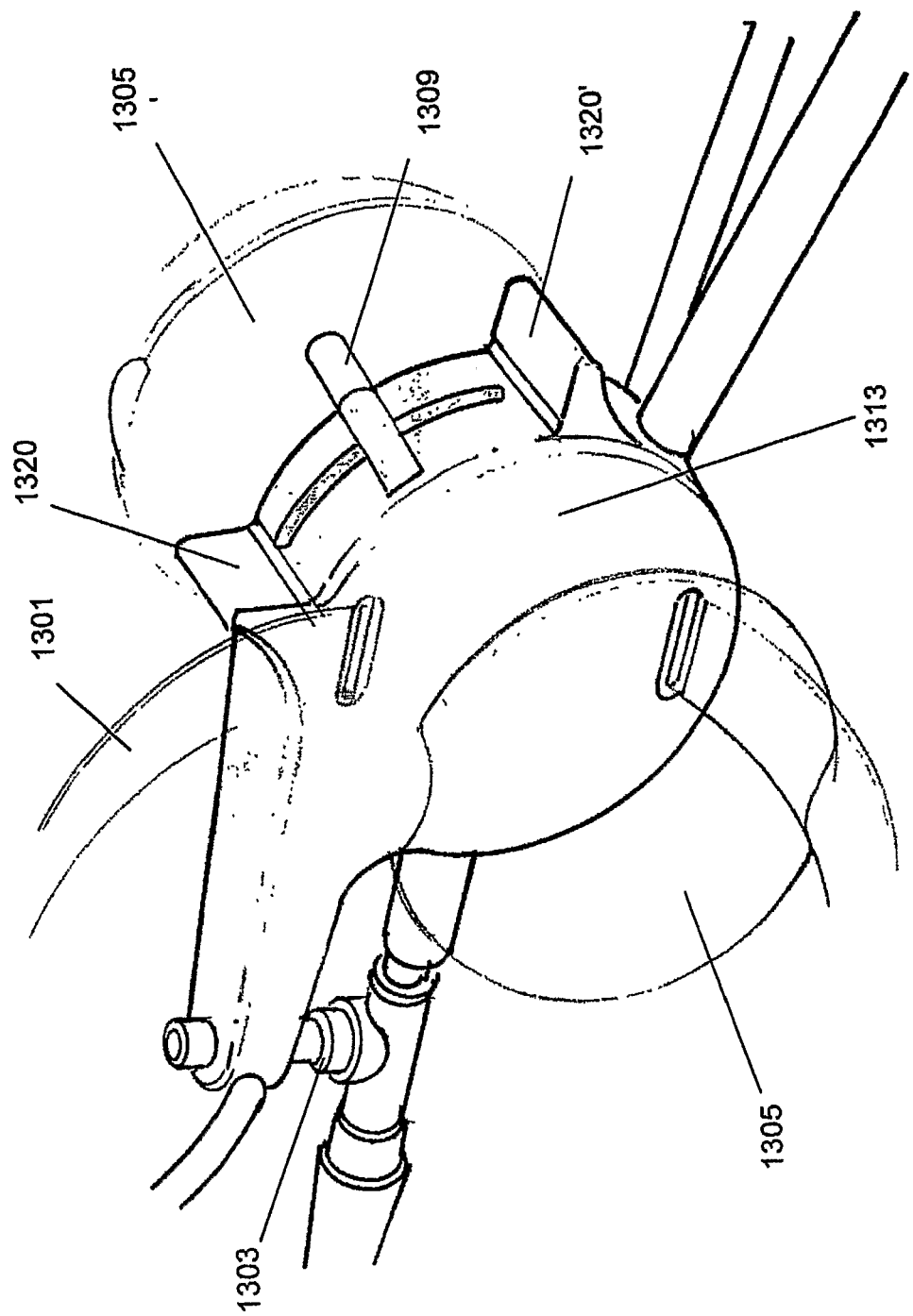
FIG. 13 shows another embodiment of a device for measuring IAP attached to a catheter system.

FIGS. 13 and 14A-14C show another embodiment of a urinary catheter system bypass device for measuring IAP. The device shown in FIG. 13 includes a holdfast 1301 for securing the device to either a patient, or to the bed, bedding or clothing of the patient. In FIG. 13, the holdfast comprises a belt or strap that may be attached to or worn by the patient. Other examples of holdfasts may include: adhesives, clips, ties, clamps, bandages, stand, mountings, or the like. As mentioned, the holdfast may also secure the device to the subject's clothing, bedding, or bed. For example, the holdfast may be a mount that connects the device to the bed (e.g., bed frame) so that it can be held in position. Maintaining the position of the device may be particularly useful for embodiments in which the pressure sensor is included as part of the device, since the relative position of the pressure sensor may effect the pressure measurement. Thus, in some embodiments, components of a system for measuring IAP (particularly the pressure sensor) may be secured (e.g., to the subject), even if other components are not secured. A holdfast may be used with any of the devices described herein for measuring IAP.

The embodiment shown in FIG. 13 also shows two pads 1305, 1305' on either side of the device. The pads may be cushions that enhance comfort of the device when it is attached or worn by a patient. For example, the pads may comprise gel pads. Any appropriate material may be used for the pad, including foamed materials, gels, fabric, etc. Ideally the pad is soft, preventing sharp corners or edges of the device from contacting the patient. Pads may also help position the device so that it can be readily accessed by a practitioner who may adjust or operate it. The pads may be located in any appropriate position, typically so that the pad or pads are positioned between the subject and the device. In FIG. 13, since the device may be worn between the subject's legs, pads are located on both sides of the device and may protect both of the subject's legs, even when the device is strapped to only one of the subject's legs (e.g., the upper thigh region). The device for measuring IAP shown in FIG. 13 also has a sampling port connector 1303, and a housing 1313 that may partially surround the drain tube of the urinary catheter. A selector (shown as a lever 1309) is located at the top of the housing 1313. The selector may control the clamp mechanism and open or occlude the drain tube, and may also allow fluid to enter the bypass lumen from a fluid infuser, as illustrated in FIGS. 14A to 14C.

Figure 14A:
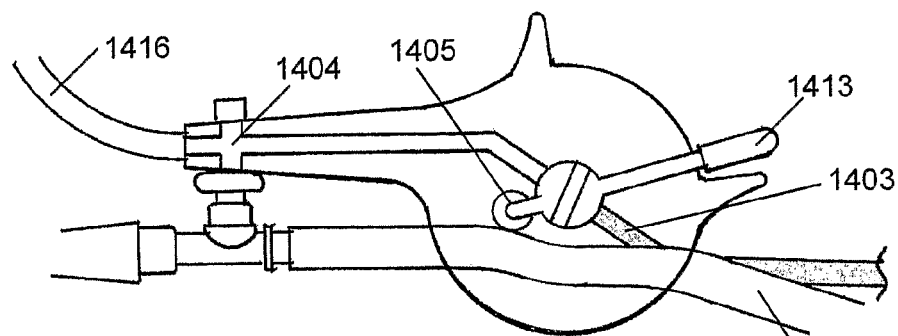
FIGS. 14A-14C illustrate operation of a device similar to the device shown in FIG. 13.
Figure 14B:
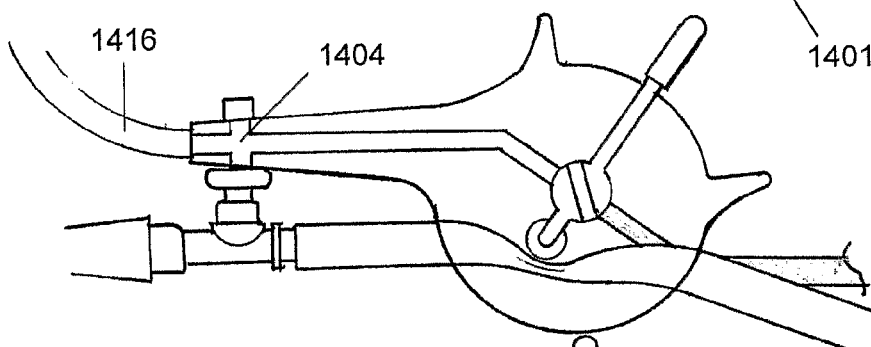
Figure 14C:
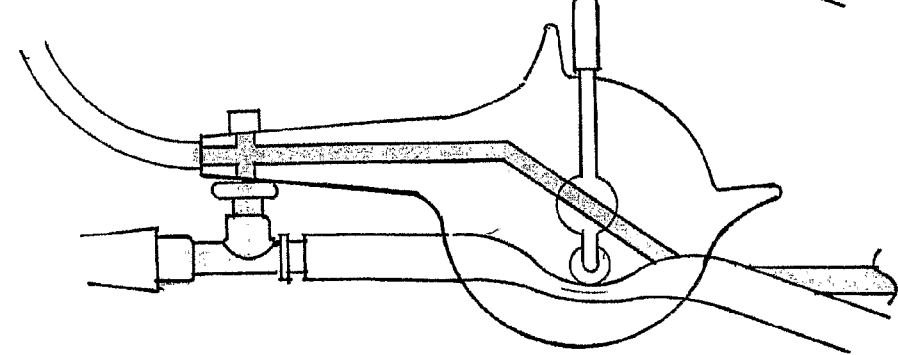

FIGS. 14A to 14C show cross-sections through the device for measuring IAP shown in FIG. 13. In FIG. 14A to 14C, the drain tube 1401 passes through a channel in the housing. The housing also includes a first fluid pathway that is connected at the proximal end to a fluid infuser (including a source of fluid) and at the distal end to the bypass lumen 1404. This pathway passes through the clamp mechanism 1405 that is connected to the selector 1413. The clamp mechanism 1405 is shown as a rolling pinch valve that pivots as the selector is moved and applies pressure to (e.g., pinching) the drain tube depending on the position of the selector 1413.

In operation, the device shown in FIGS. 13 and 14A-14C has three operational settings, which may be selected by the selector 1413 and may be indicated (e.g., printed) on the outer surface of the housing. In the first position, shown in FIG. 14A, the selector (lever) 1413 is pushed down, and flow through the first fluid pathway connecting the bypass lumen and the fluid infuser 1403 is occluded while flow through the drain tube 1401 is opened. This may be referred to as the "drain" setting, because urine within the drain tube may drain from the catheter. Flow through the first pathway is blocked because a portion of the fluid pathway that passes through the clamp mechanism is rotated out of register with the rest of the pathway.

The second position is shown in FIG. 14B. In the second position, the clamp mechanism has been rolled over a portion of the drain tube 1401 within the housing so that the drain tube is occluded, however the first fluid pathway is also occluded. Thus, fluid (e.g., urine) may not drain from the catheter system, and additional fluid (e.g., saline) may not be added from the fluid infuser. In the device shown in FIGS. 13 and 14A-14C, the bypass lumen 1404 is also in fluid connection with a second fluid pathway 1416 that is configured to connect to a pressure transducer (not shown) to measure pressure of fluid within the catheter system (and therefore the bladder). This may be referred to as the "sample" or "measure" setting, because IAP measurements may be taken with the selector in this position.

The third position is shown in FIG. 14C. In the third position, the clamp mechanism is rolled over a portion of the drain tube 1401, occluding it. However, the first fluid pathway connecting the bypass lumen 1404 and the fluid infuser is not occluded. Thus, fluid may be applied to the catheter system from the fluid infuser, as shown. This may be referred to as the "IAP" or "loading" setting, because fluid may be loaded into the catheter system (and bladder) to take an IAP measurement.

The device shown in FIGS. 13 and 14A-14C may be operated by moving the selector between the different positions in order to add fluid to the urinary catheter system and bladder, measure IAP, an allow fluid to drain from the device. The selector may be manually moved or automatically (e.g., assisted) moved. In FIG. 13, the housing is shown with standing walls 1320, 1320' to provide leverage and assist in the manual movement of the selector. As mentioned, the housing or selector may also be labeled (e.g., "drain", "IAP", "measure", etc.) to indicate what setting the selector is on. In some variations, the device may also include an alert (e.g., a visual or aural alarm) indicating that the drain tube has been occluded. The alert may be delayed so that it is only activated after a delay to allow measurement of IAP.

Figure 15:
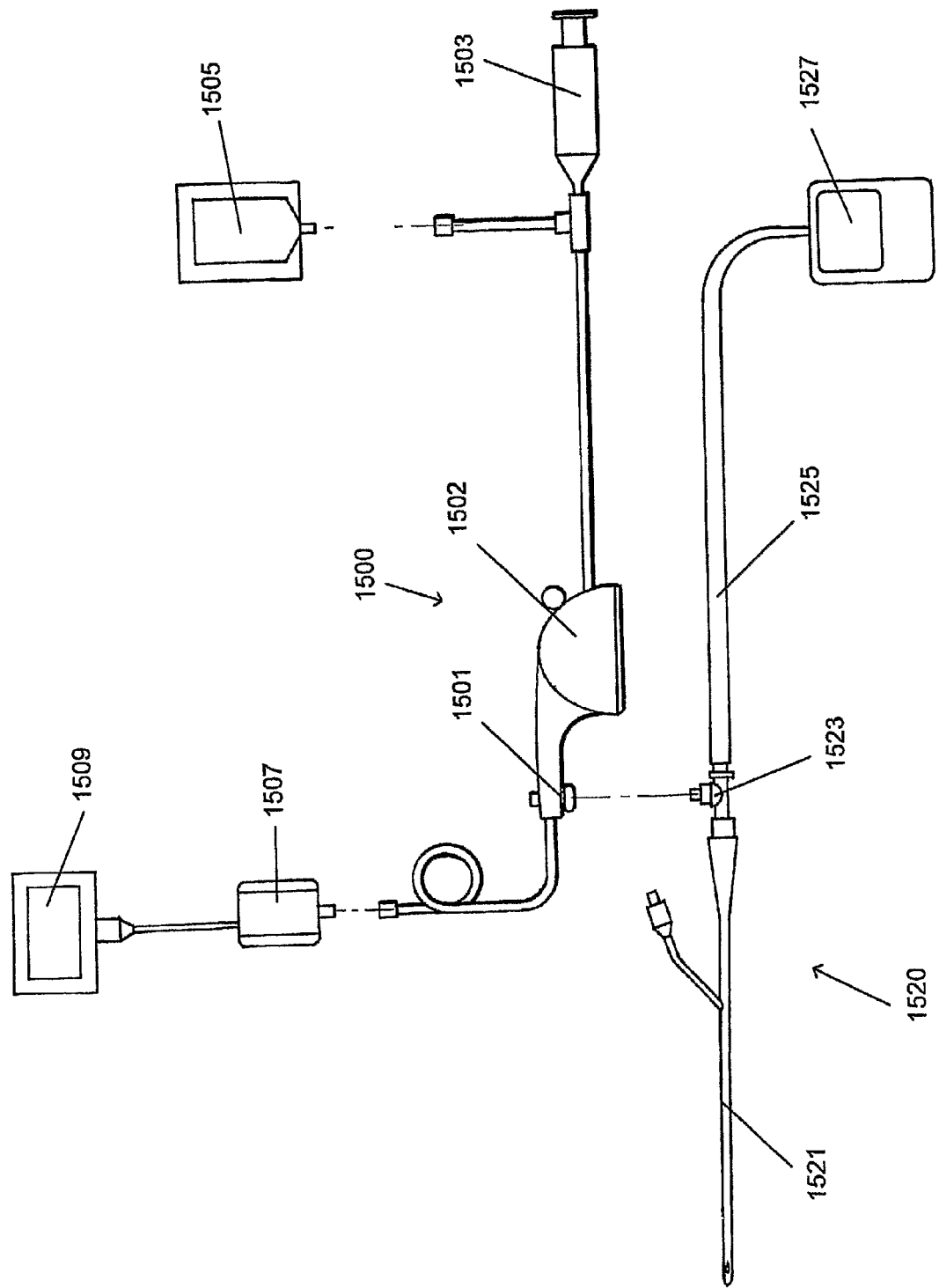
FIG. 15 shows a system for measuring IAP including a device similar to the device for measuring IAP shown in FIG. 13.
Figure 16:
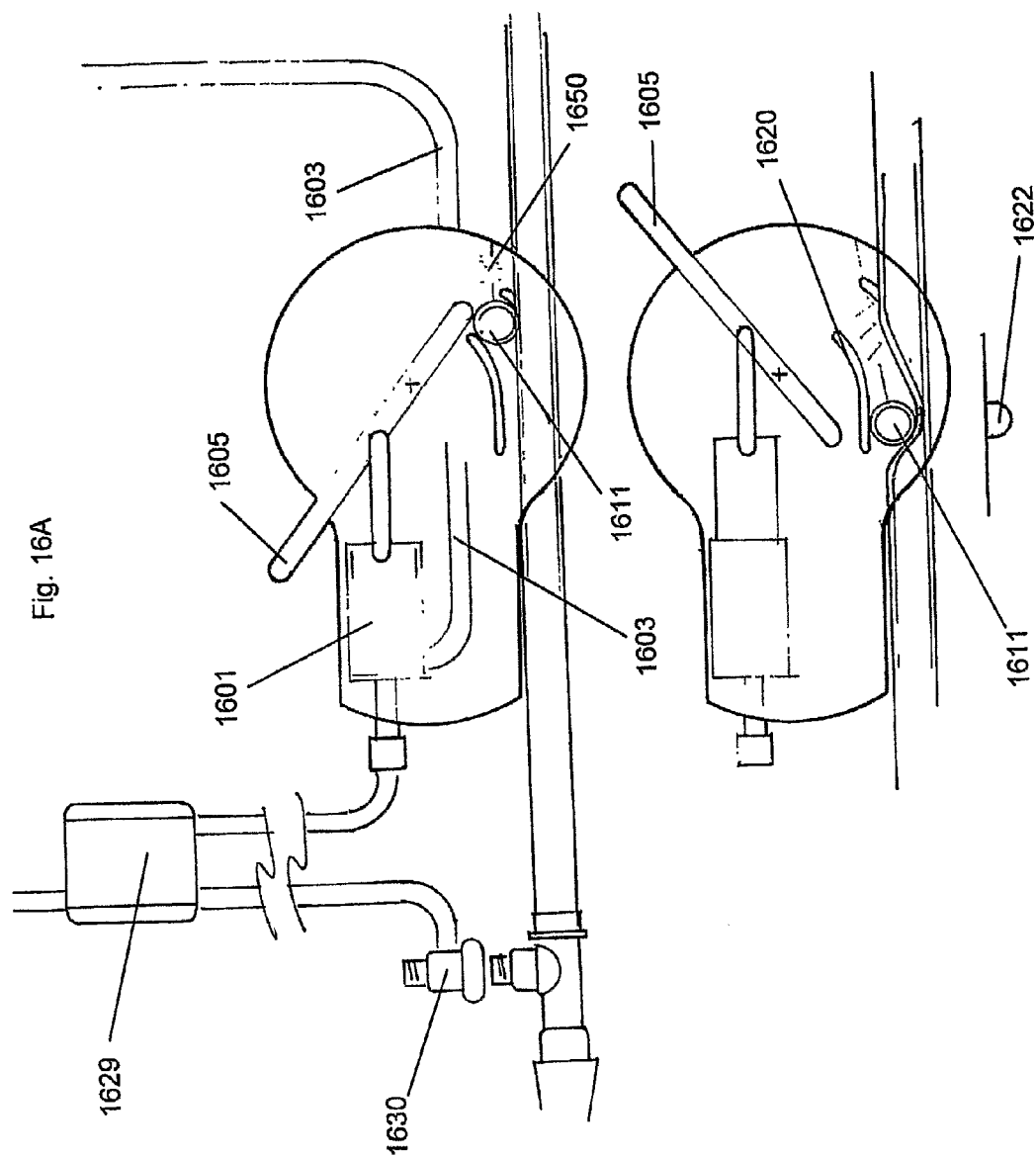
FIG. 16A shows another embodiment of a device for measuring IAP attached to a urinary catheter system.
FIG. 16B shows the device of FIG. 16A occluding the drain tube of the catheter system.

FIG. 15 illustrates a system for measuring IAP that incorporates the device shown in FIGS. 13 and 14A-14C. In FIG. 15, the IAP measurement system includes the device 1500, as well as a fluid infuser 1503, a fluid source 1505, a pressure transducer 1507 and a monitor or recording device 1509 for measuring the IAP. FIG. 15 also shows the catheter system 1520, including a Foley catheter 1521, a sampling port 1523, a drain tube 1525, and a urine collection bag 1527. In some variations, the system for measuring IAP includes the catheter system (or components of the catheter system). The system for measuring IAP may be connected to the catheter system by connecting the sampling port connector 1501 to the sampling port 1523 and placing at least a portion of the drain tube 1525 within the drain tube housing 1502 of the device 1500. As described above, the drain tube housing may fasten or lock around the drain tube. The IAP measurement system may be connected to a closed urinary catheter system (e.g., an indwelling catheter system that has been inserted into a patient). The IAP measurement system may also be later removed from an indwelling urinary catheter system without opening the urinary catheter system. For example, the device can be removed by opening the drain tube housing 1502 to release the drain tube 1525 and disconnecting the sampling port connector 1501 from the sampling port 1523.

Another embodiment of a device for measuring IAP that is similar to the embodiment shown in FIGS. 13-15 is shown in FIGS. 16A and 16B. In FIGS. 16A and 16B, the device incorporates a fluid infuser 1601 that is connected to the selector 1605 so that fluid may be added using the selector. The device includes a housing 1607 that partly encloses a clamp mechanism shown as a pinch valve 1611 that can roll across the drain tube to close off the drain tube. The fluid infuser is also at least partly enclosed by the housing 1607, and is connected to a fluid source through a supply line 1603.

In operation, the same selector may be used to occlude the drain tube and supply fluid to the catheter to perform an IAP measurement. For example, in FIG. 16A the fluid infuser is shown as a simple displacement (e.g., plunger) pump type of infuser 1601. Moving the selector 1605 down (e.g., to the right in FIG. 16A) causes the lever arm of the selector to pivot, simultaneously causing the clamp mechanism (the rolling pinch valve 1611) to occlude the drain tube, and also causing the infuser 1601 to draw fluid (e.g., saline) from the fluid source into the reservoir of the infuser 1601. In this variation, the clamp mechanism includes a lock 1620 that holds the clamp mechanism 1611 in the occluding position until it is released by a release mechanism, shown in FIG. 16B as a button 1622. The clamp mechanism is biased (shown here as an elastic or spring bias 1650) in the non-occluding position, so that activating the release mechanism automatically returns the clamp mechanism to open (non-occluding) position. Once the drain has been occluded by the clamp mechanism and the fluid infuser loaded with fluid (see FIG. 16B), fluid may be pumped into the catheter system by moving the selector 1605 to the left. In FIGS. 16A and 16B the fluid infuser is connected in-line with the pressure transducer 1629 and with the bypass lumen connected to the catheter system through the sampling port connector 1630.

In some variations, movement of the selector may be configured so that a single activation (e.g., movement of a lever, push of a button, etc.) can both occlude the drain tube and apply fluid from the fluid infuser. For example, the embodiment shown in FIGS. 16A and 16B could be modified so that pulling the selector lever down occludes the drain tube and pumps fluid, allowing IAP measurement. Returning the lever to the starting position would open the drain valve, and re-fill the reservoir of the fluid infuser, preparing the device for the next measurement.

Figure 17:
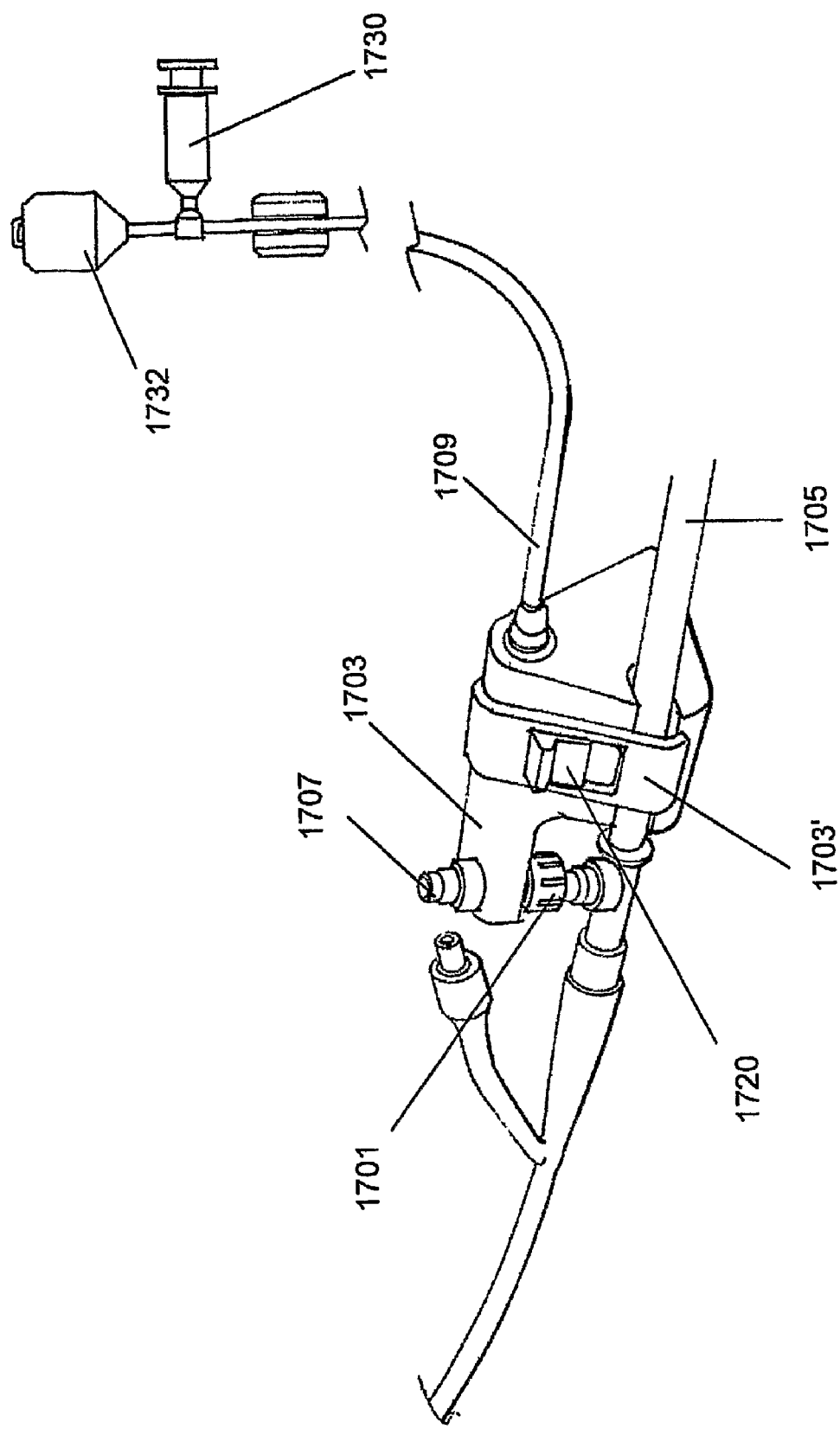
FIG. 17 shows another embodiment of a device for measuring IAP attached to a catheter system.

FIG. 17 shows another variation of a device for measuring IAP as described herein. In FIG. 17, the device includes a sampling port connector 1701 (shown connected to a sampling port of a catheter system) and an auxiliary sampling port 1707. The sampling port connector connect a bypass lumen (not visible) to the lumen of the catheter system with a first fluid pathway 1709 configured to be in fluid connection with a fluid infuser 1730, a fluid source 1732, and a pressure transducer 1728. The sampling port connector is connected to a drain tube housing 1703. The drain tube housing includes a channel for the drain tube 1705 and can be closed over the drain tube 1705 of a catheter system by securing a second section of the housing 1705' to the first section of the housing 1705. A clamp mechanism (not visible) can occlude the drain tube, and can be controlled by the selector 1720.

In the embodiments shown in FIG. 17, the housing is adapted so that it has a base than can be used to stably place the device near a patient's leg (or between their legs). Thus, the housing has a triangular cross-section. Although not visible in FIG. 17, the selector of this embodiment may both occlude the drain tube and open (or occlude) the fluid pathway (in connection with the bypass lumen) for adding fluid into the catheter system, as previously described (e.g., see FIGS. 12 and 14). FIGS. 18A and 18B illustrate another variation of a selector and clamp mechanism that is configured to perform this dual function.

FIG. 18A shows a device for measuring IAP having a housing 1801 that includes a clamp mechanism 1805, 1805' configured to selectively occlude either the drain tube 1807 or the fluid pathway for adding fluid within the catheter system 1809. The clamp mechanism is configured as a rotary dual pinch-valve. This pinch valve is controlled by a selector 1803, shown in FIG. 18A as a knob, that can be turned to open or occlude flow through either the drain tube or the tube forming the fluid pathway for adding fluid within the catheter system 1809. For example, FIG. 18A shows the device in which the drain tube is open and the fluid pathway for adding fluid from the fluid infuser 1830 is occluded. FIG. 18B shows the device after turning the selector 1803 so that the clamp mechanism occludes the drain tube and allows fluid to flow through the fluid pathway between the bypass lumen and the fluid infuser 1830. Because this fluid pathway is also connected to the pressure transducer 1832, a pressure measurement may also be taken when the selector is in the position shown in FIG. 18B.

Figure 19A:
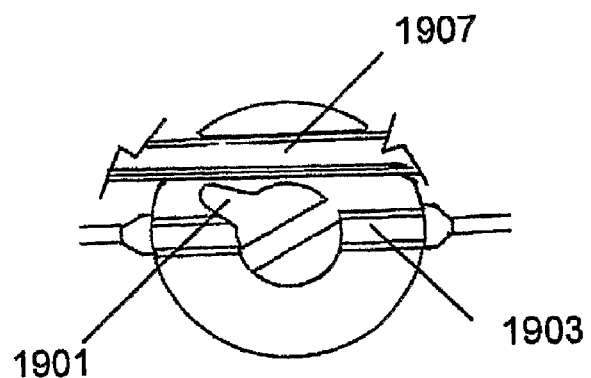
FIGS. 19A and 19B illustrate a drain tube housing that may be part of a device or system for measuring IAP, as described herein.
Figure 19B:
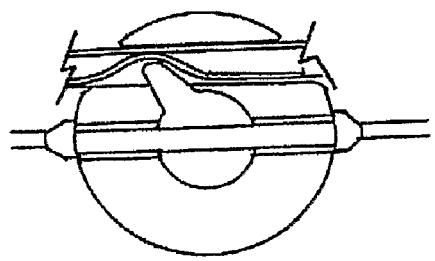

FIGS. 19A and 19B show another embodiment of a housing similar to the housing of FIGS. 18A and 18B. In FIG. 19A, the clamp mechanism 1901 and selector (e.g., dial), include a portion of the first fluid pathway 1903 between the bypass lumen and the fluid infuser for adding fluid to the catheter system when the device is attached to the catheter system. The housing shown in FIGS. 19A and 19B is similar to the clamp mechanism and selector shown in FIGS. 14A-14C. In FIG. 19A the drain tube 1907 is open and the first fluid pathway is occluded. In FIG. 19B the drain tube is occluded and the first fluid pathway is open.

Figure 20:
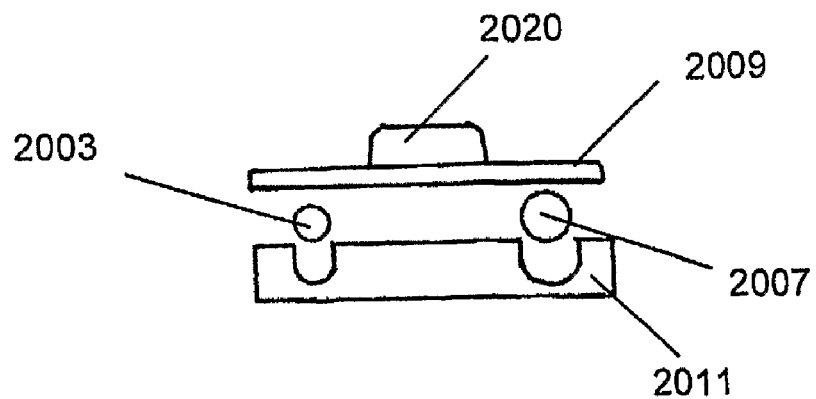
FIG. 20 shows a cross-sectional view through a drain tube housing similar to the housing shown in FIGS. 18A and 18B.

FIG. 20 shows one embodiment of a housing that may be used with the examples shown in FIGS. 18A-18B. This housing includes a first region (upper region 2009) and a second region (lower region 2011) that may be separated so that the drain tube 2007 and the tube connecting the bypass lumen to the fluid infuser 2003 may be inserted into the housing. The first and second regions of the housing may be locked together. The selector 2020 may also be attached to the housing. The housing shown in FIG. 20 may also be adapted for the embodiment shown in FIGS. 19A and 19B. In FIG. 19A, the tube connecting the bypass lumen to the fluid infuser 1903 is integrated into the housing, rather than being a separate tube.

As discussed herein, a device for measuring IAP may include a fluid infuser integrated into the device (e.g., into the housing). FIGS. 21A and 21B show one embodiment of such a device. In FIG. 21A, the device includes a housing 2101 that incorporates a fluid infuser (not visible). The fluid reservoir 2105 of the infuser (seen in the cross-section through the housing shown in FIG. 21B) may be filled from a fluid source 2107 such as a fluid bag (e.g., a saline bag connected to a drip line). A valve 2109 (such as a one-way valve) may be included to prevent backflow from the housing 2101 into the fluid supply 2107. An air vent 2111 may also be included. In FIGS. 21A and 21B, the selector 2115 may be used to occlude the drain tube, as described above, and also to deliver fluid into the catheter system. Thus, the device may be a single activation device, in which a single selector may be actuated to both stop flow through the drain tube and supply fluid so that an IAP measurement can be made. In some embodiments, actuation of both the occlusion of the drain tube and the application of fluid into the catheter system is done by a single movement of a selector. In other embodiments, the selector may be moved in different (including sequential movements) positions to first close the drain, and then apply fluid into the catheter system. Examples of devices in which a single selector is used to both close the drain and apply fluid are described herein (e.g., FIGS. 13-15).

Figure 22:
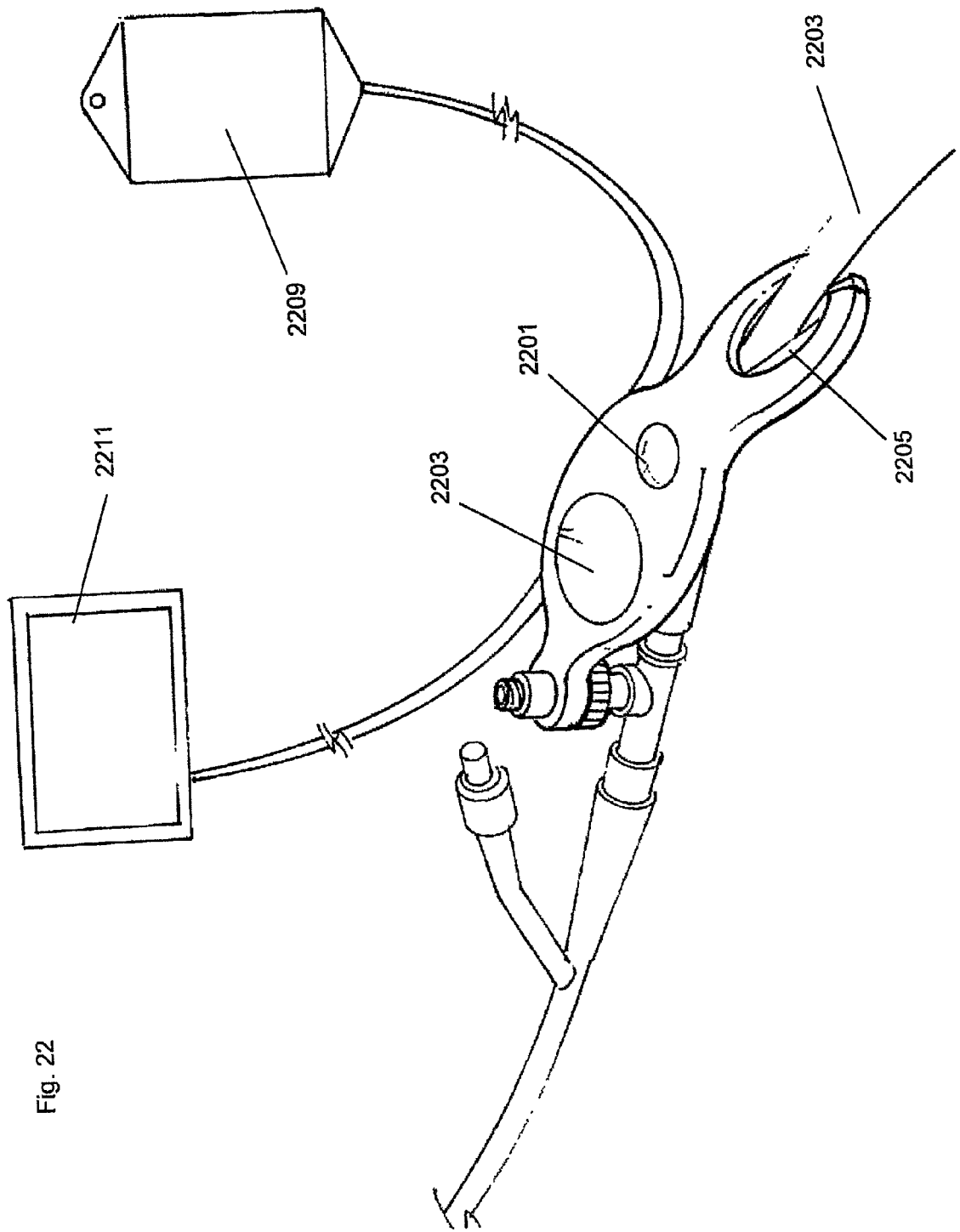
FIG. 22 shows another embodiment of a device for measuring IAP attached to a catheter system.

A device for measuring IAP may also be an electromechanical. For example, FIG. 22 shows one embodiment of a single activation device that includes a selector (button 2201). Pressing the selector (e.g., a start button), activates the device so that it automatically occludes the drain tube 2203 by activating the pinch valve 2205 and pumping fluid (e.g., saline) into the catheter system from a fluid source 2209. This device may include an integrated fluid infuser (e.g., pump). An IAP measurement may then be taken. In the embodiment shown in FIG. 22, the device also includes a pressure transducer (not shown), which is connected to an LCD readout/display 2203, and may also be connected to additional recording/monitoring devices 2211 (e.g., hospital monitors).

Another example of a device for measuring IAP that includes a fluid infuser is shown in FIGS. 23A-23D. In this embodiment, a selector is attached to the housing, and may be used to both occlude the drain tube and pump fluid. The selector may also visually indicate when the clamp mechanism has occluded the drain tube. For example, FIG. 23A shows a perspective view of this embodiment. The housing 2301 is configured to include an ergonomic selector 2303 on the upper surface. The base of the housing includes a channel for the drain tube, and a connector for a first fluid supply tube, configured to attach to a fluid supply source. The selector includes grips (e.g., finger grips) at the top, so that it may be readily grasped and manipulated.

FIG. 23B shows a top view of this device. The selector 2303 includes an indicator that may be used to indicate the status of the selector. For example, the hole through the selector may indicate (based on the position of the selector) that the clamp mechanism is occluding the drain tube. This may be indicated by presenting a red color through the indicator 2309 (e.g., view port) on the selector. FIG. 23C shows a cross-section through the housing and selector. FIG. 23C also shows a cross-section though the clamp mechanism 2311, which is connected to the selector 2301, so that when the selector is rotated, the clamp mechanism (an asymmetric pinch clamp) engages and occludes the drain tube 2307 by pinching it shut, as shown in FIG. 23C. The piston region 2315, which may form part of a fluid reservoir and is part of the fluid infuser, is also shown.

FIG. 23D shows another cross-section through the housing of the device, at the level of the clamp mechanism 2311 (near the base of the housing), illustrating the action of the clamp mechanism to occlude the drain tube 2307. Rotating the asymmetric pinch valve (e.g., by rotating the selector 2303) causes the valve to press against a hinged door 2317. The hinged door, in turn, presses against and occludes the drain tube, as shown. In some variations the intermediary hinged door is not used, and the asymmetric pinch valve directly presses against the drain tube. However, using a hinged door-type mechanism as illustrated here may provide a mechanical advantage, and may more rapidly occlude the drain tube.

In addition to occluding the drain tube, the selector 2303 may also be configured so that it activates the fluid infuser. By moving the selector up and down, the fluid infuser may prime (e.g., fill the fluid reservoir of the infuser with fluid) and inject fluid into the catheter system. For example, in FIG. 23C, the piston region may be drawn up or pushed down to draw in or expel fluid from a fluid reservoir within the fluid infuser, which is included within the housing. This is illustrated by the arrow 2325. Two or more one-way valves may be included to ensure that fluid is drawn into the fluid infuser from the fluid source and not the bypass lumen, and that fluid is expelled from the device through the bypass lumen, and not the fluid source. The selector may be configured so that it only allows priming and pumping (e.g., drawing the selector up and down) when the selector has been turned so that the clamp mechanism occludes the drain tube. In some variation the fluid infuser operates to prime and pump by screwing (e.g., by rotating) the selector into or out of the housing, rather than simply pushing or pulling it.

Another variation of the device similar to that shown in FIG. 23 is shown in FIG. 24A-24C. These figures show a cross-section through a device having a housing 2401 and a selector 2403. The housing includes a pinch valve 2406 for pinching the drain tube 2407 that sits in a channel along the bottom of the housing. FIG. 24A shows the normal position, in which the drain tube 2507 is opened. In FIG. 24B, the selector 2403 is drawn up to pull fluid into the reservoir of the fluid infuser 2421. Pulling the selector 2403 up causes a plunger 2409 to move up, creating a negative pressure within the fluid reservoir, and drawing fluid from the fluid source into the fluid reservoir 2421 of the device, as shown. Pushing the selector (e.g., plunger arm) back down causes the fluid to be forced from the fluid reservoir 2421, as shown in FIG. 24C, through the bypass lumen (not shown) and eventually into the catheter system. The drain tube is occluded by continuing to push the selector down, forcing the clamp mechanism down, where it eventually occludes 2425 the drain tube 2407, as shown in FIG. 24C. In some embodiments, the drain tube may be locked in the occluded position. For example, the drain tube may be locked in the occluded position by turning the selector while pressing in, or the like. A separate selector may also be used to control a clamp mechanism for occluding the drain. For example, a lever or button may control a clamp mechanism.

Figure 25B:
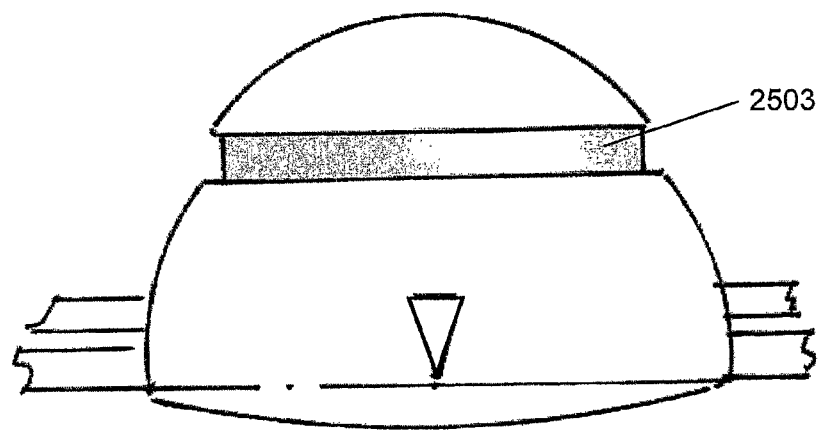
FIGS. 25B and 25C show side views of the device for measuring IAP shown in FIG. 24A-25A
Figure 25C:
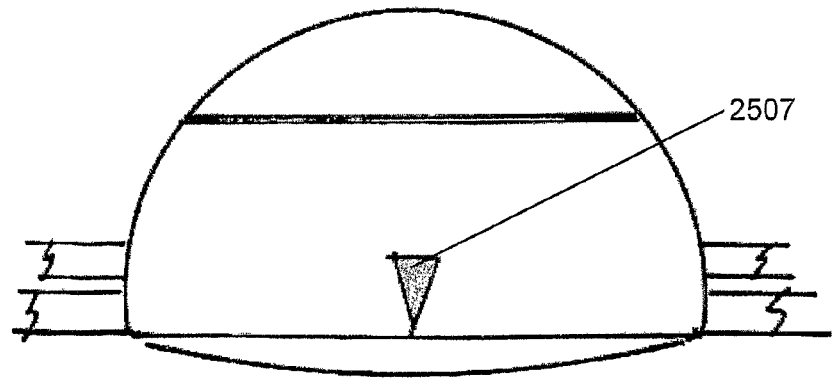

FIG. 25A-25C show various perspective views of the device described in FIG. 24. In FIG. 25B, the device is shown in the neutral position (corresponding to FIG. 24A). An indicator, shown here as a colored band around the periphery of the selector 2503, can indicate that the device is in the neutral state, and that the drain tube is not occluded. For example, the colored band may be a green band. When the device is occluding the drain tube, a second indicator 2509 may indicate that the drain tube is closed, as shown in FIG. 25C. FIG. 25A shows one variation of this device including a fluid source 2517 and a pressure transducer 2519. This device can be attached to a catheter system through a sampling port connector (not shown).

Figure 26:
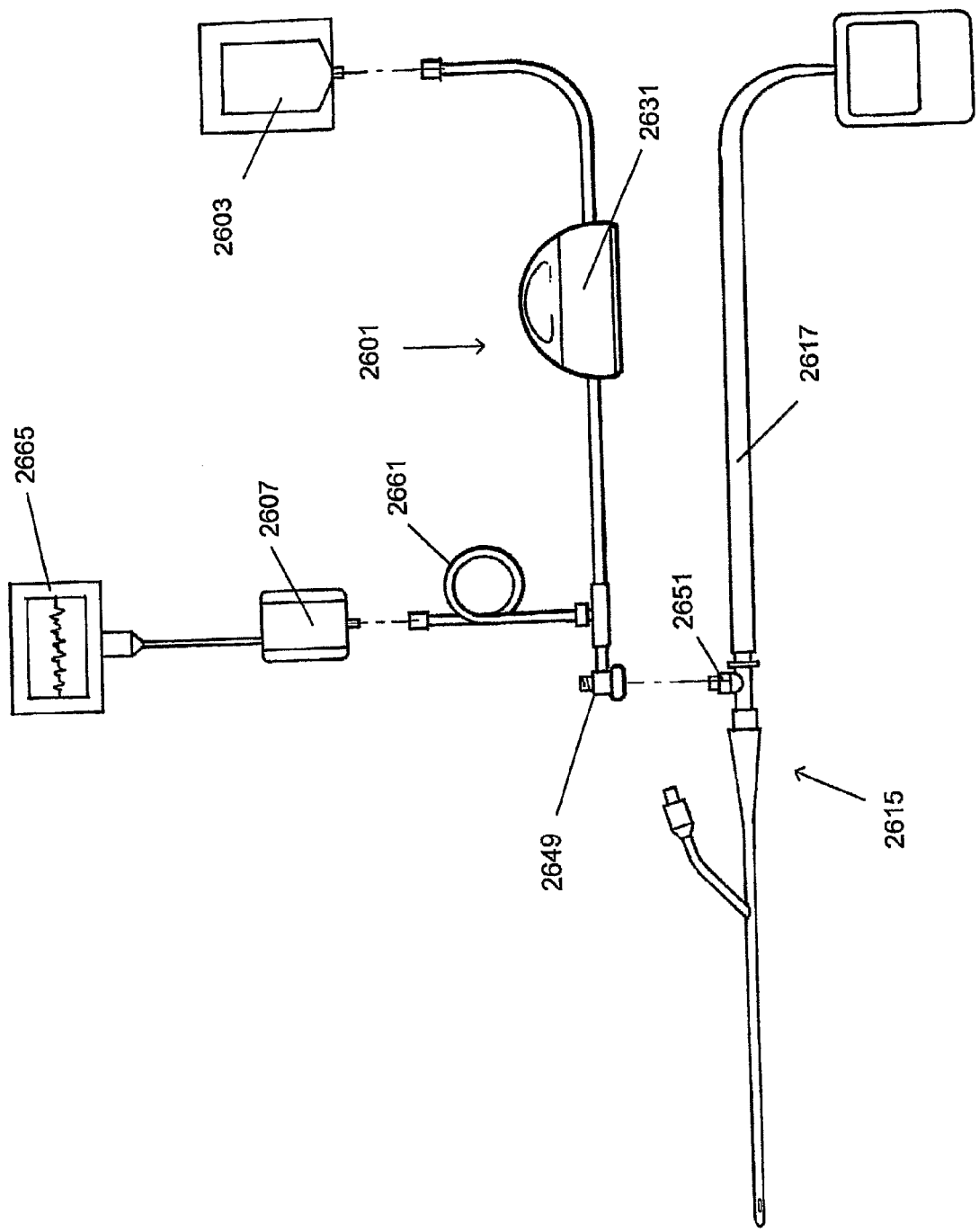
FIG. 26 shows a system for measuring IAP including a device similar to the device for measuring IAP shown in FIGS. 24A-25C.

FIG. 26 shows a system including the device described in FIGS. 23A-23D or FIGS. 24A-25C. As described above for similar devices for measuring IAP, device 2601 may be connected to a fluid source 2603 and a pressure transducer 2607. The device 2601 is configured for attachment to a catheter system 2615, and the drain tube 2617 may be enclosed within the drain tube housing of the device 2601. In operation, the device may be connected and disconnected from a catheter system 2615 while the catheter system remains inserted in a patient. For example, the drain tube 2617 region of the catheter system can be connected to the housing 2631. The drain tube housing encloses (at least partially) a clamp mechanism. Placing the drain tube within the housing positions the drain tube so that it can be occluded by the clamp mechanism and prevent flow. The sampling port connector 2649 is then connected to the catheter system through the sampling port 2651 of the catheter system 2615. Connecting the sampling port connector to the sampling port places the bypass lumen of the device in fluid communication with the interior of the catheter system, and therefore the bladder. The sampling port connector and the drain tube may be connected to the catheter system in any order. In some variations, it may be preferable to connect the sampling port connector to the sampling port first, so that fluid can be flushed or primed into the system (and drained) first.

A fluid source 2603 (e.g., a bag of saline) may be attached to the device, so that fluid can be perfused into the bladder before taking a measurement of IAP. In some variations, a system for measuring IAP may include a pressure transducer 2607, as shown. The pressure transducer is connected to the bypass lumen through a fluid pathway via tubing 2661 defining the fluid passageway. Output from the pressure transducer is reported or stored. For example, the pressure may be displayed on a monitor 2665, as shown in FIG. 26.

Figure 27:
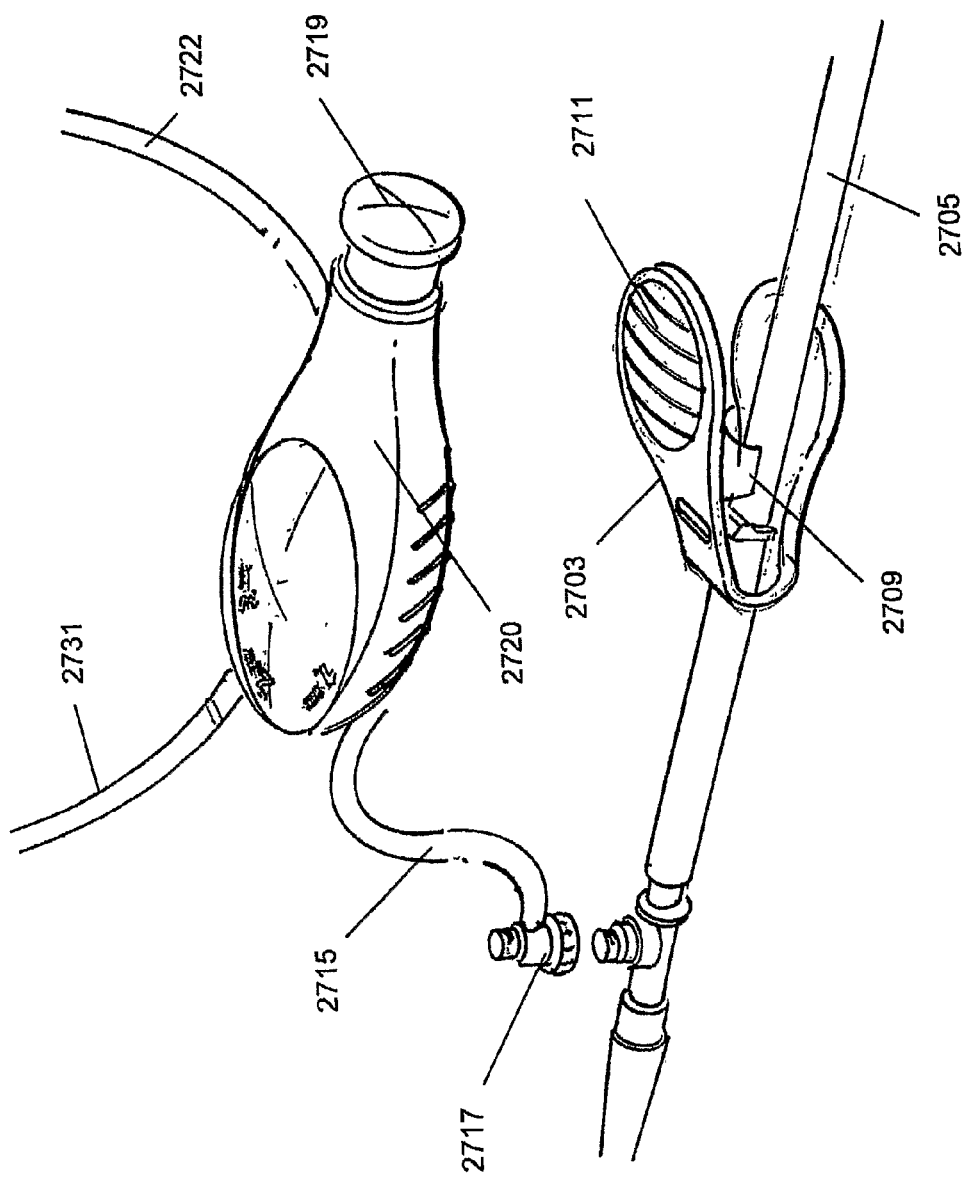
FIG. 27 shows another embodiment of a device for measuring IAP partly attached to a catheter system.

The device for measuring IAP shown in FIG. 27 includes an integrated fluid infuser, however this fluid infuser is not enclosed within the drain tube housing. Instead, a separate drain tube housing 2703 is used to at least partly surround the drain tube 2705. The housing includes a clamp mechanism that is a pinch valve 2709. The pinch valve is activated by pressing a selector 2711 connected to the drain tube housing 2703, and a lock may engage to secure the valve in the closed state, occluding the drain tube.

Figure 28:
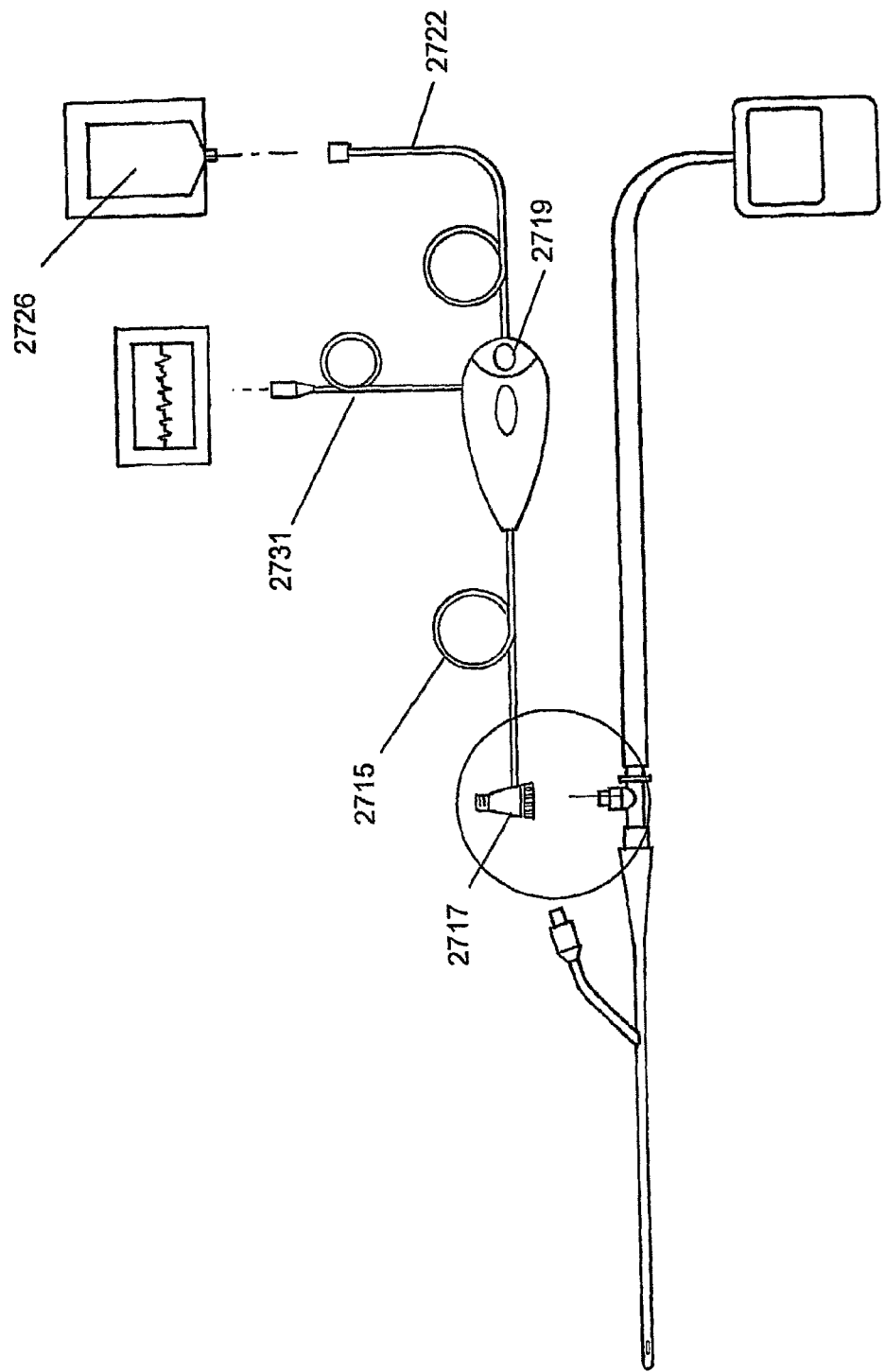
FIG. 28 shows a system for measuring IAP including a device similar to the device for measuring IAP shown in FIG. 27.

The device shown in FIGS. 27 and 28 also includes a bypass lumen within a bypass tubing 2715 that is attached to a sampling port connector 2717 so that the bypass lumen may be put into fluid communication with a lumen of the catheter system. The bypass tubing is also fluidly connected to a second housing at least partly enclosing a fluid infuser. This fluid infuser may be configured as a syringe type fluid infuser, and may include a lever, post, plunger 2719, etc. that can be used to pump fluid into the system. In some variations, the second housing 2703 (not shown in FIG. 28) may also include a pressure transducer fluidly connected with the bypass lumen so that the pressure may be measured. As with any of these devices, the device shown in FIG. 27 may be configured as a single use (e.g., preloaded fluid infuser) or may be configured as multiple use, and may be connected to a fluid source 2726 through a fluid supply line 2722. The device may also be connected to a monitor or recording device by a cable or wire 2731, or it may be wirelessly connected. FIG. 28 illustrates one variation of a system for measuring IAP include the device described in FIG. 27.

The embodiment shown in FIG. 27 also includes an integrated pressure transducer and readout. As mentioned, any variation of the device for measuring IAP may include an integrated pressure transducer and/or readout (e.g., LED). The pressure transducer is located within the housing 2720.

Another embodiment of a device for measuring IAP is shown in FIG. 29A-29F. In this embodiment, the drain tube housing 2901 is shaped to conform to a patient's leg (e.g., a patient's upper thigh region) so that it may be strapped onto the patient's leg. A selector 2903 may be used to control the clamp mechanism, as illustrated in FIGS. 29D-29F. FIG. 29B shows a top view of the device, FIG. 29C shows a side view. The curvature of the bottom of the device may be seen in FIG. 29C. The housing 2901 includes a channel 2917 into which the drain tube 2907 fits. The channel may be arranged in any appropriate portion of the housing. For example, the channel may be open to the bottom of the device (as shown in FIG. 29), the side of the device, or the top of the device (as shown in FIG. 30). The housing also includes a fluid pathway 2905 that can connect to a fluid infuser and/or fluid source. This pathway is typically connected to the bypass lumen so that the selector can control the flow of fluid from the fluid source, before the fluid enters the catheter system when the device is connected to the catheter system via a sampling port connector (not shown). The embodiment shown in FIGS. 29A-29F is similar to the embodiment shown in FIGS. 18A-20, described above. For example, the selector in FIGS. 29A-29F may operate similarly to the selector shown in FIGS. 18A-20.

FIG. 29D illustrates the neutral position of the device, wherein the drain tube is not occluded, but the fluid pathway between the fluid infuser and the bypass lumen is occluded. As described above, the clamp mechanism may include a portion of the fluid pathway between the fluid infuser (and/or fluid source) and the bypass lumen. Thus, the selector may be used to orient the clamp mechanism in the proper orientation so that this fluid pathway is unobstructed. In FIG. 29E, the selector has been rotated so that the drain tube is occluded but the fluid pathway between the fluid infuser and the bypass lumen is not obstructed. The fluid infuser may then be used to apply fluid through the bypass lumen and into the catheter system. FIG. 29F illustrates the configuration in which both the drain tube and the fluid pathway between the fluid infuser and the bypass lumen are occluded. This configuration may be used to take an IAP measurement.

Figure 30A:
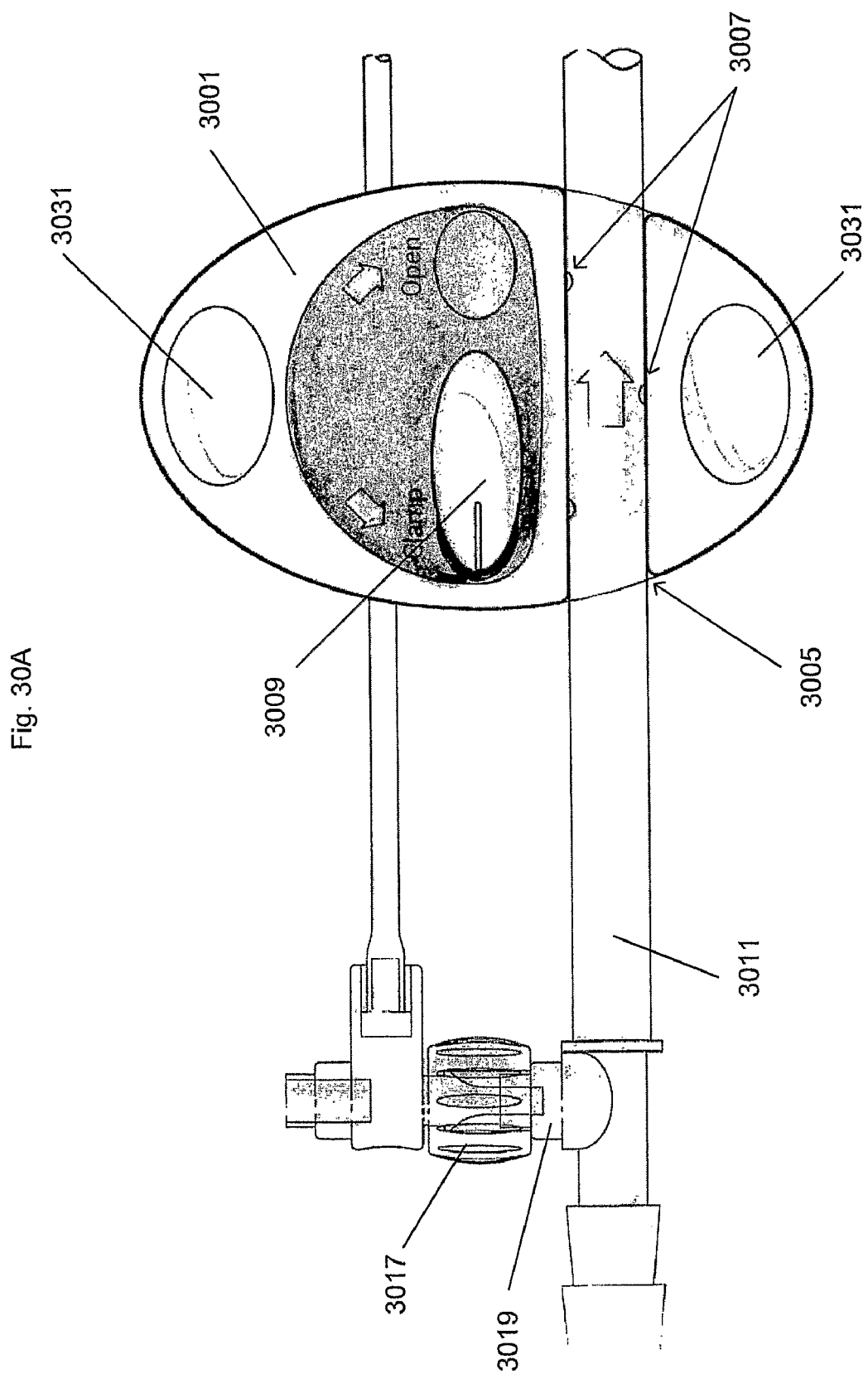
FIG. 30A shows a perspective view of one embodiment of a device for measuring IAP from a catheter system as described herein.

FIG. 30A shows another example of a device for measuring IAP attached to a portion of a catheter system. The device shown in FIG. 30A includes a channel 3005 through the drain tube housing 3001 on the top of the housing, in which a drain tube 3011 may sit. The channel through the housing in which the drain tube may sit is positioned so that the housing slides over the drain tube. As shown in FIG. 30A, a drain tube 3011 may be secured within the channel of the housing by one or more stays 3007, shown here as protrusions, which help to hold the drain tube 3011 within the housing. These stays 3007 may allow the device to accommodate drain tubes of different outer diameters. Stays 3007 may be passive stays (similar to the protrusions shown), or they may be active stays (e.g., including a bias such as a spring element, biased pins, moving disks, etc). Thus, the drain tube 3011 may be easily inserted (and removed) from the housing. Because the opening into the housing is positioned on the upper surface of the housing, the drain tube 3011 may be easily accessed. Once the drain tube 3011 is secured within the housing (e.g., within the channel of the housing), flow through the tube may be controlled by a clamp mechanism (e.g., a pinch valve). In the example shown in FIG. 30, the clamp mechanism is controlled by the selector 3009, shown here as a protruding switch or knob, such as a half-bar knob. As described above, the selector 3009 may also control flow from a fluid source into the bypass lumen and thus into the lumen of the catheter system. The perspective view of the device shown in FIG. 30A also shows two textured grips 3031 (e.g., soft-touch grips) on the surface of the housing. These grips 3031 may help a user position the device, and may also help when moving the selector or when inserting or removing a drain tube.

In some variations of the IAP measurement device, including the embodiment shown in FIG. 30A, the device may be attached to the drain tube by placing the drain tube into the passage through the housing, and the housing may be slid over the drain tube, away from the patient, until it is desired to take an IAP measurement. Once it is time to take a measurement (or a series of measurements), the device may be brought close to the sampling port 3019 and attached with the sampling port connector 3017.

Figure 30G:
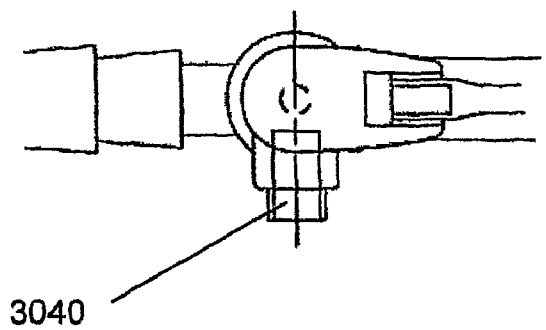
FIGS. 30G and 30H show top and side views of one variation of an auxiliary sampling ports on a device for measuring IAP similar to the device shown in FIG. 30A.
Figure 30H:
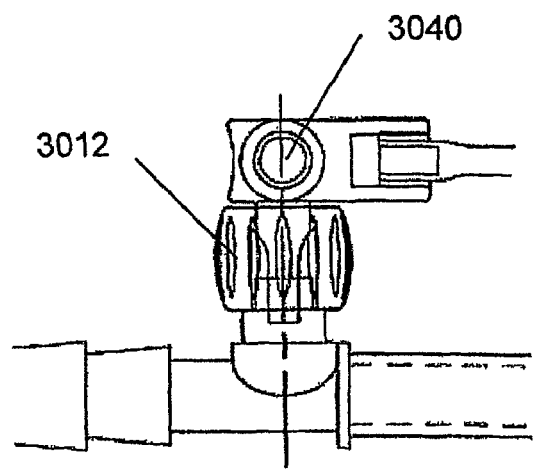

FIG. 30B shows a top view of the device shown in FIG. 30A. The bypass lumen 3033 is connected to a lumen of the catheter system by attaching the sampling port connector 3017 to the sampling port 3019 of a catheter system, as illustrated. The embodiment of the device shown in FIGS. 30A and 30B includes a second or auxiliary sampling port 3040 connected to the sampling port connector 3017, that may allow independent urine sampling even when the IAP measurement system is attached. In some variations, the auxiliary sampling port may be located at ninety degrees (e.g., at a right angle) from the sampling port of the catheter system. For example, the auxiliary sampling port 3040 shown in FIGS. 30G and 30H is located 90 degrees off-axis from the sampling port and the sampling port connector 3017.

FIG. 30C shows a side view of the drain tube housing for the device. As described briefly above, the housing 3001 may be configured to conform to a region of a subject's body, such as a subject's leg. In FIG. 30C, the back of the housing 3061 is curved, and may conform to a subject's leg. The housing 3001 also includes a lip or overhang 3065 which may also make the device easier to manipulate (e.g., grip). Since the device may be used on or near a subject's legs (e.g., between the subject's legs), exposed surfaces of the device, including the selector 3009 may be rounded, smoothed, or padded, to prevent discomfort or harm if they contact the subject.

FIGS. 30E and 30F illustrate the selector 3009 being used to switch the device from one position to another position. In some variations, the device includes simple graphics or instructions (e.g., "open" and "clamp") to indicate the operational state of the device. In FIG. 30E, for example, the selector 3009 is shown in the "clamp" position 3071, in which the clamp mechanism is engaged to prevent flow through the drain tube. This position may also perfuse fluid into the catheter from the fluid source. In FIG. 30F the selector 3009 is shown in the "open" position 3073.

Figure 31A:
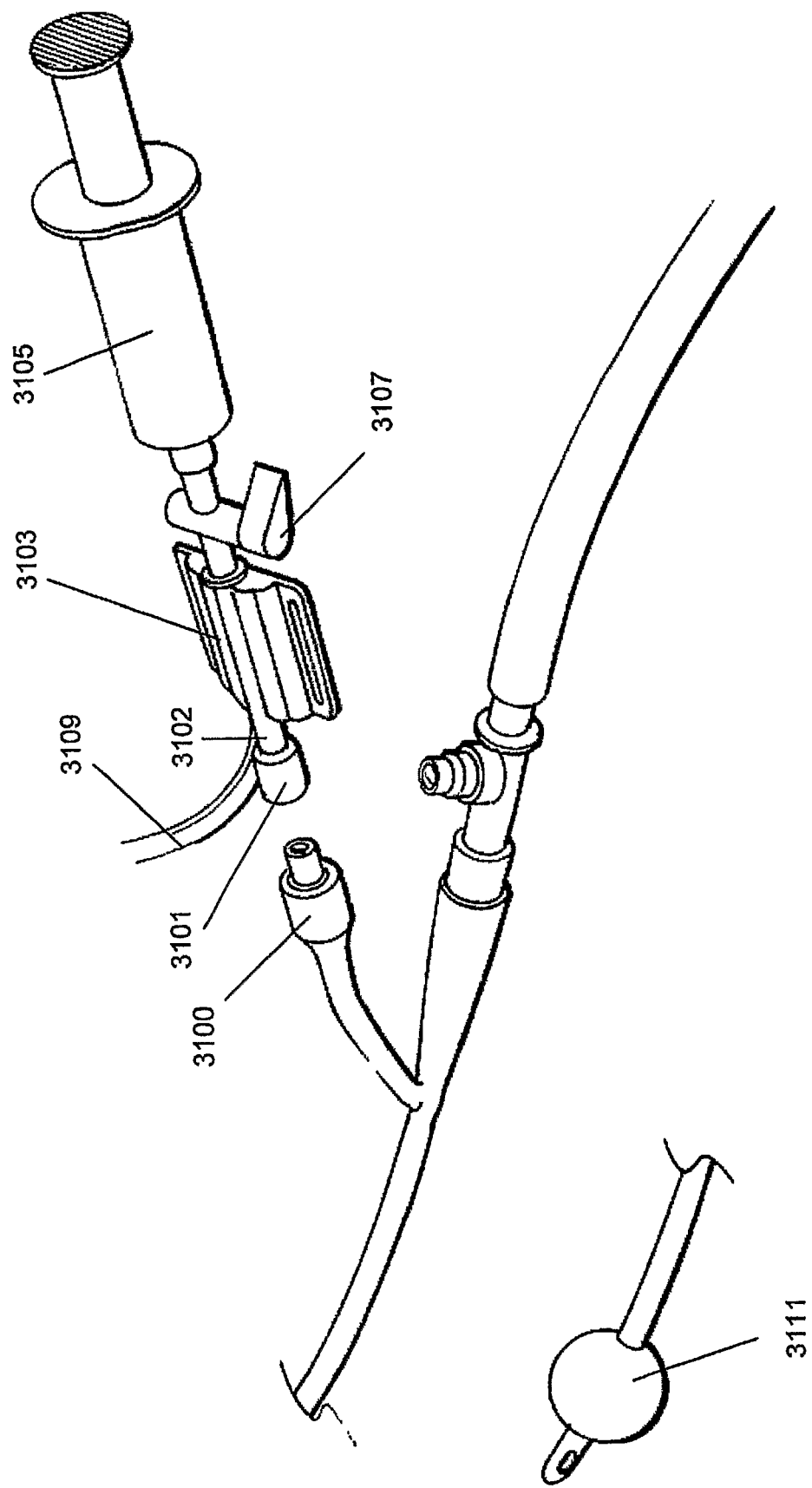
FIG. 31A shows another embodiment of a device for measuring IAP from a catheter system.

The majority of the examples of bypass devices for measuring IAP described herein include a sampling port connector for connecting to a sampling port of a catheter system. However, FIGS. 31-32 illustrate embodiments in which the device is connected to the lumen of the catheter system through a port other than a sampling port. In FIG. 31A a device for measuring IAP is connected to the inflation port. In this embodiment an inflation port connector 3101 connects to an inflation port 3100 of the catheter system. The device includes a bypass lumen within the bypass tubing 3102, and a pressure transducer 3103 that is in-line with the bypass lumen in order to measure pressure within the inflation port (and thus the inflatable member of the catheter). The abdominal pressure may be read from the inflation bulb of the catheter. An inflation source 3105 (e.g., a pump, syringe, etc.) is also placed in fluid connection with the bypass lumen, to provide a pressure source to inflate the bulb of the catheter 3111. A valve 3107 (e.g., a stopcock) may be used to maintain pressure after using the inflation source to inflate the bulb. In operation, the device is attached to the inflation port through the inflation port connector (which may be secured in position to prevent pressure leakage), and the catheter bulb 3111 is inflated using the inflation source 3105. After inflation of the bulb, the proximal end of the bypass lumen is closed (e.g., by the valve 3107), and a pressure measurement reflecting IAP is taken from the pressure transducer 3103. Afterwards, some (or all) of the pressure may be released.

The embodiments shown in FIGS. 31A-32B may also use a different sensing mechanism in which liquid is not added to the bladder. Instead, the air or another gas fills a balloon within the bladder. The balloon may be the anchoring balloon that is present in most Foley catheters 3111 (as shown in FIG. 31A) or a secondary additional balloon 3137 (shown in FIG. 31B). As mentioned briefly above, this embodiment may be particularly well suited to continuously IAP measurement.

Figure 31B:
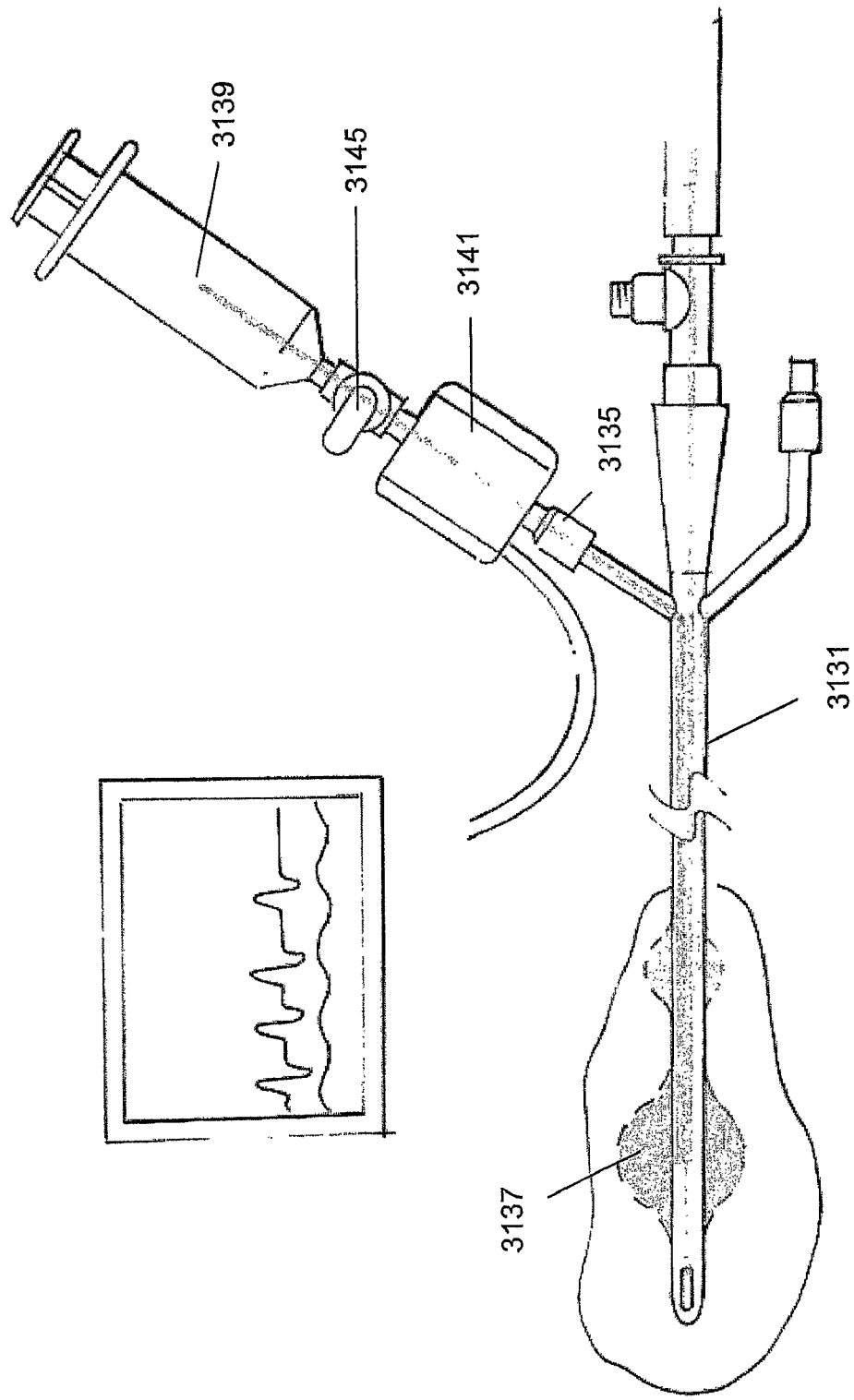
FIG. 31B shows a system for measuring IAP using a 3-way catheter.
Figure 32A:
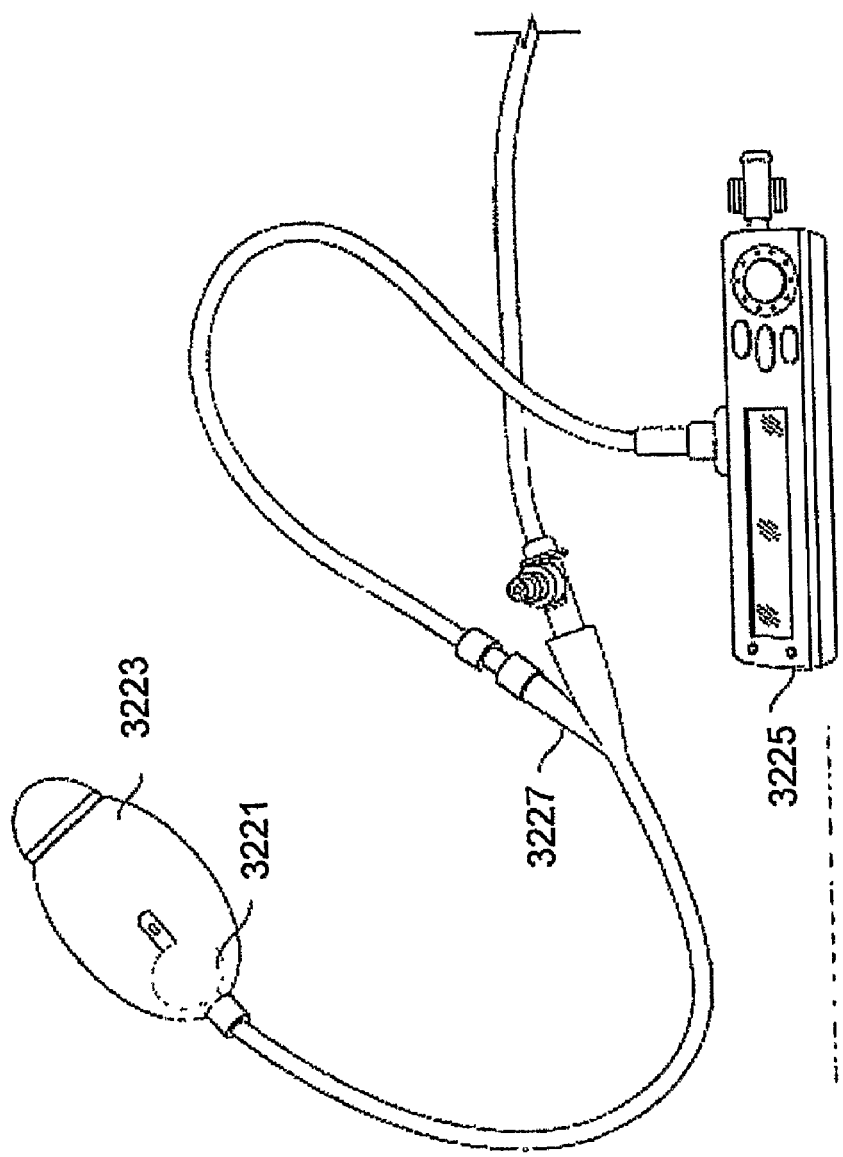
FIG. 32A shows an example of another system for measuring IAP in which the inflation port is used to measure IAP.

FIG. 31B illustrates another variation of a device for measuring IAP, in which the port used to measure pressure is a second fluid lumen of a 3-way Foley catheter 3131. In this embodiment fluid is injected through a bypass lumen that is connected to the second fluid lumen via an entry port 3135. The fluid fills and inflates a second bulb 3137. Fluid is provided by a fluid infuser 3139 and pressure is measured by an in-line pressure transducer 3141. After inflation of the second bulb 3137, a valve 3145 may be used to prevent backflow from the bulb, and pressure may be measured reflecting IAP. The fluid may be removed by opening the valve 3145 and withdrawing the fluid using the fluid infuser 3139 (shown here as a syringe). FIG. 32A shows one example of another system for measuring IAP in which the inflation port is used to measure IAP.

FIG. 32A is an embodiment in which the system utilizes an inflatable element that is expanded inside a patient's bladder to monitor IAP, rather than urine and/or infused fluid. In this embodiment, an appropriately sized/shaped inflatable element (e.g., balloon) mounted on a catheter shaft is expanded inside the bladder of a patient. The resistance felt by the balloon when making contact with the bladder wall is detected through the inflation lumen via a pressure transducer positioned outside of the patient's body. The specific design of the inflatable element can take on various shapes and/or sizes, such as spherical, multi-lobed, oval, longitudinal, etc. Further, the inflatable element can also serve as an anchor to prevent slippage of the catheter out of the patient's bladder (which is the standard function of an inflatable element on the end of a Foley catheter), although in some embodiments, this anchor function is performed by a separate element In FIG. 32A, the inflatable element 3221 has been expanded inside of a demonstrative bladder 3223 to illustrate the functioning of the system. In this particular embodiment, a fluid compensation chamber and pressure sensor 3225 is attached via tubing to the inflation port 3227 and connected to an inflation lumen. The pressure sensor 3225 can be a stand alone pressure sensor, and may be wired to a readout (e.g., display, memory, etc.) or it may be wirelessly connected. In general, a pressure sensor may transmit information (e.g., IAP measurements) to a patient monitor or readout. The inflation port has an inflation valve as known to one skilled in the art. The fluid compensation chamber includes a miniature pump with programmable controls, an embedded circuit to program and control the parameters of operations such as inflation time, sensing time, frequency of on-off cycle, etc., and a fluid reservoir. The fluid compensation chamber compensates for any fluid diffusion through the balloon ensuring a steady baseline. The pump may be battery operated. In the embodiment shown, the drainage and sensing functions are de-coupled, meaning that urine output rate can be independently monitored. Because the sensing element cannot be inflated continuously without compromising the bladder volume, discrete measurements will be generated automatically, as programmed by monitoring needs. The inflatable element at the distal end of the catheter is shown inflated and in contact with the bladder, providing pressure readings to the pressure sensor. As mentioned, the pressure measurement(s) occur in this embodiment simultaneously with the drainage of urine from the bladder as the urinary lumen of the catheter remains open and in fluid communication with an attached drain tube. The proximal end of the catheter is attached to a proximal connection member as described above such that sampling of urine may also be performed simultaneously with the pressure reading(s).

Figure 32B:
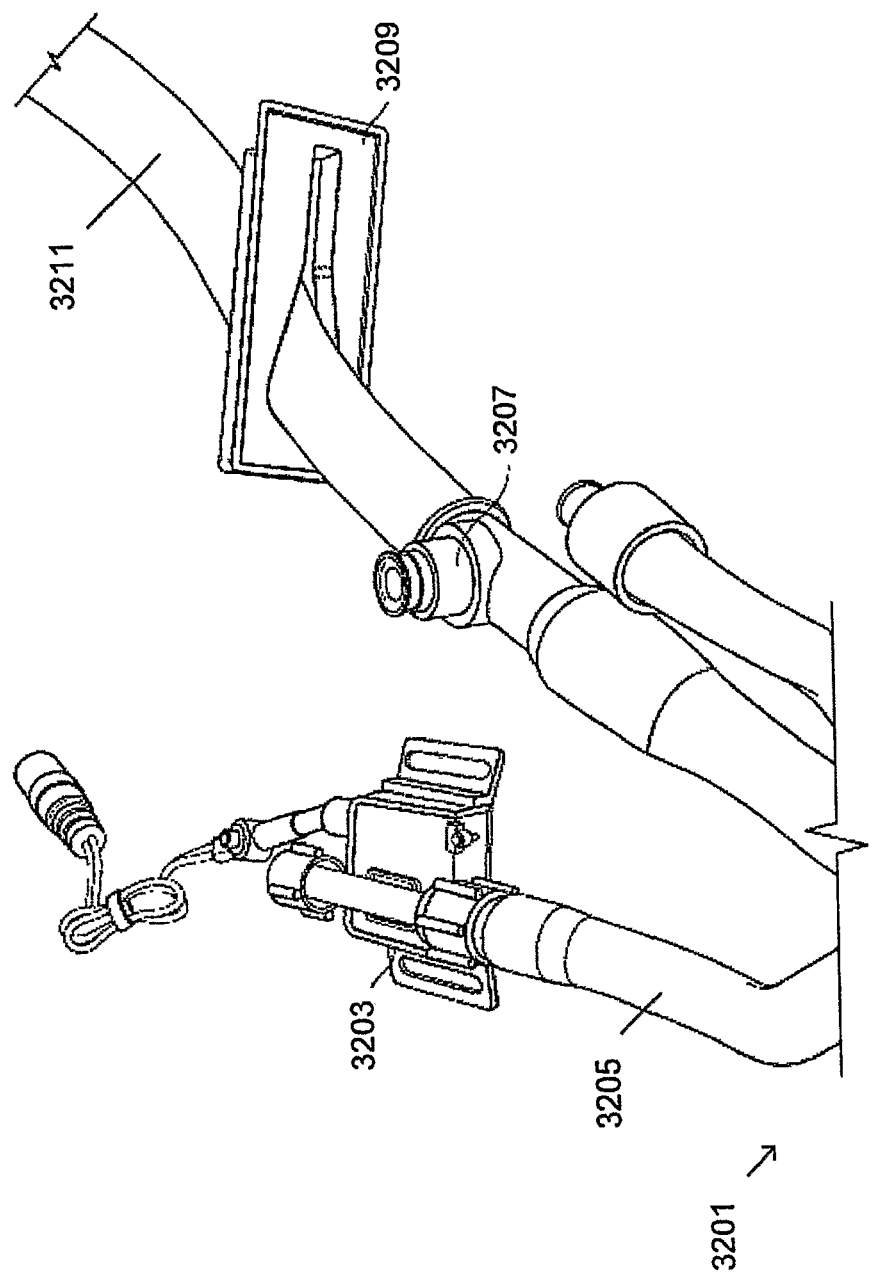
FIG. 32B shows another embodiment of a device for measuring IAP using a 3-way catheter.

Another example of a urinary catheter bypass IAP measurement device for use with a 3-way Foley catheter is shown in FIG. 32B. For example, a 3-way catheter (e.g. 3-way Foley catheter) may include an additional fluid lumen through which the bladder may be accessed. Thus, a bypass IAP measurement device may be configured to fluidly connect to the additional fluid lumen within the catheter to add additional fluid and take pressure measurements when the drainage tube is occluded. Any of the examples for occluding the drainage tube (e.g., housings, clamp mechanisms, etc.) may be used with this variation as well. FIG. 32B shows one embodiment of such an IAP monitoring system using a three-way Foley catheter 3201 such that a pressure transducer 3203 is permanently connected to a third proximal branch 3207 in fluid communication with a third catheter lumen. In this embodiment, a pinch vice 3209 is utilized to stop the flow of urine through the drainage tube 3211 connected to the proximal connection member. When an IAP measurement is desired, the drainage tube is clamped and fluid, such as saline, is infused through the sampling port and into the bladder utilizing a fluid infusion device (again shown here as a syringe). When a sufficient amount of fluid has been infused (e.g., approximately 40-60 mL), the third lumen, having a distal opening in the bladder, fills with fluid so that an IAP measurement can be taken using the pressure transducer 3203.

FIG. 33A-33C shows a device for measuring IAP that may be attached to an in-dwelling urinary catheter system to re-direct the drainage pathway of the catheter system without use of a port (e.g., sampling port). This device punctures a portion of the urinary catheter system to provide access to the lumen of the catheter system to a fluid pathway that includes a valve so that urine drainage can be shut off in favor or adding additional fluid from a fluid infuser (and/or fluid source) and IAP measured. FIG. 33A shows a perspective view of this device. The housing 3301 surrounds a fluid passageway 3305 and a valve 3307. The housing also receives fluid from a fluid supply line 3311. A selector 3315 may be configured to switch the valve and prevent draining of from the catheter or allow the application of fluid from the fluid infuser.

FIG. 33B shows that the housing may include a first (e.g., upper) section and a second (e.g., lower) section which may be applied over the catheter system (e.g., a portion of the drainage tube, as shown). The housing includes at least two puncture tubes 3330, 3330' in fluid communication with the inner lumen of the fluid passageway 3305. The housing also includes a pinch valve 3350, 3350' that completely pinches off the drain tube, requiring that flow through the catheter system pass through the fluid passageway 3305 instead. Once the device has been applied, it may be permanently left on the catheter system to prevent leakage. A pressure transducer may also be connected to the fluid supply line 3311 to measure IAP.

Urinary Catheter Integrated IAP Device

FIGS. 34-44 illustrate integrated IAP monitoring systems, in which the mechanism that occludes the drain tube and permits infusion of fluid into the urinary catheter is integral to the catheter system. In the embodiments illustrating such a tailored system, the aforementioned mechanism is typically an integral valve that is positioned in the drainage path of the IAP system (e.g., in a proximal section of a connection member, including a sampling port, the connection member being attached at its distal end to a Foley catheter and at its proximal end to a drain tube).

IAP may be measured using readily available equipment found in the critical care environment, such as systems that are designed to provide measurements of bladder pressure. In certain examples provided herein, an IAP system can be created by adding component(s) to form an operational closed urinary catheter system, allowing IAP measurements to be taken without breaking the closed system and with minimal interruption of the system. In many of these integrated IAP devices, the system is assembled to form a "closed" system before insertion into a subject. This may be contrasted with the bypass devices described above. For example, an integrated IAP device may include an integrated connection member (also referred to as a "connection member") that has a lumen and includes a valve or clamp mechanism for occluding flow draining through the catheter into the lumen of the integrated connection member. The connection member may also include a connector (e.g., a friction fit connector) at a distal end for fluidly connecting the lumen of the catheter (e.g., a Foley catheter), and a connector at a proximal end for fluidly connecting to a drain tube or directly to a waste container.

Figure 34:
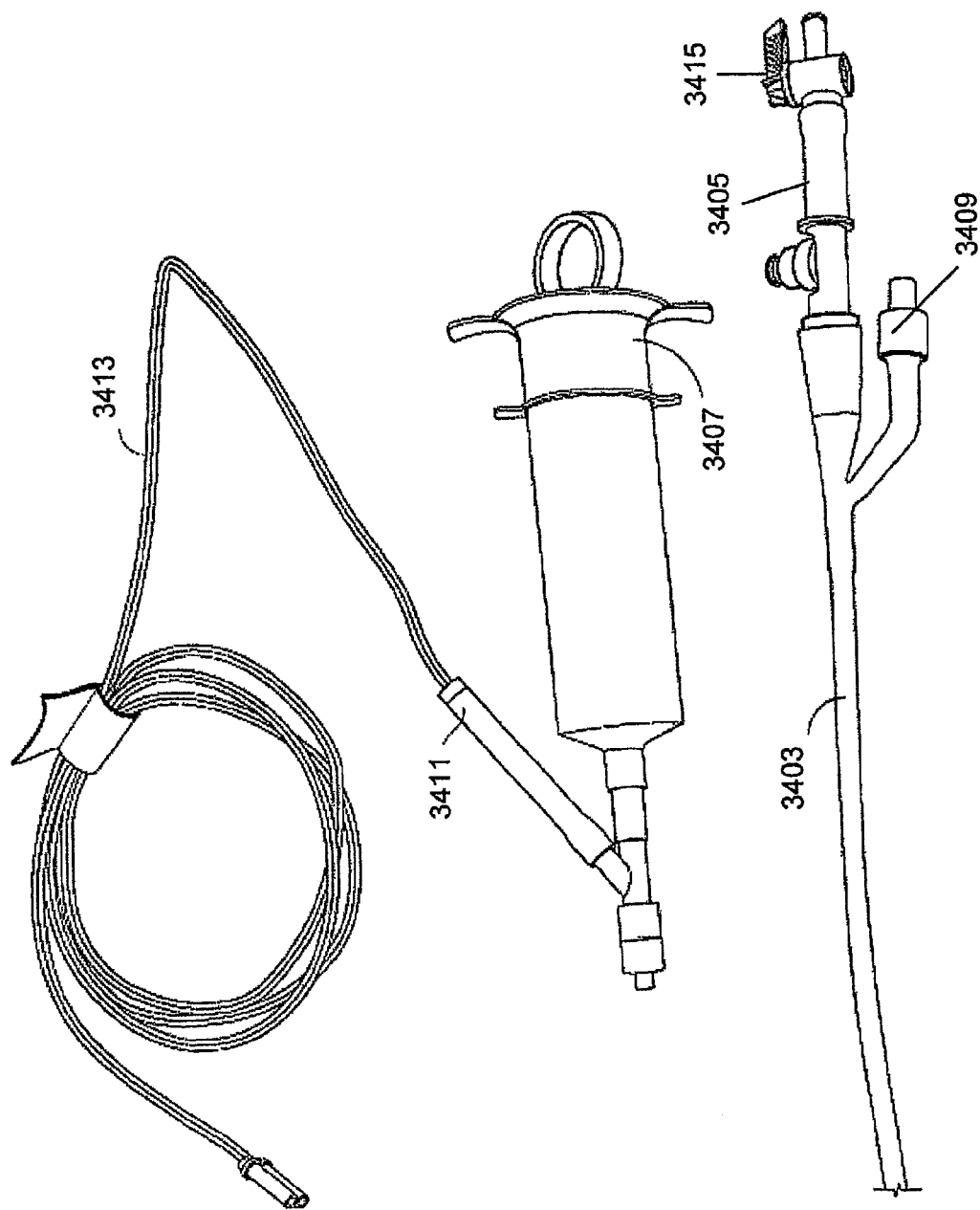
FIG. 34 shows another embodiment of an IAP monitoring system.
Figure 35:
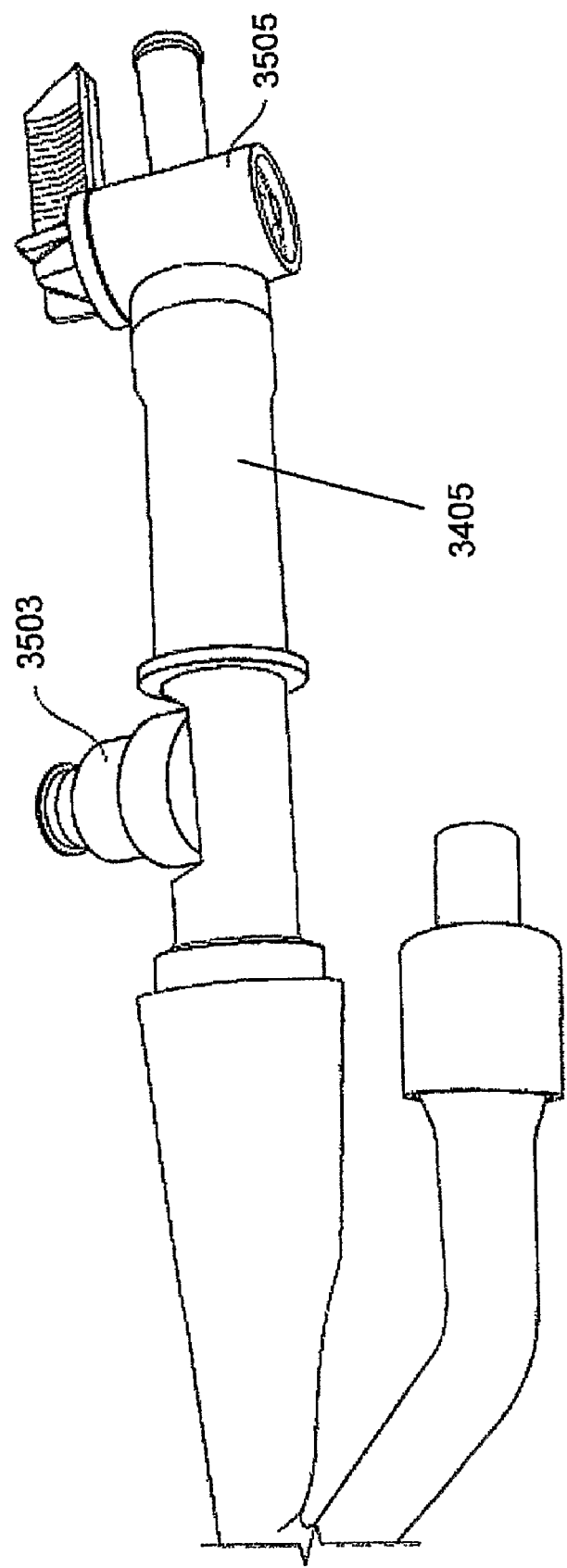
FIG. 35 shows a close-up view of the proximal connection member of FIG. 34.
Figure 36:
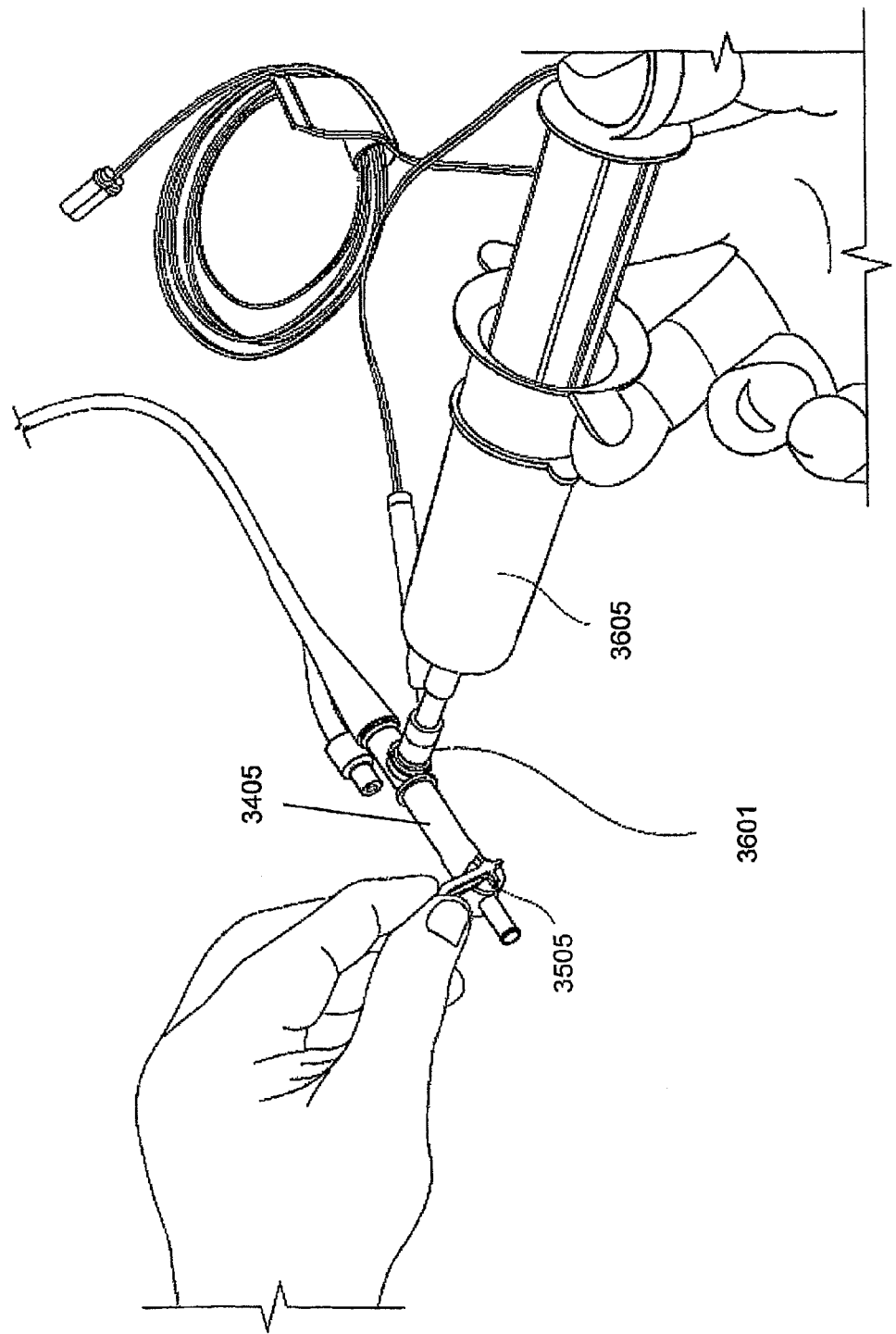
FIG. 36 illustrates the components of FIG. 34 partially assembled for use in obtaining an IAP measurement.

An example of such a closed urinary drainage system (prior to insertion in a patient) is shown in FIGS. 34-36, in which a Foley catheter system with a connection member 3405 and a stopcock 3415 is shown. In such a system, a drain tube (not shown) is connected to the distal end of the connection member 3405 (distal to the stopcock 3415), which typically leads to a urine collection device such as a bag or container. In urinary catheter systems without an integral member, such as a stopcock, to occlude the drain tube, a pinch vice or clamp mechanism can be utilized as described more fully, below. FIG. 34 shows components for one embodiment of an IAP monitoring system, including a two-way Foley catheter 3403 with a proximal connection member 3405, a fluid infusion device 3407, a pressure transducer 3411 and a monitor cable 3413. FIG. 35 is a close-up view of the proximal connection member 3405, showing a sampling port 3503 with valve and a stopcock 3505 positioned proximal of the sampling port. One variation of a sampling port valve is described in U.S. Pat. No. 6,651,956 to Miller, which is incorporated by reference into this application as if fully set forth herein. The proximal connection member 3405 is attached to a first lumen of the Foley catheter utilized for draining urine from a patient. The second proximal catheter branch 3409 leads to an inflation lumen of the catheter as is known to one of ordinary skill in the art. As shown in FIG. 34, the pressure transducer 3411 is attached to the fluid infusion device 3407 and the monitor cable 3413 is attached to the pressure transducer 3411 such that a pressure reading can be displayed to the user. Of course, other output devices for the purpose of providing a pressure reading (or for various other reasons known to one of ordinary skill in the art) could be attached to the pressure transducer instead of, or in addition to, a monitor.

In practice, the distal end of the Foley catheter connected to the integrated IAP measurement device is placed into a patient's bladder, and the catheter secured by inflating a distal balloon by infusing fluid through the inflation lumen of the catheter (which prevents the distal end of the catheter from slipping out of the bladder). The stopcock 3505, which is in the closed position at the outset and has a proximal end connected to a drainage tube, is then opened to permit drainage of urine present in the bladder to a collection chamber/bag/container. An IAP measurement may be taken by blocking drainage of urine, and measuring pressure of fluid within the bladder. For example, the stopcock 3505 is closed (e.g., by turning the handle of the stopcock), and the fluid infusion device, which may include a proximal male luer fitting for insertion into the valve in the sampling port, is attached to the sampling port. Fluid, such as saline, is then infused into the bladder and an IAP measurement is then taken, as depicted in FIG. 36. In FIG. 36, the proximal connection member 3405 is shown without connection to a drain tube. Fluid is added to the catheter (and thus the bladder) by the fluid infuser 3605. The fluid infuser shown in FIGS. 34-36 is a syringe that has been pre-loaded with a fluid (e.g., saline) for injection. The fluid infuser attaches to the sampling port of the catheter via a sampling port connector 3601 (e.g., a syringe interface). The integrated system shown in FIGS. 34-36 permits multiple IAP measurements to be taken without subjecting the patient to unnecessary risks attendant with the opening of a previously closed system (i.e., an IAP measurement is taken without breaking the closed urinary catheter system). In one embodiment, the stopcock is ergonomically designed to provide patient comfort.

Figure 37A:
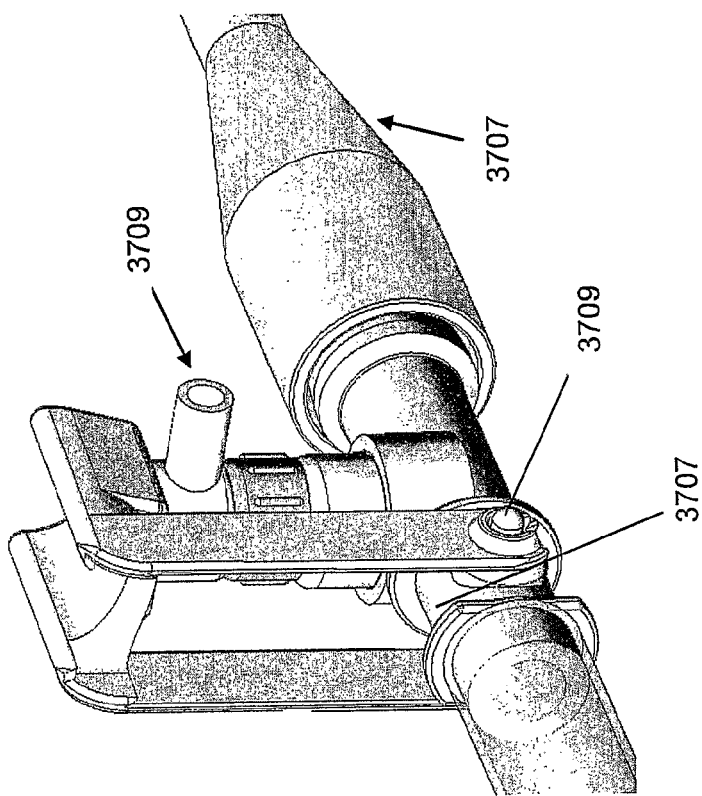
FIGS. 37A and 37B show one embodiment of an integrated device for measuring IAP in an inactivated and activated state, respectively.
Figure 37B:
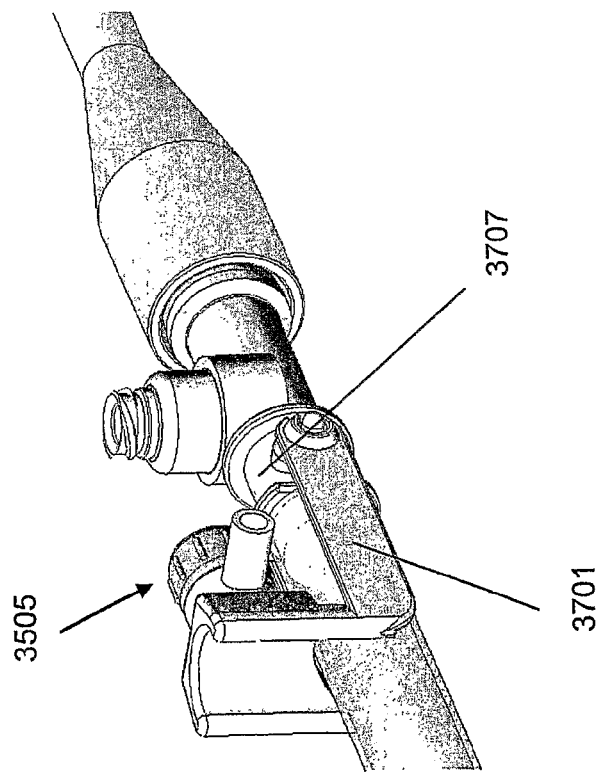
Figure 38A:
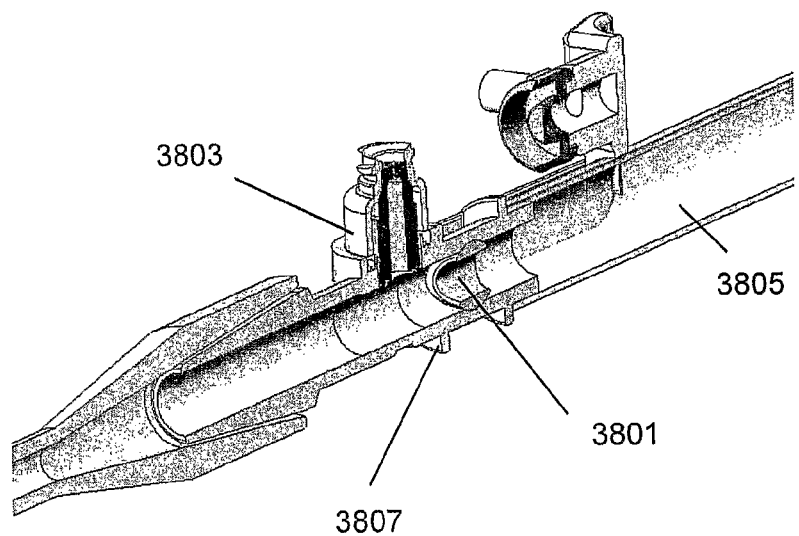
FIG. 38A and FIG. 38B show cross-sections thorough a device for measuring IAP similar to the device shown in FIGS. 37A and 37B, respectively.
Figure 38B:
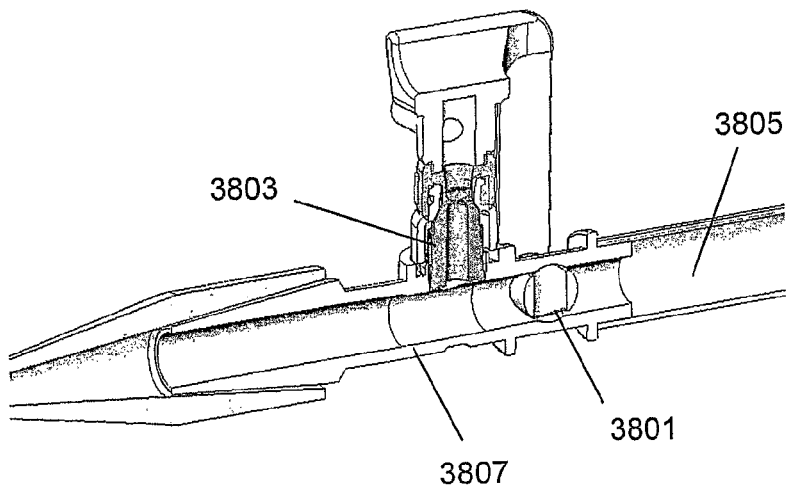

FIGS. 37A-38B illustrate one embodiment of an IAP monitoring system including an integral valve. FIG. 37A shows the rest state and FIG. 37B shows an activated state for this embodiment, in which the integral valve is positioned in a proximal section of a sampling port connection member adjacent a proximal end of the connection member that is attached to a drain tube. The integral valve includes a valve member residing within a fluid flow path of the connection member 3707, the valve member being attached to a spindle 3709, which extends to the external surface of the connection member for attachment to an activation arm 3701. The activation arm 3701 is shown as an "L" shape member in FIGS. 37A and 37B, having at its proximal end a sampling port connector 3705 including an auto valve similar to the embodiments discussed above. Movement from the rest state 37A to the activated state 37B includes movement of the activation arm from a rest position on top of the drain tube to an activated position where the auto valve is brought into contact with the sampling port and connected thereto (e.g., in the illustrated embodiment by threading the auto valve to the sampling port). FIGS. 38A and 38B show a longitudinal cross-section of the system of FIGS. 37A-37B. In this view, the integral valve 3801 can be seen positioned between the urine path of the Foley catheter and sampling port connection member 3803 and the drain tube 3805 to control the flow of urine or fluid through the connection member 3807. As the activation arm 3701 is moved from a rest position to an activated position, the integral valve 3801 transitions from an open position to a closed position to occlude the pathway from the connection member 3807 to the drain tube 3805.

Figure 39A:
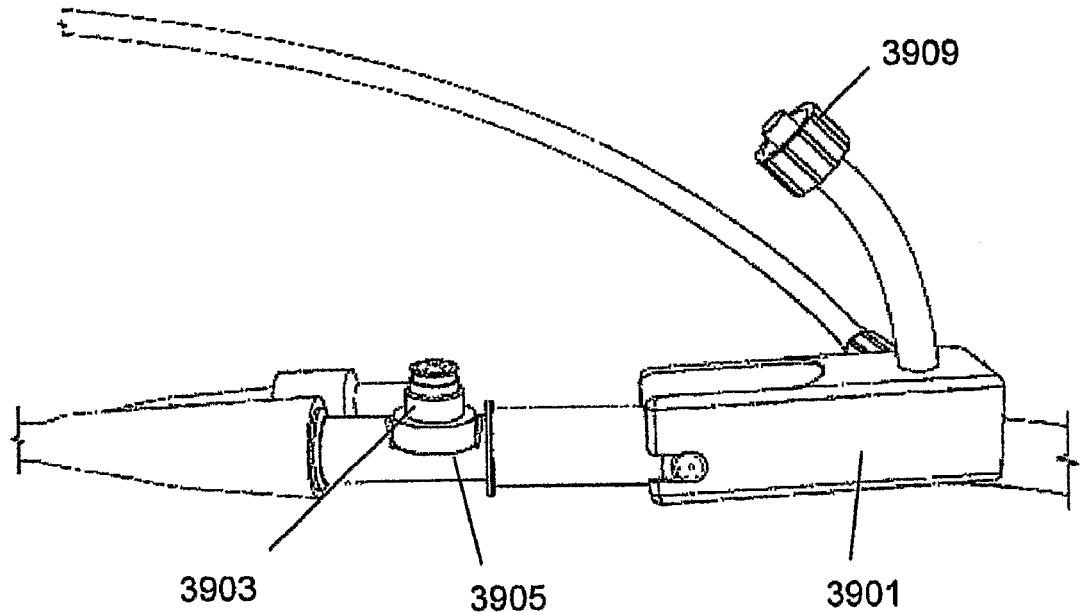
FIGS. 39A and 39B show another embodiment of a device for measuring IAP in an inactivated and activated state, respectively.
Figure 39B:
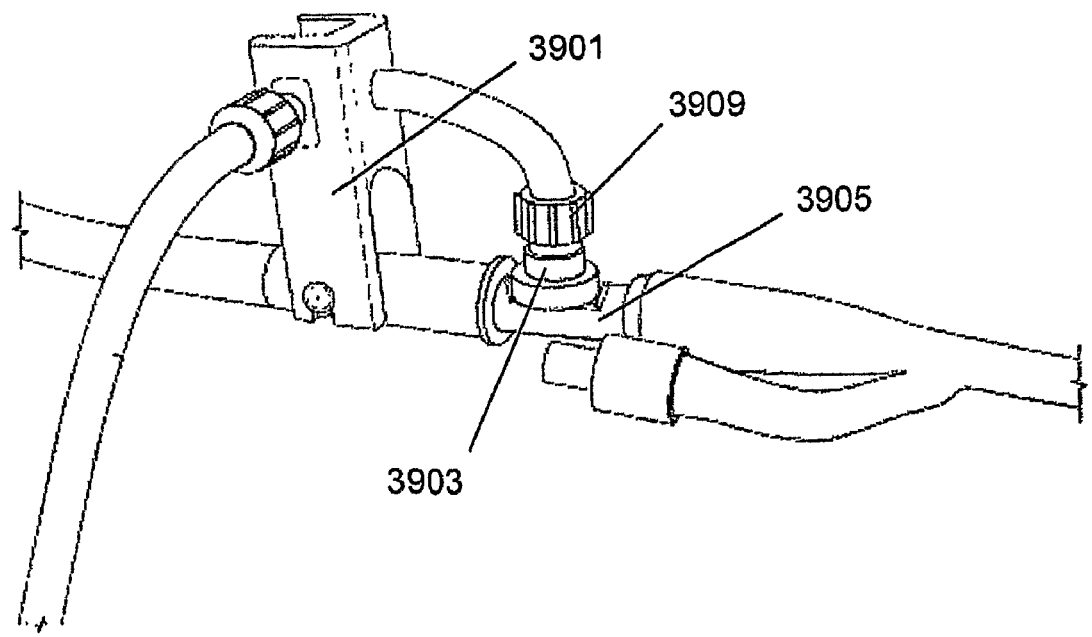

FIG. 39A shows another embodiment of the type of device illustrated in FIGS. 37A-38B in both a rest state (FIG. 39A) and an activated state (FIG. 39B). In this embodiment, the activation arm 3901 has a slightly different configuration. These devices may also include an auxiliary sampling port, as described above. The first sampling port 3903 is typically aligned on the connection member 3905 to interact with the sampling port connector 3909, while the second sampling port may be positioned in another location on the system (e.g., in the drain tube) to enable sampling of urine while the system is activated for pressure monitoring (i.e., to enable urine sampling without having to detach the auto valve from the first sampling port). It should be noted that while the above-described embodiments are discussed with respect to the integral valve being positioned in a sampling port connection member, other embodiments are also possible. For instance, in another embodiment, a two-piece connection member includes a first portion that carries the sampling port, which can be connected to the urinary catheter, and a second portion that carries the release valve and activation arm, which can be connected to the drain tube. This two-piece connection member can be assembled and permanently or releasably locked through various mechanisms known to one skilled in the art prior to use of the system. In another embodiment, a release valve can be placed within the drain tube itself or in a connection between the drain tube and a fluid flow conduit or tubing leading to other components of an IAP monitoring system.

In some of the integrated IAP systems mentioned above (i.e., a system in which component(s) are incorporated into an operational closed urinary catheter system and a tailored system containing an integral valve), in order for an IAP measurement to be taken, drainage of urine is least temporarily suspended (e.g., by clamping a drain tube) and fluid is infused through the catheter and into the bladder. In one embodiment, the functions of suspension of urine drainage and fluid infusion is performed in a single step, through use of an activation member or the like.

Figure 40:
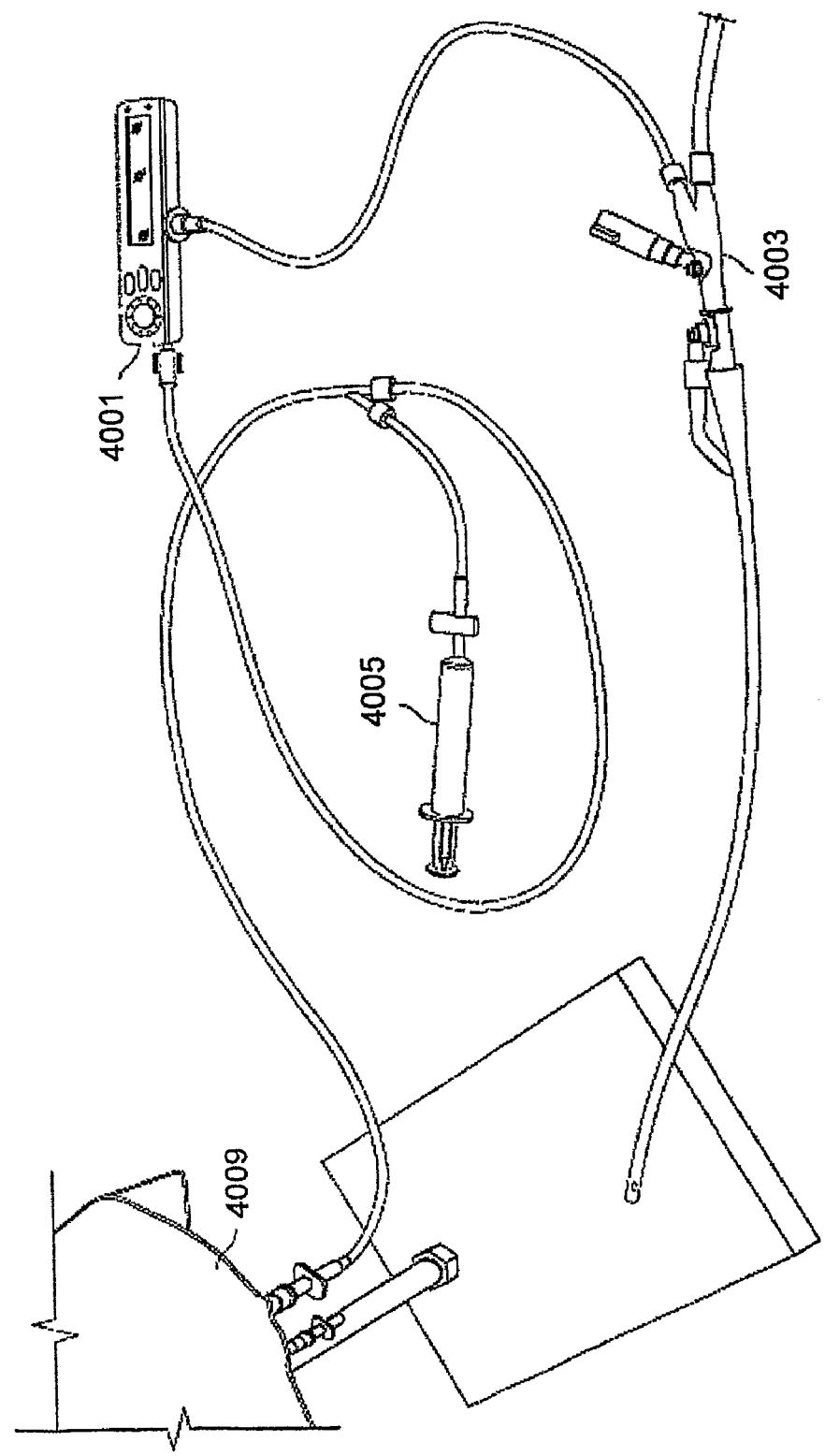
FIG. 40 shows another embodiment of an IAP monitoring system, including a combination pressure transducer and display unit, as described herein.
Figure 42:
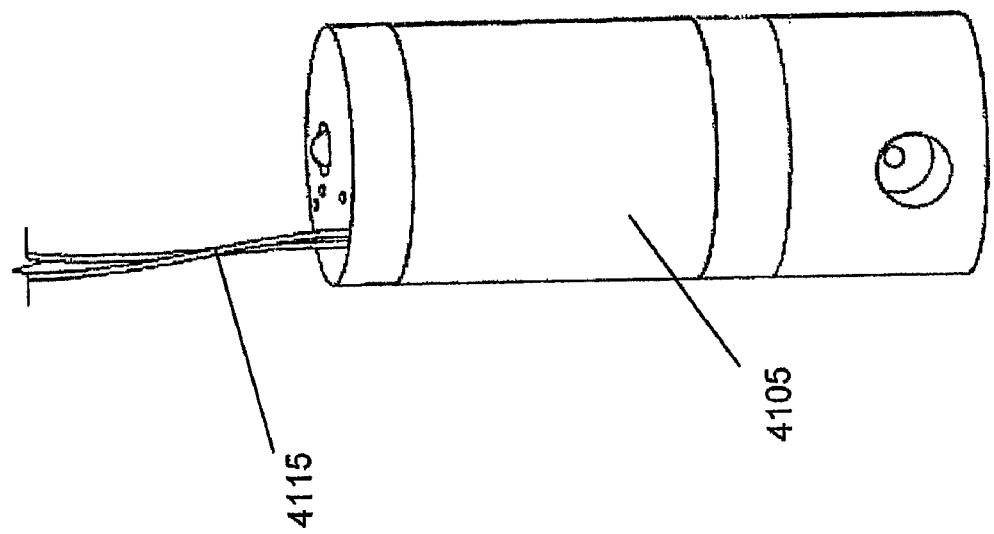
FIG. 42 shows the electronic valve from the system of FIG. 41.

FIG. 40 is another embodiment of an IAP monitoring system, including a combination pressure transducer and display unit. In this embodiment, the proximal end of a proximal connection member with sampling port as described above has connected thereto a two-way valve 4003 member. The two-way valve member has attached thereto a drain tube and a fluid conduit in communication with the pressure transducer and display unit 4001. In a rest state, the valve is open to the drain tube and closed to the fluid conduit. When an IAP measurement is desired, the valve is positioned in an activated state to be closed to the drain tube and open to the fluid conduit. The change in position can be done manually, automatically, remotely, electronically, etc., as one skilled in the art would appreciate. A fluid infuser 4005 (e.g., infusion syringe) is connected in-line with a fluid source 4009 (e.g., saline bag or other fluid source) to meter the fluid and infuse the fluid to the pressure transducer and display unit and onto the fluid conduit and eventually the inserted catheter.

In another aspect of the invention, an IAP monitoring system is designed to be continuous and automatic. FIGS. 41-44 illustrate schematically a few examples of different embodiments of such systems.

Figure 41:
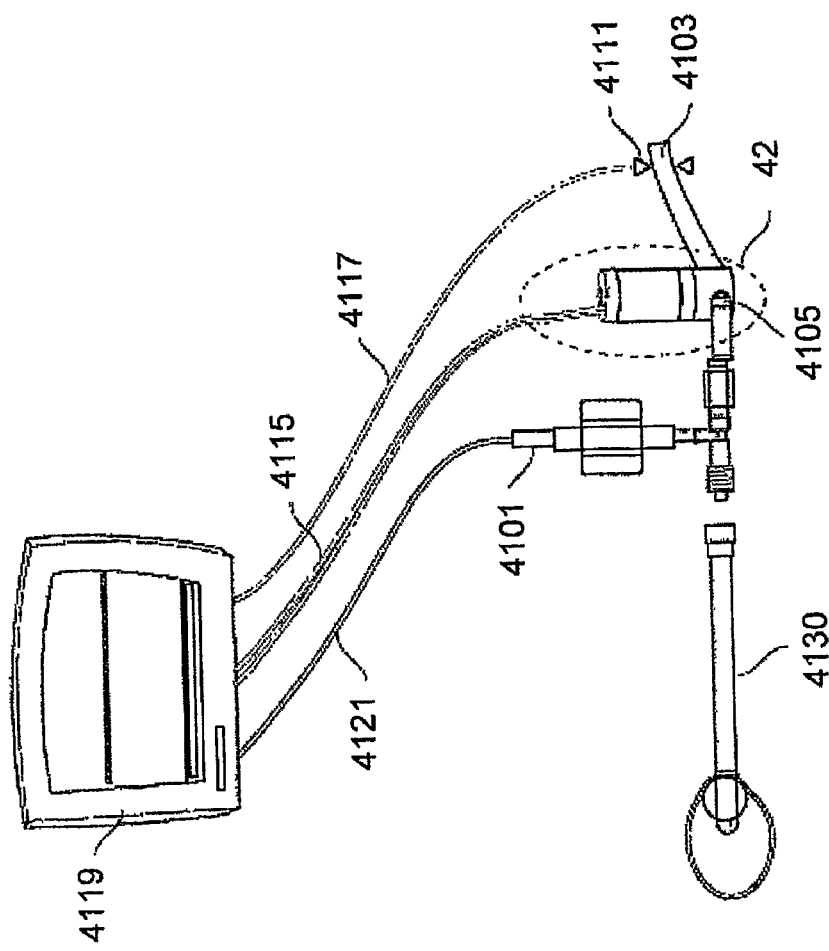
FIG. 41 is a schematic of an embodiment of an IAP monitoring system in which an inline pressure transducer 4201 is mounted in the urinary drainage line.

In one embodiment, an IAP monitoring system utilizes a patient's urine as the primary method for sensing and measuring IAP. FIG. 41 is a schematic of one embodiment of an IAP monitoring system in which an inline pressure transducer 4101 is mounted in the urinary drainage line. The device shown in FIG. 41 may include a programmable valve to regulate fluid flow to a drain tube. Such an electronically controlled valve 4105 (shown in more detail in FIG. 42) integrated in the urinary drainage line (e.g., in a connector element attached to the drain tube 4103, in the drain tube itself, etc.) automatically restricts the flow of urine to increase bladder pressure, which pressure is detected by the pressure transducer in fluid communication with the bladder. The electronic valve 4105 can be preset as a function of urine production rate to ensure that urine being produced by the kidneys is available to act as the medium of pressure sensing. In one embodiment, a urine detector 4111 is connected to the drain tube 4103 (although the urine detector could be placed at any point along the urinary drainage line) to measure the rate of urine production.

Any appropriate pressure transducer may be used with any of the variations of devices and methods for detecting IAP as described herein. Although a mechanical pressure transducer is shown and described in connection with many of the embodiments discussed herein, it should be noted that other detection methods are contemplated, such as a fiber optic pressure transducer probe used either alone or with a fiber optic temperature probe. The fiber optic probe may be placed at any appropriate point within the system from the bladder to the exterior of the patient. For example, the fiber optic probe may be positioned within the tip of the catheter, the balloon interior, the lumen of the catheter shaft, in-line with the drainage tubing, etc. In one embodiment, the fiber optic pressure transducer attaches to a monitor which continually checks the pressure. If necessary, the system will cycle to fill the bladder, monitor pressure for a given period, allow the bladder to drain, and repeat. In another embodiment, the fiber optic probe is integrated within the catheter wall and positioned in the tip of the catheter to sense bladder pressure, connecting to an external signal conditioner that processes the signal and continually displays the bladder pressure.

FIG. 43A is a schematic of an embodiment of an IAP monitoring system similar to that of FIG. 41, but with a miniaturized sensing element 4303 integrated into the shaft of the catheter 4301 at a distal end. FIG. 43B shows one example of a sensor 4303 in more detail. The system of FIG. 43A may be used for continuous and automatic IAP monitoring. The sensor may communicate via RF 4315 to an external device 4311. The sensor 4303 is positioned in the bladder when the catheter 4301 is inserted and because the bladder is a closed cavity, the ambient pressure changes within the cavity correlate to the compression of surrounding organs. Thus, the sensor has the ability to monitor IAP trends. In this embodiment, the sensor is based on micro-electromechanical systems (MEMS) technologies and is controlled by radio frequency (RF), thereby minimizing wires and connections 4363 to provide a solid state solution. In particular, a base unit 4311 located external of a patient's body is attached to a patient monitor 4321 and is programmed to send signals via RF 4315 to the sensor 4303 and receive signals 4315 from the sensor 4303, which signals are displayed on the monitor 4321. The system may also include an electronically controlled valve 4331, and a urine detector 4341 connected to the drain tube 4335. Of course, as known to one skilled in the art, other means of sending and receiving signals are also possible and are contemplated herein.

Figure 44:
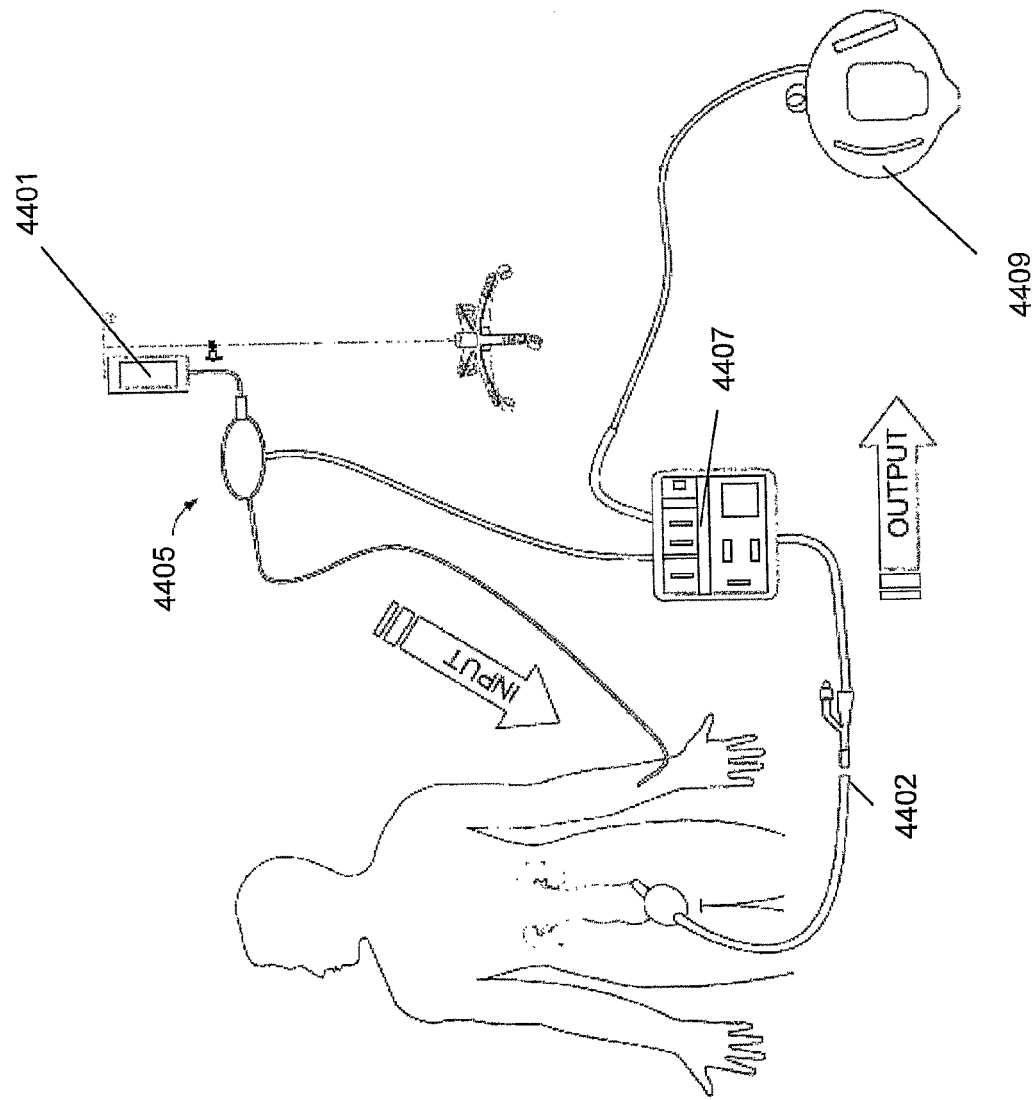
FIG. 44 shows another embodiment of an IAP monitoring system as described herein.

FIG. 44 is a schematic of another embodiment of an IAP monitoring system, designed to be used, for instance, in cases of trauma in which fluids may be continuously infused. The system shown in FIG. 44 may be used for continuous and automatic IAP monitoring, including monitoring infusion of IV fluids 4401 to a patient with respect to urine output. This system links the fluid infusion and urine output for continuous and automatic monitoring of the patient. In this embodiment, a sensor-based (e.g., drop counter 4405, flow sensor, etc.) linked system is utilized to track fluids administered to the patient and urine produced by the patient. The patient is catheterized with a Foley catheter 4402 and urine is collected in a waste (drain) bad 4409. In the context of IAP, because fluid loading may result in elevated IAP levels, a closed loop feedback of fluid input/output (I/O) module with IAP measurement 4407 confirms where the fluid is being directed (i.e., urinary excretion or tissue absorption). In one embodiment, an alarm is connected to the system to indicate to a clinician elevated IAP levels in a patient. In another embodiment, a regulating system is incorporated into the IAP monitoring system to stop or slow down the fluid infusion rate upon reaching a certain IAP level or ratio of infused fluid to excreted urine. In one embodiment, the hardware component of the system incorporates a software algorithm that is programmed to manage the rates, ratios, etc. and to regulate fluid infusion line via, for example, a transducer. The specific design features of this system can be tailored to particular clinical patient monitoring protocols and user preferences.

IAP System

FIGS. 45A to 47C illustrate examples of systems for measuring IAP using a device as described herein.

In FIGS. 45A to 45D, the exemplary system includes a device for measuring IAP similar to the urinary catheter system bypass devices described above (particularly the embodiment shown in FIGS. 30A to 30F). The system shown in FIGS. 45A-45D includes a urinary catheter system bypass device configured to connect to a urinary catheter system. The urinary catheter system bypass device includes a drain tube housing 4501, a bypass lumen enclosed within a first fluid channel 4503 (shown here as a tube), a sampling port connector 4509, and a selector 4505.

Figure 45A:
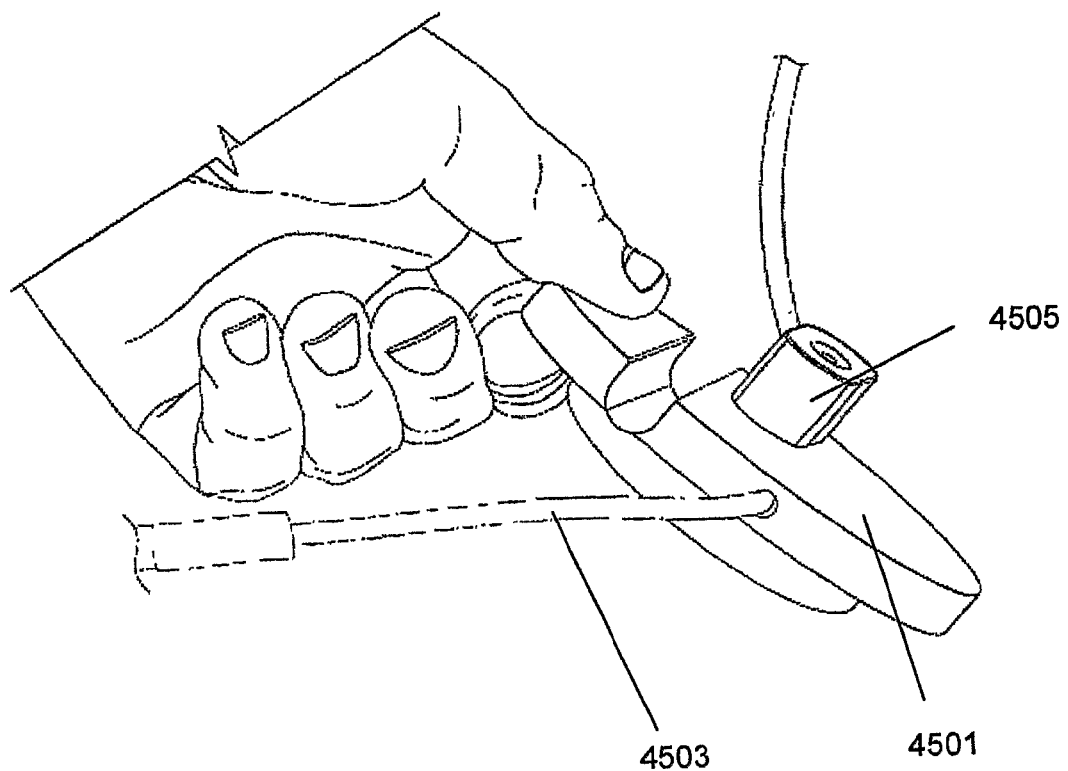
FIG. 45A-45D illustrates an exemplary system having a device for measuring IAP as described herein.

The first fluid channel 4503 passes completely through the housing 4501, and the housing may be slid along the tubing enclosing the fluid channel, allowing the housing to be positioned, as illustrated in FIG. 45A. The housing also encloses a clamp mechanism (not shown) controlled by the selector 4505. The selector in this variation may control the clamp mechanism (or more than one clamp mechanism) to occlude the drain tube, and/or to open or occlude the bypass lumen, permitting application of fluid from a fluid supply (e.g., via a fluid infusion device), and/or measurement of IAP using a pressure transducer. Thus, the system typically includes both a fluid infusion device and a pressure transducer, which may be connected to the bypass lumen.

Figure 45B:
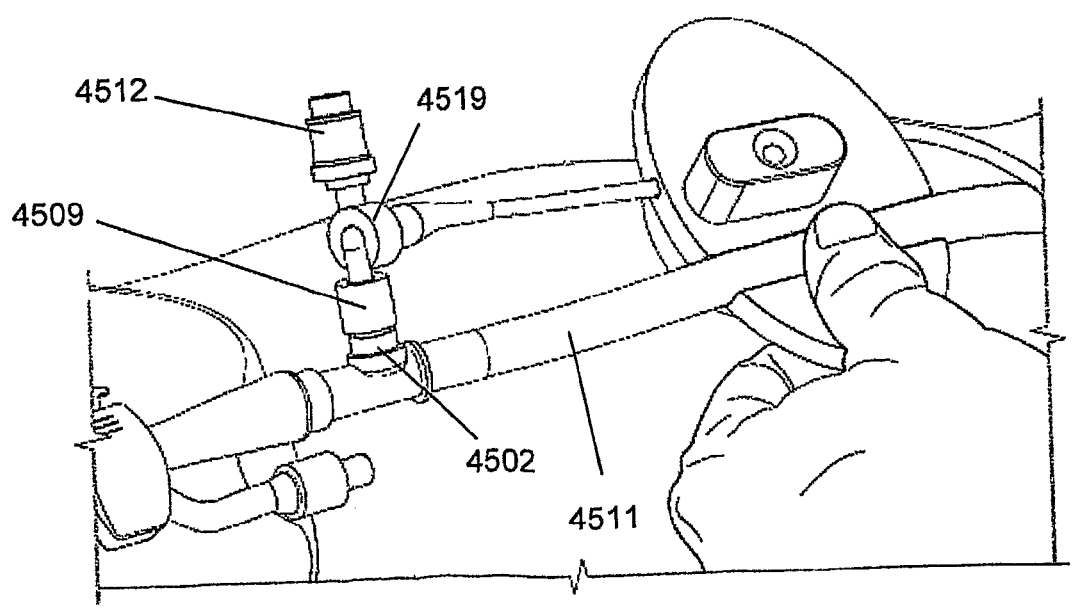

The system for measuring IAP shown in FIGS. 45A-45D is operated by first attaching the sampling port 4502 of the catheter system (e.g., a catheter system that has already been inserted into a subject) to the urinary catheter bypass system by connecting the sampling port 4502 to a sampling port connector 4509. As described above, the sampling port connector may include an EZ-LOCK™ attachment to removably secure the sampling port to the connector and prevent leak through the connection. Connecting the sampling port and the sampling port connector places the bypass lumen in fluid communication with a lumen of the urinary catheter system, and thus the bladder. The tubing 4503 forming the fluid pathway that is connected to the bypass lumen extends from the sampling port connector 4509, as shown in FIG. 45B, and the housing may be slid over the tubing 4503, as previously described and shown in FIG. 45A.

Figure 45C:
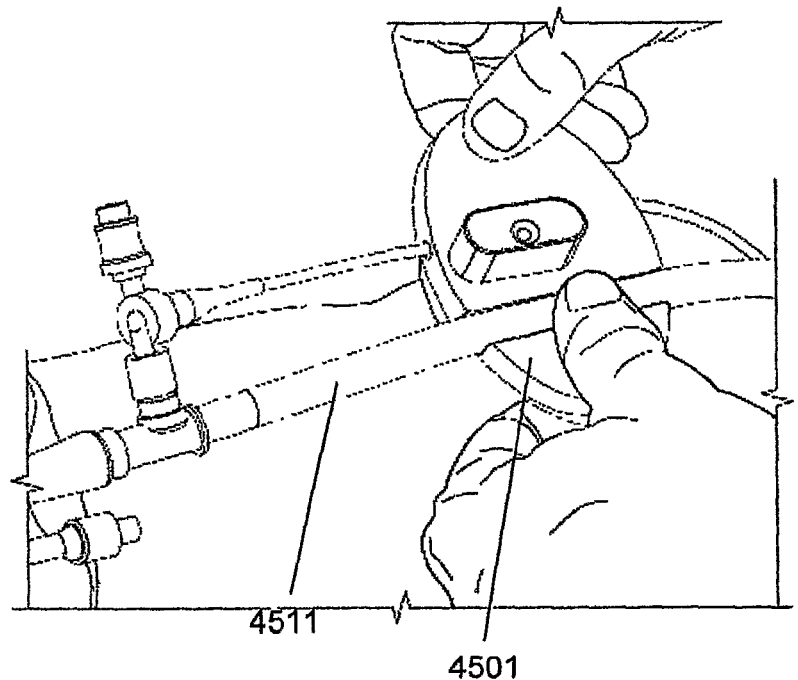
Figure 47A:
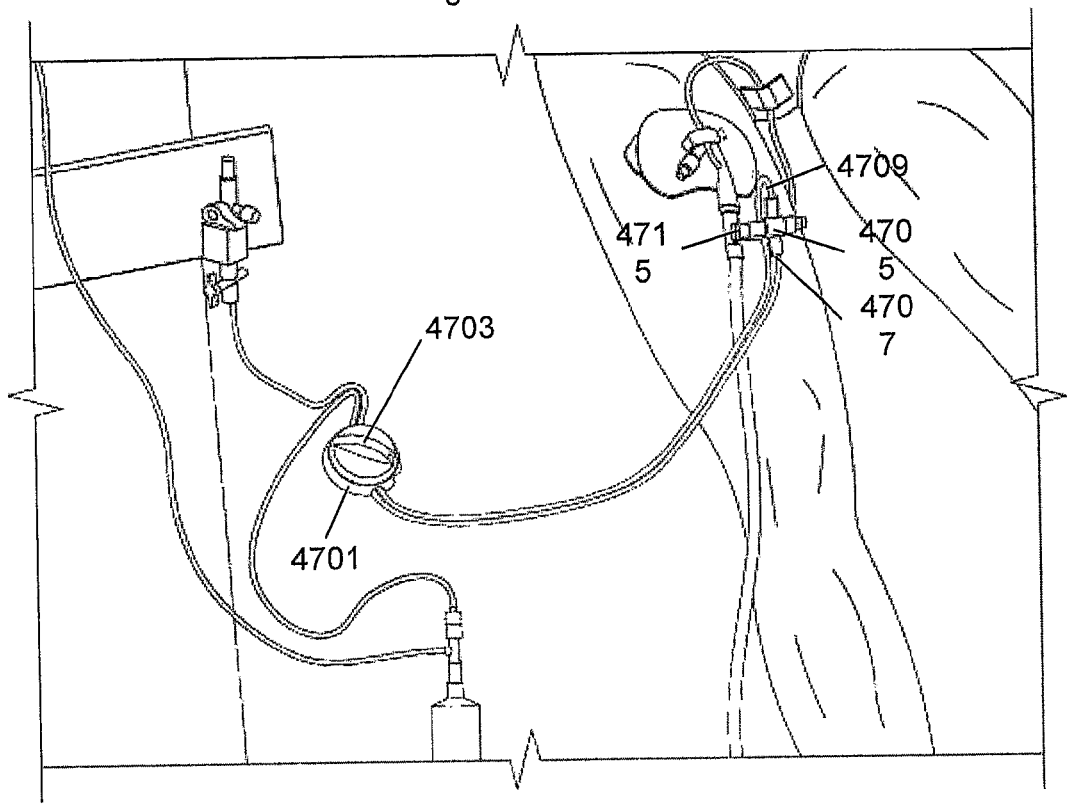
FIGS. 47A and 47B illustrates attachment of a system for measuring IAP using a testing system such as the one shown in FIG. 46.
Figure 47B:
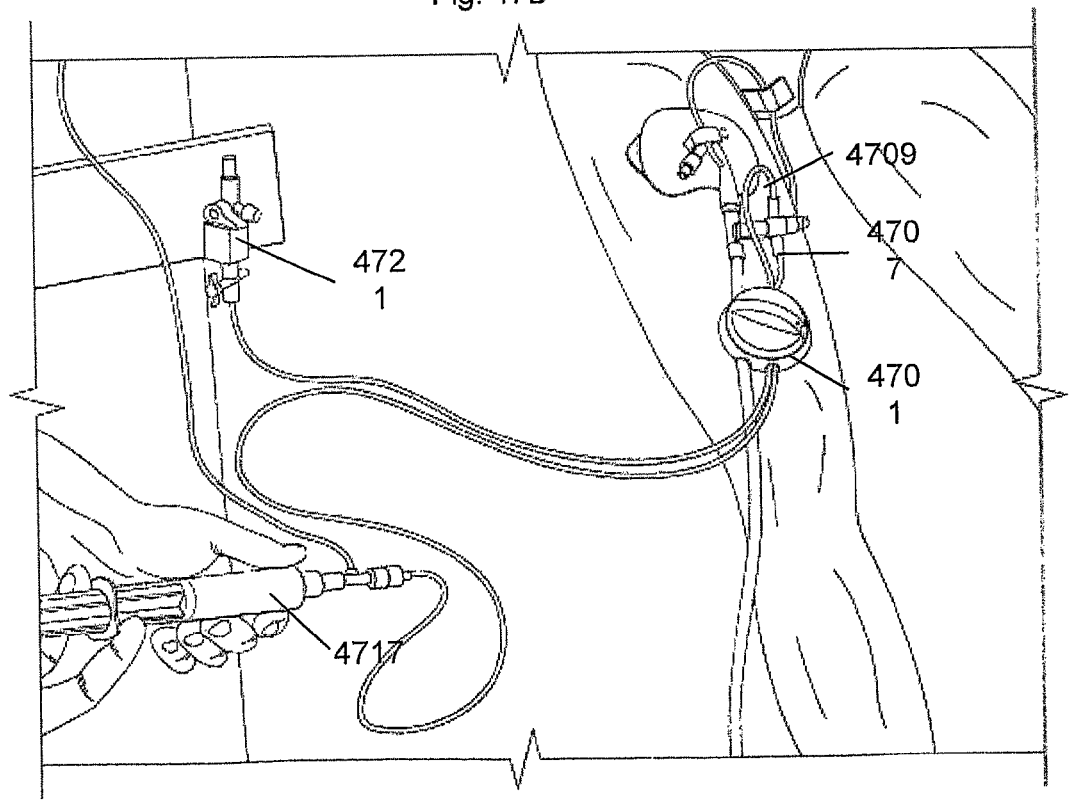

The housing may be positioned near the distal end of the drain tube, and may rest against or be attached to the subject's leg, as shown in FIG. 45C, or slid along the saline line (e.g., fluid source) and out of the way of the patient (e.g., near the side of the bed) when not in use (as shown in FIGS. 47A and 47B). Once the housing is positioned, the drain tube 4511 of the catheter system is inserted into the housing 4501. In FIG. 45C, the drain tube can be manually pushed into the channel through the housing 4501.

Figure 45D:
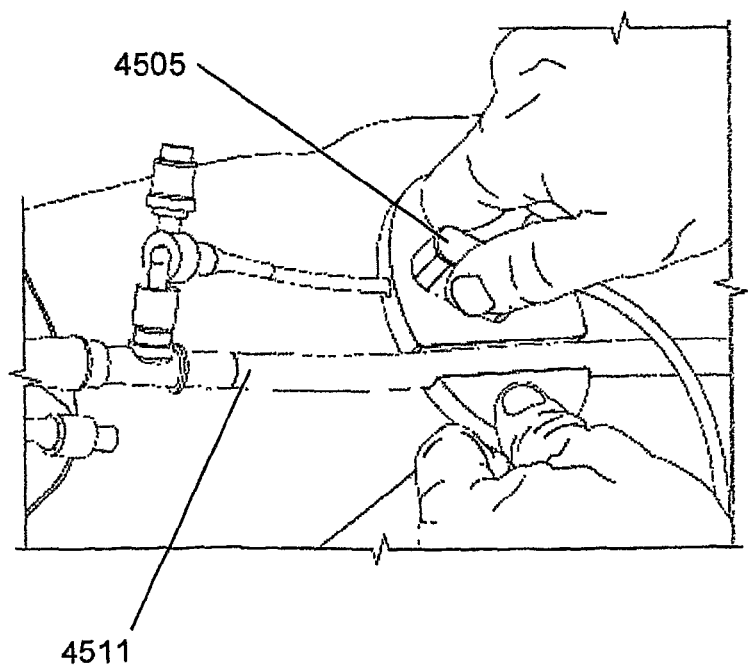

The system can then be used to measuring IAP from the catheterized subject. The selector (shown here as a knob 4505) can be used to close the drain tube (via a clamping mechanism such as a pinch valve), as illustrated in FIG. 45D. The selector can also permit fluid to be loaded into the bladder by a fluid infusion device from a fluid supply. In some variations the fluid infusion device is controlled separately, as described above. Since the bypass lumen is connected to the pressure transducer (not shown), IAP pressure measurements can be taken through the bypass lumen. The system shown in FIG. 45A-45D also includes an auxiliary sampling port 4512 so that even when the system for measuring IAP is connected, a fluid sample may be taken from the catheter. The sampling port connector may also include a valve 4519 (e.g., a one-way check valve) to prevent drawing saline into the bypass lumen when urine sampling is done through the auxiliary sampling port. Thus, the one-way check valve 4519 shown in FIG. 45B is positioned between the sampling port connector and the bypass lumen.

The system for measuring IAP may also be disconnected without having to remove the catheter from the subject. For example, the system shown in FIG. 45A-45D may be removed by turning the selector 4505 so that the drain tube 4511 is not occluded, and removing the drain tube from the housing. The sampling port connector can then be removed from the sampling port, leaving the catheter system connected to the patient, and the integrity of the catheter system undisturbed.

Figure 46:
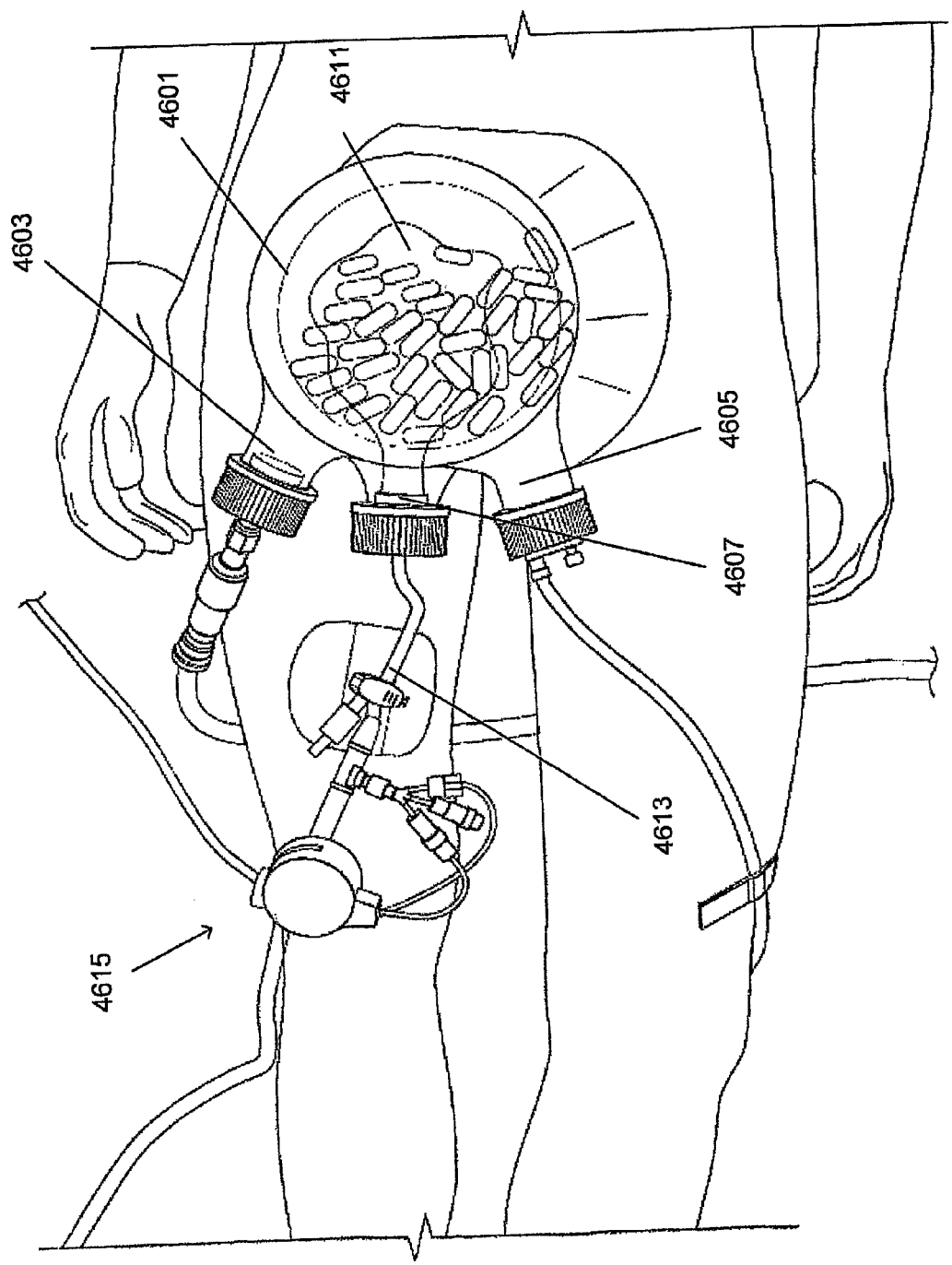
FIG. 46 shows a set-up for testing an IAP measuring device or system.

A system and/or a device for measuring IAP may be tested in a set-up such as that shown in FIG. 46. In FIG. 46, the abdominal cavity is simulated using a pressurized chamber 4601 that has an input port 4603 for controlling pressure within the chamber 4601, and a reference pressure port 4605 for measuring pressure within the chamber 4601. As third port 4607 connects to simulated bladder that is made up of a thin plastic bag (or other air-tight but compressible structure) 4611 within the pressurized chamber 4601. A Foley catheter 4613 is positioned within this simulated bladder 4611.

In FIG. 46 a urinary catheter bypass system 4615 is attached to the catheter system. In another embodiment, a bypass system similar to the system shown in FIG. 30B may be used. FIG. 47A shows the attachment of the system for measuring IAP to the catheter system. In FIG. 47A, the device for measuring IAP includes a drain tube housing 4701 enclosing a clamp mechanism (not visible) controlled by a selector (dial 4703). The device also includes a sampling port connector 4705 that includes a bypass lumen. The bypass lumen is connected to a first fluid pathway (e.g., fluid infusion pathway, enclosed by tubing 4707) that is configured to be connected to a fluid supply and/or a fluid infuser, as well as a second fluid pathway (e.g., pressure transducer pathway, enclosed by tubing 4709). The second fluid pathway is connected to the pressure transducer 4721.

Figure 47C:
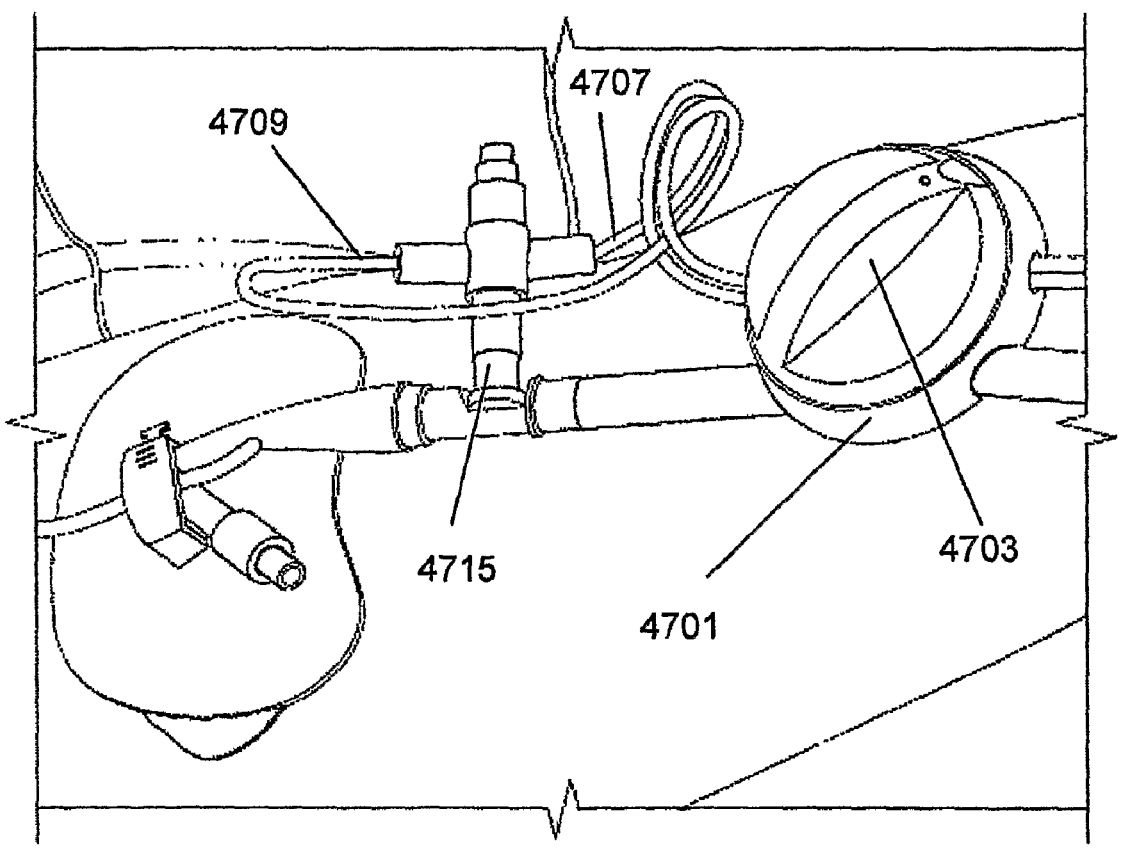
FIG. 47C shows a close-up view of a portion of the device for testing IAP illustrated in FIGS. 47A and 47B.

The housing 4701 at least partly surrounds the first and second fluid pathways. After attaching the sampling port connector 4705 to the sampling port 4715 of the catheter, the housing 4701 may be slid along the tubing enclosing the fluid pathways until it is positioned appropriately relative to the catheter, as shown in FIG. 45B. Preferably, the housing is located near the distal end of the drain tube. The drain tube can then be inserted into the housing 4701 (e.g., within a channel of the housing 4701), and the selector can be used to occlude the drain tube by controlling the clamping mechanism, and/or to application of fluid from the first fluid pathway (fluid infusion pathway 4707). FIG. 47C shows a close-up view of the housing 4701 after it has been positioned.

As mentioned, the fluid infuser is typically connected to the first fluid pathway (the fluid infusion pathway 4707). As described above, any appropriate fluid infuser may be used. In this example, a syringe 4717 (e.g., a 60 cc syringe) is used, and fluid may be drawn into the syringe by withdrawing the stopper of the syringe pulling fluid from an attached fluid reservoir. Fluid may be infused by the syringe by pushing on the syringe. A valve (or set of valves) may be used to prevent backflow of fluid into the reservoir, or withdrawal of fluid from the fluid infuser pathway connected to the bypass lumen. In some variations the system for measuring IAP may be primed by applying fluid from the fluid infusion pathway with the drain valve open. However, in some variations the system may be pre-primed. A testing system such as the system shown in FIGS. 46-47C may be used to test the activity and operation of many of the devices and systems shown herein.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. For example, in some methods for measuring IAP the order of steps may involve first occluding the drain tube, then zeroing the pressure transducer, then infusing liquid into the bladder. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

Although the majority of devices described herein are for use in measuring IAP, it should be understood that they may be used for other applications instead of, or in addition to, measuring IAP. These devices may be used anytime it is desirable to increase the pressure within the bladder, or within a catheter system. For example, the devices may be useful for rinsing a catheter system to remove blockage. Other variations are also within the scope of the methods, devices and systems described herein.

Finally, all publications and patent applications cited in this specification are herein incorporated by reference in their entirety as if each individual publication or patent application were specifically and individually put forth herein.

What is claimed is:

1. A method of measuring intra-abdominal pressure without breaking a closed urinary catheter system, comprising:
   providing a urinary catheter system bypass device, comprising:
      a sampling port connector fluidly connected to a bypass lumen; and
      a drain tube housing, configured to at least partially enclose a portion of a drain tube of a urinary catheter system, the drain tube housing including a clamp mechanism configured to controllably occlude a lumen of the urinary catheter system drain tube;
   inserting the drain tube of the urinary catheter system into the drain tube housing of the urinary catheter system bypass device, including separating a first region of the drain tube housing from a second region of the drain tube housing and inserting the drain tube between the first and second regions of the drain tube housing;
   attaching the urinary catheter system bypass device to a sampling port of the urinary catheter system;
   occluding the drain tube of the urinary catheter system;
   infusing fluid into the urinary catheter system; and
   detecting intra-abdominal pressure.

2. The method of claim 1, further comprising opening the drain tube of the urinary catheter.

3. The method of claim 2, wherein opening the drain tube further comprises occluding the bypass lumen.

4. The method of claim 1, wherein occluding the drain tube of the urinary catheter system comprises activating the clamp mechanism of the urinary catheter system bypass device.

5. The method of claim 4, wherein activating the clamp mechanism of the urinary catheter system bypass device comprises pinching the drain tube.

6. The method of claim 4, wherein occluding the drain tube comprises bending the drain tube.

7. The method of claim 1, wherein the drain tube housing is constructed of a polymeric material.

8. The method of claim 1, wherein the drain tube housing is constructed of a metal or alloy.

9. The method of claim 1, further comprising sliding the drain tube housing over an outside surface of the drain tube.

10. The method of claim 1, wherein the drain tube is secured in the drain tube housing by at least one active stay, wherein the active stay comprises a spring element, biased pin, or moving disk.

11. The method of claim 1, wherein the drain tube housing accommodates drain tubes of different outer diameters.

12. The method of claim 1, wherein the clamp mechanism is controlled by a rotatable knob.

13. The method of claim 1, further comprising infusing fluid from a fluid source into the urinary catheter system.

14. The method of claim 1, further comprising detecting intra-abdominal pressure multiple additional times while the drain tube housing is disposed on the drain tube.

15. A method of measuring intra-abdominal pressure without breaking a closed urinary catheter system, comprising:
   providing a urinary catheter system bypass device, comprising:
      a bypass lumen;
      a slidable drain tube housing configured to at least partially enclose a portion of a drain tube of a urinary catheter system; and
      an occlusion mechanism configured to controllably occlude a lumen of the drain tube;
   inserting the drain tube into the drain tube housing of the urinary catheter system bypass device;
   sliding the drain tube housing along the drain tube to a desired location;
   attaching the urinary catheter system bypass device to a sampling port of the urinary catheter system; and
   detecting intra-abdominal pressure.

16. The method of claim 15, wherein after the drain tube is inserted into the drain tube housing, the drain tube is secured in the drain tube housing by at least one stay.

17. The method of claim 16, wherein each at least one stay is a protrusion that helps to hold the drain tube within the drain tube housing.

18. The method of claim 16, wherein the at least one stay is an active stay.

19. The method of claim 18, wherein the active stay comprises a spring element, biased pin, or moving disk.

20. The method of claim 16, wherein the drain tube housing accommodates drain tubes of different outer diameters.

21. The method of claim 15, wherein the occlusion mechanism is controlled by a rotatable knob.

22. The method of claim 15, wherein the occlusion mechanism is controlled by a switch.

23. The method of claim 15, further comprising infusing fluid from a fluid source into the urinary catheter system.

24. The method of claim 15, further comprising detecting intra-abdominal pressure multiple additional times while the drain tube housing is disposed on the drain tube.

25. The method of claim 15, wherein the drain tube housing includes an opening positioned on the upper surface of the housing, such that the drain tube may be easily accessed.

26. The method of claim 15, wherein occluding the drain tube of the urinary catheter system comprises activating the occlusion mechanism of the urinary catheter system bypass device.

* * * * *